(12) United States Patent
Detmar et al.

(10) Patent No.: US 11,390,666 B2
(45) Date of Patent: Jul. 19, 2022

(54) VASCULAR ENDOTHELIAL GROWTH FACTOR/ANTI-FIBRONECTIN ANTIBODY FUSION PROTEINS

(71) Applicant: Philogen S.P.A., Siena (IT)

(72) Inventors: Michael Detmar, Zürich (CH); Dario Neri, Zürich (CH); Cornelia Winter Halin, Zürich (CH); Teresa Hemmerle, Zürich (CH); Simon Schwager, Zürich (CH); Silvana Renner, Zürich (CH)

(73) Assignee: PHILOGEN S.P.A.

( * ) Notice: Subject to any disclaimer, the term of this patent is extended or adjusted under 35 U.S.C. 154(b) by 0 days.

(21) Appl. No.: 16/619,326

(22) PCT Filed: Jun. 6, 2018

(86) PCT No.: PCT/EP2018/064900
§ 371 (c)(1),
(2) Date: Dec. 4, 2019

(87) PCT Pub. No.: WO2018/224550
PCT Pub. Date: Dec. 13, 2018

(65) Prior Publication Data
US 2021/0163579 A1    Jun. 3, 2021

(30) Foreign Application Priority Data

Jun. 7, 2017 (GB) ..................................... 1709080
Oct. 10, 2017 (GB) ..................................... 1716594

(51) Int. Cl.
*C07K 16/18* (2006.01)
*C07K 16/22* (2006.01)
*C07K 14/475* (2006.01)

(52) U.S. Cl.
CPC .............. *C07K 16/18* (2013.01); *C07K 16/22* (2013.01); *C07K 14/475* (2013.01); *C07K 2317/626* (2013.01)

(58) Field of Classification Search
CPC ................................. C07K 16/18; C07K 16/22
See application file for complete search history.

(56) References Cited

U.S. PATENT DOCUMENTS

| | | |
|---|---|---|
| 5,565,332 A | 10/1996 | Hoogenboom et al. |
| 5,733,743 A | 3/1998 | Johnson et al. |
| 5,858,657 A | 1/1999 | Winter et al. |
| 5,871,907 A | 2/1999 | Winter et al. |
| 5,872,215 A | 2/1999 | Osbourne et al. |
| 5,885,793 A | 3/1999 | Griffiths et al. |
| 5,962,255 A | 10/1999 | Griffiths et al. |
| 5,969,108 A | 10/1999 | McCafferty et al. |
| 6,140,471 A | 10/2000 | Johnson et al. |
| 6,172,197 B1 | 1/2001 | McCafferty et al. |
| 6,225,447 B1 | 5/2001 | Winter et al. |
| 6,291,650 B1 | 9/2001 | Winter et al. |
| 6,492,160 B1 | 12/2002 | Griffiths et al. |
| 6,521,404 B1 | 2/2003 | Griffiths et al. |

FOREIGN PATENT DOCUMENTS

| | | |
|---|---|---|
| WO | 00/75329 A1 | 12/2000 |
| WO | 02/46455 A1 | 6/2002 |
| WO | 2008/120101 A2 | 10/2008 |
| WO | 2009/056268 A1 | 5/2009 |
| WO | 2010/078945 A2 | 7/2010 |
| WO | 2013/014149 A1 | 1/2013 |
| WO | 2014/055073 A1 | 4/2014 |

OTHER PUBLICATIONS

Alitalo, A., "VEGF-C and VEGF-D Blockade Inhibits Inflammatory Skin Carcinogenesis", Cancer Res., 73(14): 4212-21 (2013).
Baluk, P. et al., "Preferential Lymphatic Growth in Bronchus-Associated Lymphoid Tissue in Sustained Lung Inflammation", Am. J. Pathol., 184(5): 1577-1592 (2014).
Balza, E. et al., "Transforming growth factor B regulates the levels of different fibronectin isoforms in normal human cultured fibroblasts", FEBS Letters, 228(1): 42-44 (1988).
Bentzon, J. et al., "Mechanisms of Plaque Formation and Rupture", Cir. Res., 114: 1852-1866 (2014).
Bootz, F. et al., "Alternatively spliced EDA Domain of Fibronectin is a Target for Pharmacodelivery Applications in Inflammatory Bowel Disease", Inflamm. Bowel Dis., 21: 1908-1917 (2015).
Bootz, F. et al., "Antibody-Based Targeted Delivery of Interleukin-22 Promotes Rapid Clinical Recovery in Mice with DSS-Induced Colitis", Inflamm. Bowel Dis., 22: 2098-2105 (2016).
Borsi, L. et al., "Transforming growth factor-B regulates the splicing pattern of fibronectin messenger RNA precursor", FEBS Letters, 261(1): 175-178 (1990).
Card, C. et al., "Emerging roles of lymphatic endothelium in regulating adaptive immunity", The Journal of Clinical Investigation, 124(3): 943-952 (2014).
Carnemolla, B. et al., "A Tumor-Associated Fibronectin Isoform Generated by Alternative Splicing of Messenger RNA Precursors", The Journal of Cell Biology, 108: 1139-1148 (1989).
D'Alessio, S. et al., "VEGF-C-dependent stimulation of lymphatic function ameliorates experimental inflammatory bowel disease", J. Clin. Investig., 124(9): 3863-3878 (2014).
Gousopoulos, E. et al., "An Important Role of VEGF-C in Promoting Lymphedema Development", J. Investig. Dermatol., 137: 1995-2004 (2017).

(Continued)

*Primary Examiner* — Christina M Borgeest
(74) *Attorney, Agent, or Firm* — Kathleen D. Rigaut; Howson & Howson LLP

(57) ABSTRACT

The application relates to a fusion protein comprising an antibody molecule, or antigen-binding fragment thereof, and a member of the vascular endothelial growth factor family, such as VEGF-C or VEGF-D. The antibody molecule preferably binds an antigen associated with angiogenesis, such as the ED-A isoform of fibronectin. In particular, the application relates to the therapeutic use of such fusion protein in the treatment of an inflammatory disease or disorder.

4 Claims, 27 Drawing Sheets

Specification includes a Sequence Listing.

(56) References Cited

OTHER PUBLICATIONS

Halin, C. et al., "Tumor-Targeting Properties of Antibody-Vascuar Endothelial Growth Factor Fusion Proteins", Int. J. Cancer, 102: 109-116 (2002).
Hemmerle, T. et al., "The antibody-based targeted delivery of TNF in combination with doxorubicin eradicates sarcomas in mice and confers protective immunity", British Journal of Cancer, 109: 1206-1213 (2013).
Hess, Christian et al., "Evaluation of antibody-chemokine fusion proteins for tumor-targeting applications", Experimental Biology and Medicine, 239: 842-852 (2014).
Holmes, David et al., "The vascular endothelial growth factor (VEGF) family: angiogenic factors in health and disease", Genome Biology, 6: 209 (2005).
Huggenberger, R. et al., "The cutaneous vascular system in chronic skin inflammation", J. Investig. Dermatol. Symp. Proc., 15(1): 24-32 (2011).
Huggenberger, R. et al., "Stimulation of lymphangiogenesis via VEGFR-3 inhibits chronic skin inflammation", J. Exp. Med., 207(10): 2255-2269 (2010).
Joukov, V. et al., "A Recombinant Mutant Vascular Endothelial Growth Factor-C that Has Lost Vascular Endothelial Growth Factor Receptor-2 Binding, Activation and Vascular Permeability Activities", The Journal of Biological Chemistry, 373(12): 6599-6602 (1998).
Jurisic, G. et al., "Blockade of VEGF receptor-3 aggravates inflammatory bowel disease and lymphatic vessel enlargement", Inflamm. Bowel. Dis., 19(9): 1983-1989 (2013).
Kaspar, M. et al., "Fibronectin as target for tumor therapy", Int. J. Cancer, 118: 1331-1339 (2006).
Kutkut, I. et al., "Lymphatic vessels: an emerging actor in atherosclerotic plaque development", Eur. J. Clin. Invest., 45(1): 100-108 (2015).
Martel, C. et al., "Lymphatic vasculature mediates macrophage reverse cholesterol transport in mice", The Journal of Clinical Investigation, 123(6): 1571-1579 (2013).
Proulx, S. et al., "Use of a PEG-conjugated bright near-infrared dye for functional imaging of rerouting of tumor lymphatic drainage after sentinel lymph node metastasis", Biomaterials, 34(21): 5128-5137 (2013).
Rybak, J. et al.,"The Extra-domain A of Fibronectin is a Vascular Marker of Solid Tumors and Metastases", Cancer Res., 67(22); 10948-57 (2007).
Schulz, M. et al., "Phenotype-based high-content chemical library screening identifies statins as inhibitors of in vivo lymphangiogenesis", PNAS, E2665-E2674 (2012).
Schwager, S. et al., "Targeted activation of lymphatic vessels alleviates skin inflammation", ETH Zurich, May 24, 2018.
Schwager, K. et al., "Preclinical characterization of DEKAVIL (F8-IL10), a novel clinical stage immunocytokine which inhibits the progression of collagen-induced arthritis", Arthritis Reserach and Therapy, 11: R142 (2009).
Schwager, K. et al.,"The antibody-mediated targeted delivery of iterleukin-10 inhibits endometriosis in a syngeneic mouse model", Human Reproduction, 26(9): 2344-2352 (2011).
Stacker, Steven A. et al., "Biosynthesis of Vascular endothelial Growth Factor-D Involves Proteolytic Processing Which Generates Non-Covalent Homodimers", The Journal of Biological Chemistry, 274(45): 32127-32136 (1999).
Villa, A. et al., "A high-affinity human monoclonal antibody specific to the alternatively spliced EDA doain of fibronectin efficiently targets tumor neo-vasculature in vivo", Int. J. Cancer, 122: 2405-2413 (2008).
Zhang, Q. et al., "Icreased lymphangiogenesis in joints of mice with inflammatory arthritis", Arthritis Research & Therapy, 9: R118 (2007).
International Search Report/Written Opinion, issued in corresponding International Application No. PCT/EP2018/064900, filed Jun. 6, 2018.
Zhou, Q. et al., "VEGF-C attenuates joint damage in chronic inflammatory arthritis by accelerating local lymphatic drainage", Arthritis rheum., 63(8): 2318-2328 (2011).
Carnemolla, B. et al., "Comparison of hyuman tenascin expression in normal, Simian-viryus-40-transformed and tumor derived cell lines", Eur. J Chem., 205: 562-567 (1992).
Waltenberger, J. et al., "Different signal Transduction Properties of KDR and Flt1, Two Receptors for Vascular Endothelial Growth Factor", The Journal of Biological Chemistry, 269(43): 26988-26995 (1994).
Hu, S, et al., "Minibody: A Novel Engineered Anti-Carcinoembryonic Antigen Antibody Fragment (Single-Chain Fv-CH3) Which Exhibits Rapid, High-Level Targeting of Xenografts", Cancer Research, 56: 3055-3061 (1996).
Huston et al., "Protein engineering of antibody binding sites; Recovery of specific activity in an anti-digoxin single-chain Fv analogue produced in*Escherichia coli*", Proc. Natl. Acad. Sci. USA, 85: 5879-5883 (1988).
Segal, D. et al., "The Three-Dimensional Structure of a Phosphorylcholine-Binding Mouse Immunoglobulin Fab and the Nature of the Antigen Binding Site", PNA USA, 71(11): 4298-4302 (1974).
Detmar et al., Increased Microvascular density and enhanced leukocyte rolling and adhesion in the skin of VEGF transgenic mice, J. Invest. Dermatol., 111: 1-6 (1998).
Kunstfeld et al., "Induction of cutaneous delayed-type hypersensitivity reactions in VEGF-A transgenic mice results in chronic skin inflammation associated with persistent lymphatic hyperplasia", Blood, 104: 1048-57 (2004).
Schonthaler, H. et al., "Systemic Anti-VEGF Treatment Strongly Reduces Skin Inflammation in a Mouse Model of Psoriasis", PNAS USA, 106(50): 21264-69 (2009).

A

B

C

D

E

F

VASCULAR ENDOTHELIAL GROWTH FACTOR/ANTI-FIBRONECTIN ANTIBODY FUSION PROTEINS

CROSS-REFERENCE TO RELATED APPLICATIONS

The present application is a § 371 of International Patent Application No. PCT/EP2018/064900, filed Jun. 6, 2018, which claims priority from GB 1709080.4 filed 7 Jun. 2017 and GB 1718594.5 filed 10 Oct. 2017. The entire disclosure of each of the aforesaid applications is incorporated by reference in the present application.

INCORPORATION-BY-REFERENCE OF MATERIAL SUBMITTED IN ELECTRONIC FORM

Incorporated herein by reference in its entirety is the Sequence Listing submitted via EFS-Web as a text file named DetmarSequenceListing.txt., created Mar. 23, 2020 and having a size of 33,670 bytes.

FIELD OF THE INVENTION

The present invention relates to a conjugate comprising an antibody molecule, or antigen-binding fragment thereof, and a member of the vascular endothelial growth factor family, such as VEGF-C or VEGF-D. The antibody molecule preferably binds an antigen associated with angiogenesis, such as the ED-A isoform of fibronectin. In particular, the present invention relates to the therapeutic use of such conjugates in the treatment of an inflammatory disease or disorder.

BACKGROUND TO THE INVENTION

Angiogenesis and lymphangiogenesis describe the growth of new blood and new lymphatic vessels from existing blood and lymphatic vessels respectively. Blood and lymphatic vasculatures play a major role under physiological conditions but may also play a role in acute and chronic inflammatory diseases. In fact, vascular remodelling is one characteristic of many inflammatory diseases such as psoriasis, chronic airway inflammation, inflammatory bowel disease, atherosclerosis, and rheumatoid arthritis (Huggenberger and Detmar, "*The cutaneous vascular system in chronic skin inflammation*", J Investig Dermatol Symp Proc. (2011) 15: 24-32; Baluk P, Adams A, Phillips K, et al. "*Preferential lymphatic growth in bronchus-associated lymphoid tissue in sustained lung inflammation*", Am J Pathol. 2014; 184(5): 1577-1592; Jurisic G, Sundberg J P, Detmar M. "*Blockade of VEGF receptor-3 aggravates inflammatory bowel disease and lymphatic vessel enlargement*", Inflamm Bowel Dis. 2013; 19(9):1983-1989; Kutkut I, Meens M J, Kwak B R et al. "*Lymphatic vessels: an emerging actor in atherosclerotic plaque development*", Eur J Clin Invest. 2015; 45(1)100-8); Zhang Q, Lu Y, Proulx S T, et al. "*Increased lymphangiogenesis in joints of mice with inflammatory arthritis*", Arthritis Res Ther. 2007; 9(6); all documents referred to in this application are incorporated herein by reference in their entirety). Notably, in all of these pathologies, induction of lymphatic vasculature has been shown to be associated with a reduction in disease severity.

VEGF

The vascular endothelial growth factor (VEGF) family has five members in mammals, VEGF-A (or VEGF), VEGF-B, VEGF-C, VEGF-D, and placental growth factor (PGF). VEGF function is mediated through the binding to tyrosine kinase cell surface receptors (VEGFR) (Ferrara et al., "*the biology of VEGF and its receptors*", Nat Med., 2003 9(6): 669-676; Holmes et al., "*the vascular endothelial growth factor (VEGF) family: angiogenic factors in health and disease*", Genome Biol. (2005) 6(2): 209.1-209.10).

VEGF-C and its receptor, VEGFR3 (Flt-4), are implicated in the formation of the lymphatic endothelium (Holmes et al., 2005). VEGF-C activates VEGFR-3 and VEGFR-2. A mutant of VEGF-C in which the cysteine in position 156 was substituted by a serine binds and activates VEGFR-3 but neither binds VEGFR-2 nor activates its autophosphorylation or downstream signaling to the ERK/MAPK pathway (Joukov et al., "*A recombinant mutant vascular endothelial growth factor-C that has lost vascular endothelial growth factor receptor-2 binding, activation, and vascular permeability activities*". J Biol Chem. 1998; 273: 6599-6602). Huggenberger et al. have shown that the systemic inhibition of angiogenesis by blockade of VEGFR-2 significantly ameliorated the course of cutaneous inflammation, whereas inhibition of VEGFR-3 prolonged inflammatory oedema formation despite inhibition of lymphangiogenesis in a VEGF-A-driven mouse model of chronic skin inflammation. They also showed that intracutaneous injection of recombinant VEGF-C156S, which only activates VEGFR-3, significantly reduced inflammation and suggested a role of lymphatic vessel in chronic inflammation control (Huggenberger R, Ullmann S, Proulx S T, Pytowski B, Alitalo K and Detmar M., "*Stimulation of lymphangiogenesis via VEGFR-3 inhibits chronic skin inflammation. Journal of Experimental Medicine.* 2010; 207:2255-2269). In addition, Jurisic and Detmar have shown that antibody-mediated blockade of VEGFR3-signaling in interleukin 10-deficient mice suffering from inflammatory bowel disease caused an increase in severity of colon inflammation (Jurisic G, Sundberg J P, Detmar M. "*Blockade of VEGF receptor-3 aggravates inflammatory bowel disease and lymphatic vessel enlargement*", Inflamm Bowel Dis. 2013; 19(9):1983-1989). In line with these results, D'Alessio et al. have demonstrated that adenoviral delivery of VEGF-C protected against both acute and chronic colitis in two different animal models (D'Alessio S, Correale C, Tacconi C "*VEGF-C-dependent stimulation of lymphatic function ameliorates experimental inflammatory bowel disease*", J Clin Invest. 2014:124(9):3863-78). Moreover, Quan Zhou et al. have studied the role of VEGF-C in a mouse model of chronic inflammatory arthritis and reported that adenoviral delivery of VEGF-C reduced bone erosion and the area of inflammation, and improved lymphatic flow (Quan Zhou, Ruolin Guo et al. "*Vascular Endothelial Growth Factor C Attenuates Joint Damage in Chronic Inflammatory Arthritis by Accelerating Local Lymphatic Drainage in Mice*", Arthritis Rheum. 2011; 63(8):2318-28).

Vascular endothelial growth factor D (VEGF-D, also known as c-Fos-induced growth factor, FIGF) is closely related to VEGF-C. Mature VEGF-D consists of non-covalently linked, glycosylated homodimers, which are the result of extensive post-translational proteolytic processing (Stacker S A et al. "*Biosynthesis of Vascular Endothelial Growth Factor-D Involves Proteolytic Processing Which Generates Non-covalent Homodimers*", JBC. 1999; 274 (45):32127-36). VEGF-D binds to VEGFR2 and VEGFR3 (Achen M G, Jeltsch M et al. "*Vascular endothelial growth factor D (VEGF-D) is a ligand for the tyrosine kinases VEGF receptor 2 (Flk1) and VEGF receptor 3 (Flt4)*", PNAS. 1997; 95(2):548-53), thereby mediating proliferation of lymphatic endothelial cells and inducing lymphangiogenesis in vivo (Veikkola T et al. "*Signalling via vascular endothelial growth factor receptor-3 is sufficient for lymphangiogenesis in transgenic mice*", *EMBO J.* 2001; 20(6): 1223-1331). In tumor studies, VEGF-D has been shown to increase lymphatic vessel growth and metastasis (Stacker S. A. et al. "*VEGF-D promotes the metastatic spread of tumor cells via the lymphatics*", *Nat. Med.* 2001; 7:186-91). In conjunction with VEGF-C, VEGF-D has further been shown to be involved in modulating the inflammatory tumor environment in a skin carcinogenesis model (Alitalo A K et al. "*VEGF-C and VEGF-D blockade inhibits inflammatory skin carcinogenesis*", *Cancer Res.* 2013; 73(14):4212-21).

Fibronectin

Fibronectin (FN) is a glycoprotein widely expressed in a variety of normal tissues and body fluids. It is a component of the extracellular matrix (ECM), and plays a role in many biological processes, including cellular adhesion, cellular migration, hemostasis, thrombosis, wound healing, tissue differentiation and oncogenic transformation. Fibronectin is subject to alternative splicing of three regions (ED-A, ED-B, IIICS) of the primary transcript FN pre-mRNA, a process that is modulated by cytokines and extracellular pH (Balza E. et al. "Transforming growth factor beta regulates the levels of different fibronectin isoforms in normal human cultured fibroblasts." FEBS Lett. 1988; 228(1):42-4; Carnemolla B. et al. "A tumor-associated fibronectin isoform generated by alternative splicing of messenger RNA precursors." J Cell Biol. 1989; 108:1139-48; Borsi L. et al. "Transforming growth factor-beta regulates the splicing pattern of fibronectin messenger RNA precursor." FEBS Lett. 1990; 261(1): 175-8). Fibronectin contains two type-III globular extra-domains which may undergo alternative splicing: ED-A and ED-B (Kaspar M. et al. "Fibronectin as target for tumor therapy." Int J Cancer. 2006, 118(6):1331-9) which are known markers of angiogenesis.

ED-A

ED-A is a 90 amino acid sequence which is inserted into fibronectin (FN) by alternative splicing and is located between domain 11 and 12 of FN (Borsi et al. (1987), *J. Cell. Biol.*, 104, 595-600). Expression of ED-A in the healthy adult is confined to vascular structures in few tissues in which physiological angiogenesis takes place, namely placenta, the endometrium in the proliferative phase and some vessels in the ovaries (Schwager K, Kaspar M, Bootz F, et al. *Preclinical characterization of DEKAVIL (F8-IL10), a novel clinical-stage immunocytokine which inhibits the progression of collagen-induced arthritis. Arthritis Res Ther* 2009; 11: R142). The ED-As of mouse fibronectin and human fibronectin are 96.7% identical (only 3 amino acids differ between the two 90 amino acid sequences). ED-A is abundant during embryogenesis, tissue remodeling, fibrosis, cardiac transplantation and solid tumour growth.

The F8 Antibody

The F8 antibody is a high-affinity antibody specific to the alternatively spliced ED-A domain of fibronectin (Villa A, Trachsel E, Kaspar M, et al., "*A high-affinity human monoclonal antibody specific to the alternatively spliced EDA domain of fibronectin efficiently targets tumor neo-vasculature in vivo*". Int J Cancer 2008, 122: 2405-13; WO2008/120101; WO2009/013619).

The ED-A of fibronectin has been shown to be a marker of tumor angiogenesis (Rybak et al. (2007) *Cancer Res.* 67, 10948-10957), and the F8 antibody has been used for tumor targeting alone (WO2008/12001, WO2009/136619, WO2011/015333) or fused to TNF or IL2 or both (Villa et al. (2008) *Int. J. Cancer* 122, 2405-2413; Hemmerle et al. (2013) *Br. J. Cancer* 109, 1206-1213; Frey et al. (2008) *J. Urol.* 184, 2540-2548, WO2010/078945, WO2008/120101, WO2016/180715), to IL4 (WO2014/173570), or to IL12 (WO2013/014149).

Expression of the ED-A of fibronectin has also been reported in inflammatory disease such as rheumatoid arthritis (WO2009/056268), endometriosis (WO2010/078950), inflammatory bowel disease (WO2014/055073), psoriasis and atherosclerosis.

The F8 antibody, fused to the anti-inflammatory cytokine IL10 or IL4, has been shown to provide a therapeutic benefit in a mouse model of rheumatoid arthritis (WO2009/056268 and WO2014/173570). The F8 antibody fused to the interleukin IL4, selectively localizes to neovascular structures at sites of rheumatoid arthritis in the mouse. When used in combination with dexamethasone, F8-IL4 was able to cure mice with established collagen-induced arthritis (Hemmerle et al., "*Antibody-based delivery of IL4 to the neovasculature cures mice with arthritis*", Proc Natl Acad Sci USA., 2014 Aug. 19; 111(33):12008-12, WO2014/173570).

The F8 antibody has also been shown to give a strong staining pattern on human endometriotic tissue, as well as to accumulate on endometriotic lesions in a mouse model of endometriosis (WO2010/078950).

The F8 antibody, fused to the interleukin IL4 has been shown to inhibit the development of endometriosis in a syngeneic mouse model by likely impairing adhesion, invasion, and vascularization of the ectopic endometrium (WO2014/173570, Quattrone et al., "*the targeted delivery of interleukin 4 inhibits development of endometriotic lesions in a mouse model*", Reprod Sci. 2015 September; 22(9): 1143-52).

The F8 antibody, fused to the anti-inflammatory cytokine IL10, has been shown to reduce the endometriotic lesions in vivo in a mouse model of endometriosis (Schwager et al., "*The antibody-mediated targeted delivery of interleukin-10 inhibits endometriosis in a syngeneic mouse model*". Hum Reprod. 2011 September; 26(9):2344-52).

The ED-A of fibronectin has further been identified as a target for antibody-based pharmacodelivery applications in inflammatory bowel disease (IBD) such as ulcerative colitis. The antibody-based fusion protein IL22-F8 was able to selectively localize at inflamed sites in the DSS mouse model of colitis and to promote a rapid recovery from the disease accompanied by improved morphology of the colon (Bootz et al. "*Antibody-Based Targeted Delivery of Interleukin-22 Promotes Rapid Clinical Recovery in Mice With DSS-Induced Colitis*" (2016) *Inflamm. Bowel Dis*. September; 22(9):2098-105).

The F8 antibody, fused to the p40 subunit of murine IL12 mediated an anti-inflammatory activity in IBD (Bootz, F., Schmid, A. S. & Neri, D. *Alternatively Spliced EDA Domain of Fibronectin Is a Target for Pharmacodelivery Applications in Inflammatory Bowel Disease. Inflammatory bowel diseases* (2015)).

Furthermore, the F8 antibody, fused to the anti-inflammatory cytokine IL10, has been shown to target the colon and decreased serum cytokines in a murine IBD model. The F8 antibody in SIP format was further shown to stain the newly formed blood vessels but not the normal blood vessels in a patient affected by ulcerative colitis (WO2014/055073).

F8 has also been used to selectively deliver immunomodulatory cytokines to sites of inflammatory skin conditions both in the acute and chronic phase. F8-IL4 was shown to decrease ear swelling and inflammation in two immunocompetent mouse models of psoriasis (WO2014/173570). The combination of F8-IL4 with TNF blockade or IL17 blockade potentiated the single agent activity of F8-IL4 (Hemmerle et al., *J Dermato Science*, 2014).

An immunohistochemical analysis of F8 for the staining of atherosclerotic plaques from human carotids has revealed a strong reaction with both stable and unstable plaques (Pedretti M, Rancic Z, Soltermann A, et al. "*Comparative immunohistochemical staining of atherosclerotic plaques using F16, F8 and L19: three clinical-grade fully human antibodies*". Atherosclerosis 2009; 208:382-9). The radioiodinated monoclonal antibody F8 in SIP format was assessed for targeting the atherosclerotic plaques in the ApoE−/− mouse model. The F8 antibody was shown to be capable of selectively localizing to atherosclerotic plaques, in particular to all plaques within the aorta, following intravenous administration in ApoE−/− mice fed with a cholesterol rich diet. The F8 antibody displayed a good plaque targeting performance, thus making it a good candidate for in vivo plaque imaging applications and for pharmacodelivery applications (Fiechter et al., "*Comparative in vivo analysis of the atherosclerotic plaque targeting properties of eight human monoclonal antibodies*", Atherosclerosis (2011) 214: 325-330).

Atherosclerosis

Atherosclerosis describes the thickening, hardening, loss of elasticity of arterial walls and formation of fibrofatty plaques. Typically, the disease progresses over the duration of several years or decades. Atherosclerosis has a wide range of adverse cardiovascular effects. Lesions may grow large enough to obstruct blood flow, causing coronary heart disease and angina pectoris. Furthermore, thrombi may form on the surface of (ruptured) lesions and, after displacement, occlude downstream blood vessels, resulting in myocardial infarction or pulmonary embolism.

Atherosclerosis is a complex disease and while significant scientific progress has been made in elucidating the disease mechanisms and development, understanding of its initiating factors and the availability of therapeutic options are still limited. It is widely accepted that low-density lipoprotein (LDL) has a key function. It accumulates in the arterial intima, where it aggregates and is subjected to oxidation, chronically stimulating immune cells and initiating an inflammatory response. Macrophages and smooth muscle cells (SMC) are recruited into the arterial wall. Macrophages bind and often phagocytize LDL, giving rise to foam cells and releasing pro-inflammatory cytokines such as TNF-alpha and interferon-gamma. SMCs secrete collagen, proteoglycans and elastin, generating a fibrous cap on the plaque, which stabilizes the lesion and reduces the chance of blood clotting on the plaque's surface. Eventually, macrophages/foam cells as well as SMCs undergo apoptosis or secondary necrosis, forming a necrotic core at the centre of the developing lesion. Plaques containing necrotic cores are considered to mark highly advanced atherosclerosis and may undergo calcification (Bentzon J F et al. "*Mechanisms of plaque formation and rupture*", Circ Res. 2014; 114:1852-1866).

Lymphatic vessels have been observed in atherosclerotic plaques (Kutkut I et al. "*Lymphatic vessels: an emerging actor in atherosclerotic plaque development*", Eur J Clin Invest 2015; 45 (1): 100-108). Their role in atherosclerosis is not well understood, but they may be able to interfere with disease progression by draining inflammatory mediators. In addition, lymphatic vessels are the main route for reverse cholesterol transport (RCT) from macrophages in the lesions to the liver as Martel et al. have shown in surgical and genetic mouse models (Martel C et al. "*Lymphatic vasculature mediates macrophage reverse cholesterol transport in mice*", J Clin Invest. 2013; 123(4):1571-1579).

It is important to note that atherosclerosis and associated diseases (e.g. coronary heart disease, myocardial infarction, heart failure) are estimated by the World Health Organization to cause 31% of all deaths worldwide (http://www.whoint/cardiovascular_diseases/en/), thereby representing a major public health issue. Additionally, in the case of atherosclerosis, there are currently no viable treatment options available apart from statins, which are used to prevent disease progression. Indeed, most interventions are aimed at treating downstream/atherosclerosis-associated pathologies such as heart failure or coronary heart disease.

STATEMENTS OF INVENTION

The present inventors have shown that vascular endothelial growth factors can be successfully conjugated to antibodies which bind an extra-cellular matrix component associated with angiogenesis, such as the ED-A of fibronectin, with the resulting conjugate retaining both the targeting properties of the antibody and the biological activity of VEGF-C in vitro and in vivo. This was demonstrated using both wild-type VEGF-C and a VEGFR3-specific mutant form of VEGF-C, VEGF-C156Ser. The targeted delivery of antibody-based therapeutics is far from straightforward. Although it has been shown that cytokines can be conjugated to antibody molecules to produce immunocytokines, not all immunocytokines retain the in vivo targeting properties of the parental antibody (Pasche & Neri, 2012, *Immunocytokines: a novel class of potent armed antibodies, Drug Discov. Today*, 17:583-90) or expected biological activities. The preparation of immunoconjugates with therapeutic effects, such as anti-inflammatory activity, therefore remains a challenge.

Specifically, the present inventors demonstrated that a conjugate of antibody F8, which binds the ED-A of fibronectin, and VEGF-C (F8-VEGF-C) is capable of promoting proliferation of lymphatic endothelial cells (LECs) in vitro and induces potent lymphangiogenesis in the diaphragm of FVB mouse pups in vivo. The F8-VEGF-C and F8-VEGF-C156Ser conjugates were further shown to significantly increase sprout formation of LECs coated on microcarrier beads and the F8-VEGF-C conjugate was demonstrated to be capable of increasing the migration of porcine aortic endothelial (PAE) cells overexpressing VEGFR3.

Treatment of mice with F8-VEGF-C in a mouse model of inflammation further showed that this conjugate is also capable of reducing the absolute numbers of leukocytes, regulatory T cells and γδ T cells, all of which are vitally important in the inflammatory response, thereby demonstrating that the F8-VEGF-C conjugate has an anti-inflammatory effect. This anti-inflammatory effect was shown to be more potent than that of untargeted VEGF-C.

Furthermore, treatment with the F8-VEGF-C and F8-VEGF-C156Ser conjugates was shown to significantly reduce ear oedema in two mouse models of chronic skin inflammation compared with VEGF-C fused to an irrelevant antibody, KSF (specific for hen egg lysozyme), demonstrating that targeted delivery of VEGF-C surprisingly yields therapeutic levels of VEGF-C at the site of inflammation in vivo. The effect of the F8-VEGF-C and F8-VEGF-C156Ser conjugates on inflammation was comparable to that observed with TNFR-Fc, a standard therapy for chronic inflammatory diseases such as psoriasis and rheumatoid arthritis. Based on these results, the targeted delivery of VEGF-C is expected to represent a valuable alternative therapy to TNFR-Fc for inflammatory diseases.

F8-VEGF-C was also shown to improve lymphatic clearance from inflamed ears in a mouse model of inflammation.

The ED-A of fibronectin is known to be mainly located around blood vessels. However, as blood and lymphatic vessels are located in close proximity to each other and tissue drainage is effected via the lymphatic vessels, the present inventors postulate that the F8-VEGF-C and F8-VEGF-C156Ser conjugates may therefore be targeted to both vascular compartments. Without wishing to be bound by theory, it is thought that the F8-VEGF-C and F8-VEGF-C156Ser conjugates improve lymphatic function and thus the drainage of inflammatory mediators and cells, thereby facilitating the resolution of oedema and inflammation in inflammatory disease. In addition, there has been increasing evidence over recent years that lymphatic endothelial cells can exert a wide variety of immune-modulatory effects (e.g. by regulating the entry of antigen-presenting cells into lymph nodes or by modulation of T cell activity, as reviewed in Card C M et al. "*Emerging roles of lymphatic endothelium in regulating adaptive immunity.*", *J Clin Invest.* 2014, 124(3); 943-952. A local expansion of the lymphatic vasculature as observed by the inventors after treatment with the F8-VEGF-C and F8-VEGF-C156Ser conjugates may therefore result in a local downregulation of the inflammatory response in inflammatory diseases via such mechanisms.

In addition to its potent anti-inflammatory activity, a further advantage of the F8-VEGF-C and F8-VEGF-C156Ser conjugates compared to untargeted VEGF-C is that these conjugates can be injected systemically, as demonstrated by the present inventors. This represents a great improvement over the need for local application in the case of untargeted VEGF-C, local application being hampered in cases where the disease occurs at multiple sites simultaneously (as in psoriasis or rheumatoid arthritis) or in locations inaccessible for simple injections (e.g. the gastrointestinal tract). These limitations render methods of local delivery unsuitable for clinical use and thus mean that untargeted VEGF-C is not suitable for treating such diseases in vivo.

The antibody moiety in the F8-VEGF-C and F8-VEGF-C156Ser conjugates is further expected to improve the stability of VEGF-C compared to the use of free VEGF-C in therapeutic applications, in particular its serum stability. The F8-VEGF-C conjugate was surprisingly found by the present inventors to retain activity following two freeze-thaw cycles, while VEGF-C would be expected to lose activity under these conditions.

Treatment of mice with F8-VEGF-C in a mouse model of atherosclerosis showed that F8-VEGF-C resulted in reduced triglyceride levels and a trend towards reduced cholesterol levels in the blood of treated mice. The improvement of these metabolic parameters is clinically important in the setting of atherosclerosis. F8-VEGF-C treatment also resulted in reduced lesion and necrotic core size at all sites of the vascular system studied. The lesions in mice treated with F8-VEGF-C further tended to have thicker fibrous caps and, in plaques forming around the cast in the left common carotid artery (LCCA), smooth muscle cell area was significantly increased. These smooth muscle cells also had a reduced lipid load, indicating that they were in a healthier and fitter state. All of these factors, smaller necrotic cores, thicker fibrous caps and higher numbers of "healthy" smooth muscle cells, are considered to be beneficial for lesion stability, reducing the risk of plaque rupture and subsequent adverse cardiovascular events. F8-VEGF-C treatment thus stabilized plaques and was even able to halt and reverse lesion growth. These results therefore demonstrate the therapeutic potential of F8-VEGF-C in the treatment of atherosclerosis.

Apart from statins, there are currently no viable treatment options for artherosclerosis available, which can be used to prevent disease progression in atherosclerosis. F8-VEGF-C is therefore expected to fill a therapeutic gap in the treatment of artherosclerosis. In particular, as F8-VEGF-C represents a completely new approach to the treatment of atherosclerosis, it has the potential to be used as an alternative to, or in combination with, statins in the treatment of atherosclerosis.

Based on the above findings, it is expected that conjugates capable of targeting members of the vascular endothelial growth factor family, such as VEGF-C, to the vasculature can be used to treat inflammatory diseases and disorders, such as atherosclerosis.

Thus, in a first aspect, the present invention relates to a conjugate comprising an antibody, or antigen-binding fragment thereof, which binds an extra-cellular matrix component associated with angiogenesis, and a member of the vascular endothelial growth factor family.

The present inventors have demonstrated that conjugates comprising VEGF-C, or a variant thereof, such as VEGF-C156Ser can be used to treat inflammation in mouse models of inflammation, as well as atherosclerosis. In a preferred embodiment, the conjugate of the present invention therefore comprises VEGF-C, or a variant thereof. However, as other members of the vascular endothelial growth factor family are also known to play a role in inflammation, it is expected that conjugates comprising an antibody, or antigen-binding fragment thereof, which binds an extra-cellular matrix component associated with angiogenesis, and another member of the vascular endothelial growth factor family, such as VEGF-D, or a variant thereof, will also find application in the treatment of inflammatory diseases and disorders, including atherosclerosis. Thus, in an alternative embodiment, the present invention relates to a conjugate comprising an antibody, or antigen-binding fragment thereof, which binds an extra-cellular matrix component associated with angiogenesis and VEGF-D, or a variant thereof.

The present inventors have demonstrated that conjugates comprising a diabody specific for the Extra Domain-A (ED-A) of fibronectin, antibody F8, can be used to deliver a member of the vascular endothelial growth factor family to sites of inflammation in a mouse model of inflammation and reduce the inflammatory response. In a preferred embodiment, the conjugate of the present invention therefore binds the ED-A isoform, more preferably the ED-A, of fibronectin. However, it is expected that antibodies, or antigen-binding fragments thereof, which bind other extra-cellular matrix component associated with angiogenesis, such as the ED-B isoform of fibronectin or tenascin C, could equally be used to target members of the vascular endothelial growth factor family to sites of inflammation in a patient. Thus, in an alternative embodiment, the conjugate of the invention may comprise an antibody, or antigen-binding fragment thereof, which binds the ED-B isoform of fibronectin or tenascin C, and a member of the vascular endothelial growth factor family.

The present invention also relates to a nucleic acid molecule which encodes a conjugate of the invention, as well as expression vectors comprising a nucleic acid encoding a conjugate of the invention, and host cells comprising such vectors. Methods of producing a conjugate according to the present invention, which may involve culturing a host cell of the invention, further form part of the present invention.

As detailed above, based on the findings of the present inventors, the conjugates of the invention are expected to find application in therapy, in particular the treatment of inflammatory diseases and disorders, where the inflammatory disease and/or disorder is preferably associated with and/or characterised by angiogenesis and/or lymphangiogenesis.

Thus, in a further embodiment, the present invention relates to a conjugate of the present invention for use in a method of treatment of the human body by therapy. A method of treatment, the method comprising administering a therapeutically effective amount of a conjugate according to the present invention to the patient similarly forms part of the present invention, as does the use of a conjugate of the present invention for the manufacture of a medicament. Preferably, the treatment is treatment of an inflammatory disease or disorder and the medicament is for the treatment of an inflammatory disease or disorder.

One advantage of the conjugates of the invention is that the vascular endothelial growth factor family member is targeted to the site of inflammation. This allows the conjugates to be used in the treatment of inflammatory diseases or disorders where local application of a vascular endothelial growth factor family member, such as VEGF-C, is not possible due to the diffuse nature of the disease or because the site of inflammation is not accessible by injection. Thus, in a preferred embodiment, the conjugate is administered to the patient by intravenous injection.

In addition, in a further embodiment, the present invention relates to a conjugate according to the present invention for use in a method of delivering a member of the vascular endothelial growth factor family to a site of an inflammatory disease or disorder in a patient. A method of delivering vascular endothelial growth factor family to a site of an inflammatory disease or disorder in a patient comprising administering the conjugate of the invention to the patient similarly forms part of the present invention, as does the use of a conjugate of the present invention for the manufacture of a medicament for delivering a member of the vascular endothelial growth factor family to a site of an inflammatory disease or disorder in a patient.

As already mentioned above, the targeted delivery of vascular endothelial growth factor family member, which is made possible through the use of the conjugates of the present invention, allows the treatment of inflammatory diseases and disorders where local application of a vascular endothelial growth factor family member is not possible due to the diffuse nature of the disease or because the site of inflammation is not accessible by injection. In a preferred embodiment, the inflammatory disease or disorder is selected from the group of atherosclerosis, inflammatory bowel disease, such as Crohn's disease or ulcerative colitis, lymphedema, glaucoma, macular degeneration, myocardial infarction, psoriasis, chronic airway inflammation, atopic dermatitis, and rheumatoid arthritis. More preferably, the disease is psoriasis, atopic dermatitis, atherosclerosis or inflammatory bowel disease.

DETAILED DESCRIPTION

Antibody Molecule

Figure 1:
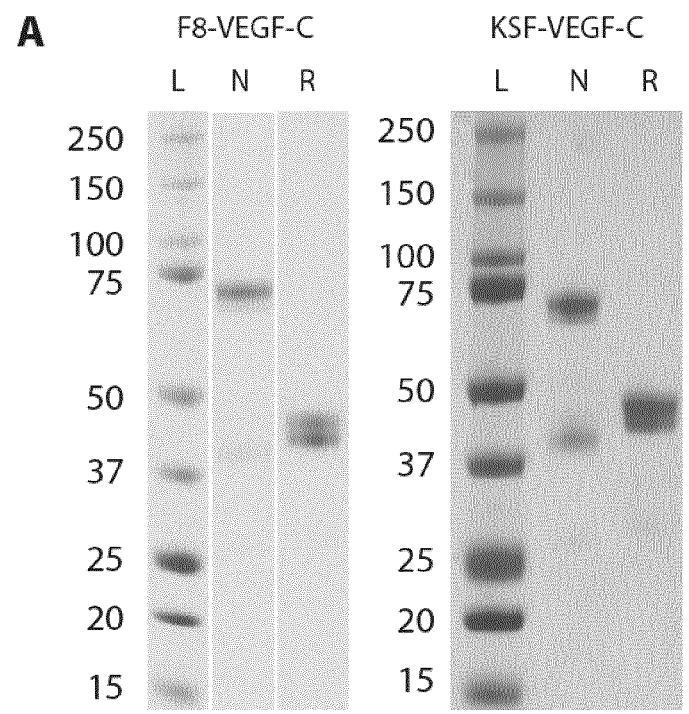
FIG. 1: Purification of KSF-VEGF-C and F8-VEGF-C. (A) Coomassie brilliant blue stainings of F8-VEGF-C (left) and KSF-VEGF-C (right) revealed the proteins to be mainly present as dimers under non-reducing conditions (1 μg of purified protein/lane). L: ladder, N: non-reducing conditions, R: reducing conditions. (B) Size-exclusion chromatograms of F8-VEGF-C (top) and KSF-VEGF-C (bottom) confirmed purity and dimeric form of the fusion proteins. (C) Western blotting analysis showed that F8-VEGF-C and KSF-VEGF-C were recognized by an anti-VEGF-C antibody (500 ng of purified protein/lane).
Figure 1:
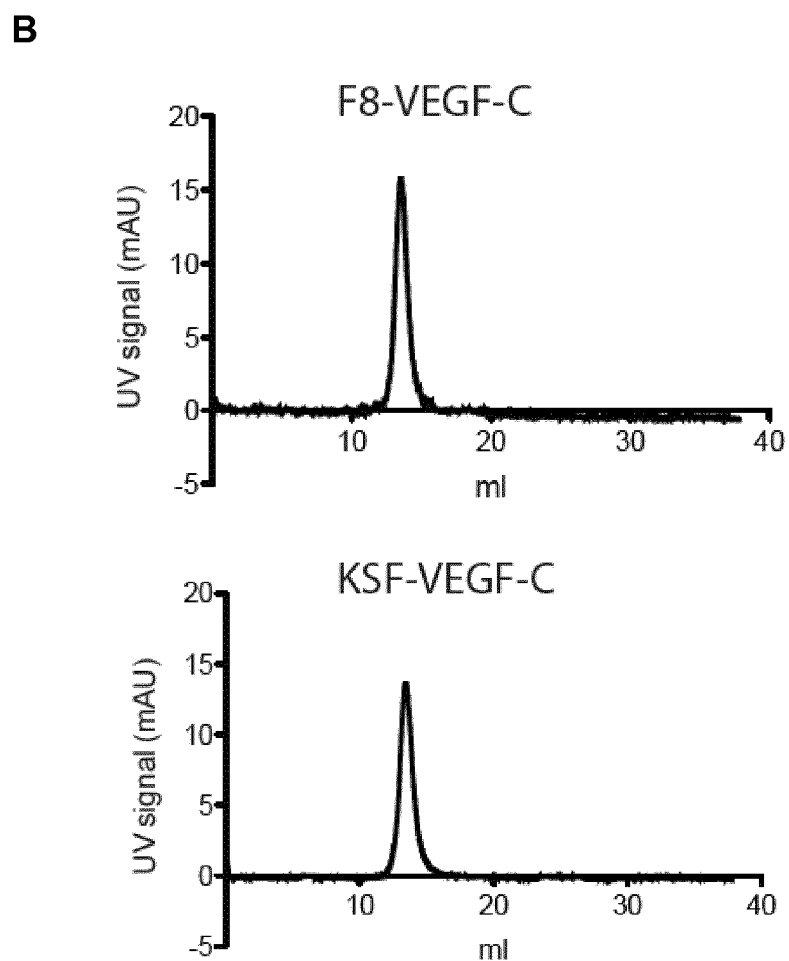

The term "antibody molecule" describes an immunoglobulin whether natural or partly or wholly synthetically produced. The term also covers any polypeptide or protein having a binding domain which is, or is substantially homologous to, an antibody binding domain.

Examples of antibody molecules are the immunoglobulin isotypes and their isotypic subclasses, as well as fragments of antibody molecules which comprise an antigen binding domain, such single chain Fvs (scFvs) and diabodies. The antibody molecule or fragment thereof may be human or humanised. The antibody molecule may be a monoclonal antibody, or a fragment thereof.

As antibodies can be modified in a number of ways, the term "antibody molecule" should be construed as covering antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

As mentioned above, fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature 341, 544-546; McCafferty et al., (1990) Nature, 348, 552-554; Holt et al. (2003) Trends in Biotechnology 21, 484-490), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by an amino acid linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger et al. (1993a), Proc. Natl. Acad. Sci. USA 90 6444-6448). Fv, scFv or diabody molecules may be stabilized by the incorporation of disulphide bridges linking the VH and VL domains (Reiter et al. (1996), Nature Biotech, 14, 1239-1245). Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The half-life of antibody molecules for use in the present invention, or conjugates of the invention, may be increased by a chemical modification, especially by PEGylation, or by incorporation in a liposome.

An antibody molecule for use in the present invention may be, or comprise, a single chain Fv (scFv), a small immunoprotein (SIP), a diabody, or an IgG molecule. Preferably, the antibody molecule for use in the present invention is, or comprises, an scFv. Diabodies, for example, comprise two scFv molecules. Most preferably, the antibody molecule for use in the present invention is a diabody. Diabodies and scFvs do not comprise an antibody Fc region, thus potentially reducing the effects of anti-idiotypic reactions.

A diabody comprises two VH-VL molecules which associate to form a dimer. The VH and VL domains of each VH-VL molecule are preferably linked by a 5 to 12 amino acid linker. For example, the VH and VL domains may be linked by an amino acid linker which is 5, 6, 7, 8, 9, 10, 11, or 12 amino acid in length. Preferably, the amino acid linker is 5 amino acids in length. Suitable linker sequences are known in the art and include the linker sequence set forth in SEQ ID NO: 4.

Where the antibody molecule is an scFv, the VH and VL domains of the antibody are preferably linked by a 10 to 20 amino acid linker. For example, the VH and VL domains may be linked by an amino acid linker which is 10, 11, 12, 13, 14, 15, 16, 17, 18, 19, or 20 amino acid in length. Suitable linker sequences are known in the art and include the linker sequences set forth in SEQ ID NO: 36 and SEQ ID NO: 37.

The present inventors have shown that a conjugate comprising VEGF-C or VEGF-C156Ser and an antibody molecule which binds the Extra-Domain A (ED-A) of fibronectin can target the neovasculature at sites of inflammation and provide potent anti-inflammatory effects compared with untargeted VEGF-C in vivo. The anti-inflammatory effects observed with these conjugates were comparable to that observed with TNFR-Fc, a standard therapy for chronic inflammatory diseases such as psoriasis and rheumatoid arthritis. Such conjugates are therefore expected to be suitable for treating inflammatory diseases and disorders in patients.

Based on these results, it is further expected that other conjugates comprising a vascular endothelial growth factor family member and an antibody, or antigen-binding fragment thereof, which binds an extra-cellular matrix component associated with angiogenesis will similarly be suitable for targeting the vascular endothelial growth factor family member to sites of inflammation in a patient with an inflammatory disease or disorder. Several extra-cellular matrix component associated with angiogenesis are known in the art, as are antibodies capable of binding such antigens. In additions, antibodies against a given antigen can be generated using well-known methods such as those described in the present application.

In one example, the antigen may be an extra-cellular matrix component associated with angiogenesis, such as a fibronectin, including the Extra-Domain A (ED-A) isoform of fibronectin (A-FN), the Extra-Domain B (ED-B) isoform of fibronectin (B-FN), tenascin C, the ED-A of fibronectin, the ED-B of fibronectin, or the A1 Domain of Tenascin C. The antigen is preferably a human antigen. Antibodies which bind the ED-A of human fibronectin, and thus also human A-FN, are known in the art and include antibody F8. Antibodies which bind the ED-B of human fibronectin, or the A1 Domain of human Tenascin C (and thus also the B-FN and tenascin C) are also known in the art and include antibodies L19 and F16, respectively. Antibodies which bind the ED-B of fibronectin, or the A1 Domain of Tenascin C, including antibodies L19 and F16, have been shown to be capable of specifically targeting neovasculature in vivo. It is thus expected that conjugates comprising a vascular endothelial growth factor family member and an antibody molecule which binds B-FN, tenascin C, the ED-B of fibronectin, or the A1 Domain of Tenascin C, will be capable of targeting vascular endothelial growth factor family member, such as VEGF-C, to neovasculature, in the same way as a conjugate comprising VEGF-C and an antibody molecule which binds A-FN, as demonstrated using antibody F8 herein and thus find application in the treatment of inflammatory diseases and disorders.

Thus an antibody molecule, or antigen-binding fragment thereof, for use in the conjugates of the invention binds an antigen associated with angiogenesis. Preferably, antibody molecule for use in the invention binds an extra-cellular matrix component associated with angiogenesis, such as A-FN, B-FN, tenascin C, the ED-A of fibronectin, the ED-B of fibronectin, or the A1 Domain of Tenascin C. More preferably, an antibody molecule for use in the invention binds the A-FN or the ED-A of fibronectin. Most preferably, an antibody molecule for use in the invention binds the ED-A of fibronectin.

In a preferred embodiment, an antibody molecule for use in the invention may have the CDRs and/or the VH and/or VL domains of antibodies F8, L19 or F16 described herein. An antibody molecule for use in the invention preferably has the CDRs of antibody F8 set forth in SEQ ID NOs 7-12. More preferably, an antibody for use in the invention comprises the VH and/or VL domains of antibody F8 set forth in SEQ ID NOs 3 and 5, respectively. Yet more preferably, an antibody for use in the invention comprises the VH and VL domains of antibody F8 set forth in SEQ ID NOs 3 and 5. The F8 antibody is preferably in diabody or scFv format, most preferably in diabody format. Where the F8 antibody is in diabody format, the antibody molecule for use in the invention preferably has the amino acid sequence set forth in SEQ ID NO: 6.

An antibody molecule for use in the invention may bind the A-FN and/or the ED-A of fibronectin, with the same affinity as anti-ED-A antibody F8 e.g. in diabody format, or with an affinity that is better. An antibody molecule for use in the invention may bind the B-FN and/or the ED-B of fibronectin, with the same affinity as anti-ED-B antibody L19 e.g. in diabody format, or with an affinity that is better. An antibody molecule for use in the invention may bind the Tenascin C and/or the A1 domain of tenascin C, with the same affinity as the antibody against the A1 domain of tenascin C, F16, e.g. in diabody format, or with an affinity that is better.

An antibody molecule for use in the invention may bind to the same epitope on A-FN and/or the ED-A of fibronectin as anti-ED-A antibody F8. An antibody molecule for use in the invention may bind to the same epitope on B-FN and/or the ED-B of fibronectin as anti-ED-B antibody L19. An antibody molecule for use in the present invention may bind to the same epitope on tenascin C and/or the A1 domain of tenascin C as antibody F16.

Variants of antibody molecules disclosed herein may be produced and used in the present invention. The techniques required to make substitutions within amino acid sequences of CDRs, antibody VH or VL domains, in particular the framework regions of the VH and VL domains, and antibody molecules generally are available in the art. Variant sequences may be made, with substitutions that may or may not be predicted to have a minimal or beneficial effect on activity, and tested for ability to bind A-FN and/or the ED-A of fibronectin, B-FN and/or the ED-B of fibronectin, tenascin C and/or the A1 domain of tenascin C, and/or for any other desired property.

It is contemplated that from 1 to 5, e.g. from 1 to 4, including 1 to 3, or 1 or 2, or 3 or 4, amino acid alterations (addition, deletion, substitution and/or insertion of an amino acid residue) may be made in one or more of the CDRs and/or the VH and/or the VL domain of an antibody molecule as described herein. Thus, an antibody molecule which binds the FN-A, FN-B, or tenascin C, may comprise the CDRs and/or the VH and/or the VL domain of antibody F8, L19, or F16 described herein with 5 or fewer, for example, 5, 4, 3, 2 or 1 amino acid alterations within the CDRs and/or the VH and/or the VL domain. For example, an antibody molecule which binds the FN-A, FN-B, or tenascin C, may comprise the VH and/or the VL domain of antibody F8, L19, or F16 described herein with 5 or fewer, for example, 5, 4, 3, 2 or 1 amino acid alterations within the framework region of the VH and/or VL domain. An antibody molecule that binds the FN-A or ED-A of fibronectin, as referred to herein, thus may comprise the VH domain shown in SEQ ID NO: 3 and/or the VL domain set forth in SEQ ID NO: 5 with 5 or fewer, for example, 5, 4, 3, 2 or 1 amino acid alterations within the framework region of the VH and/or VL domain. Such an antibody molecule may bind the ED-A isoform or ED-A of fibronectin with the same or substantially the same, affinity as an antibody molecule comprising the VH domain set forth in SEQ ID NO: 3 and the VL domain shown in SEQ ID NO: 5 or may bind the ED-A isoform or ED-A of fibronectin with a higher affinity than an antibody molecule comprising the VH domain set forth in SEQ ID NO: 3 and the VL domain set forth in SEQ ID NO: 5.

An antibody molecule for use in the invention may comprise a VH and/or VL domain that has at least 70%, more preferably one of at least 75%, 80%, 85%, 90%, 95%, 96%, 97%, 98%, 99% or 100%, sequence identity to the VH and/or VL domain, as applicable, of antibody F8, L19, or F16 set forth in SEQ ID NOs 3, 5, 24, 25, 33, 34, and 39. An antibody molecule for use in the invention may have at least 70%, more preferably one of at least 75%, 80%, 85%, 90%, 95%, 96%, 97%, 98%, 99% or 100%, sequence identity to the amino acid sequence of the F8, L19, or F16 antibodies set forth in SEQ ID NOs 6, 26, 35 and 40, respectively.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site preferably comprises an antibody light chain variable region (VL) and an antibody heavy chain variable region (VH).

An antigen binding site may be provided by means of arrangement of complementarity determining regions (CDRs). The structure for carrying a CDR or a set of CDRs will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat et al. (1987) (Sequences of Proteins of Immunological Interest. 4$^{th}$ Edition. US Department of Health and Human Services.), and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined by Kabat et al. (1987) Sequences of Proteins of Immunological Interest, 4$^{th}$ Edition, US Department of Health and Human Services (Kabat et al., (1991a), Sequences of Proteins of Immunological Interest, 5$^{th}$ Edition, US Department of Health and Human Services, Public Service, NIH, Washington, and later editions). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It can be as short as 2 amino acids although the longest size known is 26. Functionally, HCDR3 plays a role in part in the determination of the specificity of the antibody (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144: 4863-4869; Kabat et al., (1991b), J. Immunol., 147:1709-1719).

An antigen binding site forming part of an antibody molecule for use in the invention preferably comprises one or more, preferably all six of: the CDRs of antibody F8 set forth in SEQ ID NOs 7-12, the CDRs of antibody L19 set forth in SEQ ID NOs 18-23 or SEQ ID Nos 18, 38, 20, 21, 22 and 23, or the CDRs of antibody F16 set forth in SEQ ID NOs 27-32. Most preferably, an antigen binding site forming part of an antibody molecule for use in the invention comprises the CDRs of antibody F8 set forth in SEQ ID NOs 7-12.

Preparation and Selection of Antibody Molecules

Various methods are available in the art for obtaining antibodies molecules against a target antigen. The antibody molecules for use in the present invention are preferably monoclonal antibodies, especially of human, murine, chimeric or humanized origin, which can be obtained according to the standard methods well known to the person skilled in the art. An antibody molecule for use in the present invention is most preferably a human antibody molecule.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody molecule to the constant regions, or constant regions plus framework regions, of a different immunoglobulin. See, for instance, EP-A-184187, GB 2188638A or EP-A-239400, and a large body of subsequent literature. A hybridoma or other cell producing an antibody may also be subject to genetic mutation or other changes, which may or may not alter the binding specificity of antibodies produced.

Techniques available in the art of antibody engineering have made it possible to isolate human and humanised antibodies. For example, human hybridomas can be made as described by Kontermann & Dubel (2001), S, *Antibody Engineering*, Springer-Verlag New York, LLC; ISBN: 3540413545. Phage display, another established technique for generating specific binding members has been described in detail in many publications such as WO92/01047 (discussed further below) and US patents U.S. Pat. Nos. 5,969, 108, 5,565,332, 5,733,743, 5,858,657, 5,871,907, 5,872,215, 5,885,793, 5,962,255, 6,140,471, 6,172,197, 6,225,447, 6,291,650, 6,492,160, 6,521,404 and Kontermann & Dubel (2001), S, *Antibody Engineering*, Springer-Verlag New York, LLC; ISBN: 3540413545.

Transgenic mice in which the mouse antibody genes are inactivated and functionally replaced with human antibody genes while leaving intact other components of the mouse immune system, can be used for isolating human antibodies (Mendez et al., (1997), Nature Genet, 15(2): 146-156).

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein, 1975, Nature, 256:495-497.

Monoclonal antibodies can be obtained, for example, from an animal cell immunized against an antigen associated with angiogenesis, such as A-FN, B-FN, tenascin C, the ED-A of fibronectin, the ED-B of fibronectin, or the A1 Domain of Tenascin C, according to the usual working methods, by genetic recombination starting with a nucleic acid sequence contained in the cDNA sequence coding for A-FN, B-FN, or tenascin C, or fragment thereof, or by peptide synthesis starting from a sequence of amino acids comprised in the peptide sequence of the A-FN, B-FN, or tenascin C, and/or a fragment thereof.

Synthetic antibody molecules may be created by expression from genes generated by means of oligonucleotides synthesized and assembled within suitable expression vectors, for example as described by Knappik et al. (2000) J. Mol. Biol. 296, 57-86 or Krebs et al. (2001) Journal of Immunological Methods, 254 67-84.

Alternatively, one or more antibody molecules for an antigen associated with angiogenesis, such as the A-FN, the ED-A, B-FN, the ED-B, tenascin C, or the A1 domain of tenascin C may be obtained by bringing into contact a library of antibody molecules and the antigen or a fragment thereof, e.g. a fragment comprising or consisting of ED-A, ED-B, or the A1 domain of tenascin C, or a peptide fragment thereof, and selecting one or more antibody molecules of the library able to bind the antigen.

An antibody library may be screened using Iterative Colony Filter Screening (ICFS). In ICFS, bacteria containing the DNA encoding several binding specificities are grown in a liquid medium and, once the stage of exponential growth has been reached, some billions of them are distributed onto a growth support consisting of a suitably pretreated membrane filter which is incubated until completely confluent bacterial colonies appear. A second trap substrate consists of another membrane filter, pre-humidified and covered with the desired antigen.

The trap membrane filter is then placed onto a plate containing a suitable culture medium and covered with the growth filter with the surface covered with bacterial colonies pointing upwards. The sandwich thus obtained is incubated at room temperature for about 16 h. It is thus possible to obtain the expression of the genes encoding antibody fragments scFv having a spreading action, so that those fragments binding specifically with the antigen which is present on the trap membrane are trapped. The trap membrane is then treated to point out bound antibody fragments scFv with colorimetric techniques commonly used to this purpose.

The position of the coloured spots on the trap filter allows one to go back to the corresponding bacterial colonies which are present on the growth membrane and produced the antibody fragments trapped. Such colonies are gathered and grown and the bacteria-a few millions of them are distributed onto a new culture membrane repeating the procedures described above. Analogous cycles are then carried out until the positive signals on the trap membrane correspond to single positive colonies, each of which represents a potential source of monoclonal antibody fragments directed against the antigen used in the selection. ICFS is described in e.g. WO0246455.

A library may also be displayed on particles or molecular complexes, e.g. replicable genetic packages such bacteriophage (e.g. T7) particles, or other in vitro display systems, each particle or molecular complex containing nucleic acid encoding the antibody VH variable domain displayed on it, and optionally also a displayed VL domain if present. Phage display is described in WO92/01047 and e.g. US patents U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404.

Following selection of antibody molecules able to bind the antigen and displayed on bacteriophage or other library particles or molecular complexes, nucleic acid may be taken from a bacteriophage or other particle or molecular complex displaying a said selected antibody molecule. Such nucleic acid may be used in subsequent production of an antibody molecule or an antibody VH or VL variable domain by expression from nucleic acid with the sequence of nucleic acid taken from a bacteriophage or other particle or molecular complex displaying a said selected antibody molecule.

Ability to bind an antigen associated with angiogenesis, such as the A-FN, B-FN, the ED-A, or the ED-B of fibronectin, tenascin C or the A1 domain of tenascin C or other target antigen or isoform may be further tested, e.g. ability to compete with an antibody specific for the A-FN, B-FN, the ED-A, or the ED-B of fibronectin, tenascin C or the A1 domain of tenascin C, such as antibody F8, L19, or F16.

Novel VH or VL regions carrying CDR-derived sequences for use in the invention may be also generated using random mutagenesis of one or more selected VH and/or VL genes to generate mutations within the entire variable domain. In some embodiments one or two amino acid substitutions are made within an entire variable domain or set of CDRs. Another method that may be used is to direct mutagenesis to CDR regions of VH or VL genes.

Variable domains employed in the invention may be obtained or derived from any germ-line or rearranged human variable domain, or may be a synthetic variable domain based on consensus or actual sequences of known human variable domains. A variable domain can be derived from a non-human antibody. A CDR sequence for use in the invention (e.g. CDR3) may be introduced into a repertoire of variable domains lacking a CDR (e.g. CDR3), using recombinant DNA technology. For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide antibody molecules for use in the invention. The repertoire may then be displayed in a suitable host system such as the phage display system of WO92/01047, or any of a subsequent large body of literature, including Kay, Winter & McCafferty (1996), so that suitable antibody molecules may be selected. A repertoire may consist of from anything from $10^4$ individual members upwards, for example at least $10^5$, at least $10^6$, at least $10^7$, at least $10^8$, at least $10^9$ or at least $10^{10}$ members.

An antigen associated with angiogenesis, such as the A-FN, B-FN, the ED-A, or the ED-B of fibronectin, tenascin C or the A1 domain of tenascin C may be used in a screen for antibody molecules, e.g. antibody molecules, for use in the invention. The screen may a screen of a repertoire as disclosed elsewhere herein.

Similarly, one or more, or all three CDRs may be grafted into a repertoire of VH or VL domains that are then screened for an antibody molecule or antibody molecules for an antigen associated with angiogenesis, such as A-FN, B-FN, the ED-A, or the ED-B of fibronectin, tenascin C or the A1 domain of tenascin C. One or more of the HCDR1, HCDR2 and HCDR3 of antibody F8, L19, or F16, or the set of HCDRs of antibody F8, L19, or F16 may be employed, and/or one or more of the LCDR1, LCDR2 and LCDR3 of antibody F8, L19, or F16 the set of LCDRs of antibody F8, L19, or F16 may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of antibody molecules of the present invention made by recombinant DNA techniques may result in the introduction of N- or C-terminal residues encoded by linkers introduced to facilitate cloning or other manipulation steps. Other manipulation steps include the introduction of linkers to join variable domains disclosed elsewhere herein to further protein sequences including antibody constant regions, other variable domains (for example in the production of diabodies) or detectable/functional labels as discussed in more detail elsewhere herein.

Although antibody molecules may comprise a pair of VH and VL domains, single binding domains based on either VH or VL domain sequences may also be used in the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain antibody molecule able to bind an antigen associated with angiogenesis, such as A-FN, B-FN, the ED-A, or the ED-B of fibronectin, tenascin C or the A1 domain of tenascin C. This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain antibody molecule is selected in accordance with phage display techniques such as those described in that reference. This technique is also disclosed in Marks 1992.

Fragments of whole antibodies for use in the invention can be obtained starting from any of the antibody molecules described herein, e.g. antibody molecules comprising VH and/or VL domains or CDRs of any of antibodies described herein, by methods such as digestion by enzymes, such as pepsin or papain and/or by cleavage of the disulfide bridges by chemical reduction. In another manner, antibody fragments may be obtained by techniques of genetic recombination likewise well known to the person skilled in the art or else by peptide synthesis by means of, for example, automatic peptide synthesizers such as those supplied by the company Applied Biosystems, etc., or by nucleic acid synthesis and expression.

Conjugate

A conjugate according to the present invention comprises a member of the vascular endothelial growth factor family and an antibody molecule which binds an antigen associated with angiogenesis, as described herein. The antibody molecule is preferably a diabody or an scFv, most preferably a diabody, as described herein.

The member of the vascular endothelial growth factor family is preferably a member of the human vascular endothelial growth factor family. The vascular endothelial growth factor family member is preferably human VEGF-C or human VEGF-D, most preferably human VEGF-C.

Where the conjugate of the invention comprises VEGF-C, the conjugate may comprise wild-type VEGF-C, or a mutant of VEGF-C, such as VEGF-C156Ser. Preferably, the conjugate comprises VEGF-C. The VEGF-C may have at least 70%, more preferably one of at least 75%, 80%, 85%, 90%, 95%, 96%, 97%, 98%, 99% or 100%, sequence identity to the amino acid sequence set forth in SEQ ID NO: 13. Alternatively, the VEGF-C may comprise or consist of the sequence set forth in SEQ ID NO: 13 with 10 or fewer, for example, 10, 9, 8, 7, 6, 5, 4, 3, 2 or 1 amino acid alterations (addition, deletion, substitution and/or insertion of an amino acid residue). The VEGF-C156Ser mutant preferably has or comprises the sequence set forth in SEQ ID NO: 15. Most preferably, the conjugate comprises the sequence of VEGF-C set forth in SEQ ID NO: 13 or the sequence of VEGF-C156Ser set forth in SEQ ID NO: 15.

Where the conjugate comprises VEGF-D, the VEGF-D may have at least 70%, more preferably one of at least 75%, 80%, 85%, 90%, 95%, 96%, 97%, 98%, 99% or 100%, sequence identity to the amino acid sequence set forth in SEQ ID NO: 17. Alternatively, the VEGF-D may comprise or consist of the sequence set forth in SEQ ID NO: 17 with 10 or fewer, for example, 10, 9, 8, 7, 6, 5, 4, 3, 2 or 1 amino acid alterations.

The vascular endothelial growth factor family member in the conjugates of the invention preferably retains a biological activity of the vascular endothelial growth factor family member, such as the ability to inhibit inflammation. For example, the vascular endothelial growth factor family member may retain the ability to induce lymphangiogenesis.

Preferably, the antibody molecule is connected to the vascular endothelial growth factor family member through a linker, preferably an amino acid linker.

Where the antibody molecule is a two-chain or multi-chain molecule, the vascular endothelial growth factor family member may be connected to one or more polypeptide chains in the antibody molecule by means of a linker.

Where the antibody molecule is linked to the vascular endothelial growth factor family member by means of an amino acid linker, the conjugate may be or comprise a fusion protein. By "fusion protein" is meant a polypeptide that is a translation product resulting from the fusion of two or more genes or nucleic acid coding sequences into one open reading frame (ORF). Where the conjugate comprises a diabody, the two scFv molecules making up the diabody (each of which is preferably linked to the vascular endothelial growth factor family member via an amino acid linker) may each be expressed as a fusion protein and then allowed to associate to form a dimer.

The amino acid linker connecting the antibody molecule and the vascular endothelial growth factor family member may be a flexible amino acid linker. Suitable examples of amino acid linker sequences are known in the art. The linker may be 10-20 amino acids, preferably 10-15 amino acids in length. Most preferably, the linker is 11-15 amino acids in length. The linker may have the sequence set forth in SEQ ID NO: 14.

Where the antibody molecule is, or comprises, an scFv, the vascular endothelial growth factor family member may be linked to the N-terminus of the VH domain of the scFv via an amino acid linker or to the C-terminus of the VL domain of the scFv via an amino acid linker.

The conjugate of the present invention may comprise or consist of the sequence shown in SEQ ID NO: 1 or 2. Preferably, the conjugate of the present invention comprises or consist of the sequence shown in SEQ ID NO: 1. The conjugate may have at least 70%, more preferably one of at least 75%, 80%, 85%, 90%, 95%, 96%, 97%, 98%, 99% or 100%, sequence identity to the amino acid sequence shown in SEQ ID NO: 1 or 2, preferably SEQ ID NO: 1.

The conjugate of the present invention may be deglycosylated. Methods for deglycosylating a polypeptide are known in the art and include treatment with Peptide-N-Glycosidase F (PNGase F).

Nucleic Acids

Also provided is an isolated nucleic acid molecule encoding a conjugate according to the present invention. Nucleic acid molecules may comprise DNA and/or RNA and may be partially or wholly synthetic. Reference to a nucleotide sequence as set out herein encompasses a DNA molecule with the specified sequence, and encompasses a RNA molecule with the specified sequence in which U is substituted for T, unless context requires otherwise.

Further provided are constructs in the form of plasmids, vectors (e.g. expression vectors), transcription or expression cassettes which comprise such nucleic acids. Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001) Molecular Cloning: a Laboratory Manual: 3rd edition, Cold Spring Harbor Laboratory Press. Many known techniques and protocols for manipulation of nucleic acid, for example in the preparation of nucleic acid constructs, mutagenesis, sequencing, introduction of DNA into cells and gene expression, and analysis of proteins, are described in detail in Ausubel et al. (1999) 4$^{th}$ eds., Short Protocols in Molecular Biology: A Compendium of Methods from Current Protocols in Molecular Biology, John Wiley & Sons.

Host Cells

A recombinant host cell that comprises one or more constructs as described above is also provided. Suitable host cells include bacteria, mammalian cells, plant cells, filamentous fungi, yeast and baculovirus systems and transgenic plants and animals.

A conjugate according to the present invention may be produced using such a recombinant host cell. The production method may comprise expressing a nucleic acid or construct as described above. Expression may conveniently be achieved by culturing the recombinant host cell under appropriate conditions for production of the conjugate. Following production the conjugate may be isolated and/or purified using any suitable technique, and then used as appropriate. The conjugate may be formulated into a composition including at least one additional component, such as a pharmaceutically acceptable excipient.

Systems for cloning and expression of a polypeptide in a variety of different host cells are well known. The expression of antibodies, including conjugates thereof, in prokaryotic cells is well established in the art. For a review, see for example Plückthun (1991), Bio/Technology 9: 545-551. A common bacterial host is *E. coli*.

Expression in eukaryotic cells in culture is also available to those skilled in the art as an option for production of conjugates for example Chadd et al. (2001), Current Opinion in Biotechnology 12: 188-194); Andersen et al. (2002) Current Opinion in Biotechnology 13: 117; Larrick & Thomas (2001) Current Opinion in Biotechnology 12:411-418. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

A method comprising introducing a nucleic acid or construct disclosed herein into a host cell is also described. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The nucleic acid may or construct be integrated into the genome (e.g. chromosome) of the host cell. Integration may be promoted by inclusion of sequences that promote recombination with the genome, in accordance with standard techniques.

Isolated

This refers to the state in which conjugates of the invention, antibodies for use in the invention, or nucleic acid encoding such conjugates, will generally be in accordance with the present invention. Thus, conjugates of the present invention, antibodies for use in the invention, or nucleic acid encoding such conjugates may be provided in isolated and/or purified, e.g. from the environment in which they are prepared (such as cell culture), in substantially pure or homogeneous form, or, in the case of nucleic acid, free or substantially free of nucleic acid other than the sequence encoding a polypeptide with the required function. Isolated members and isolated nucleic acids will be free or substantially free of material with which they are found in the environment in which they are prepared (e.g. cell culture) when such preparation is by recombinant DNA technology practised in vitro or in vivo. Specific conjugates and nucleic acids may be formulated with diluents or adjuvants and still for practical purposes be isolated—for example the members may be mixed with pharmaceutically acceptable carriers or diluents when used in therapy. Specific conjugates may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations of conjugates may also be used in the invention. For example, such preparations may be mixtures of conjugates comprising antibody molecules with full-length heavy chains and heavy chains lacking the C-terminal lysine, with various degrees of glycosylation and/or with derivatized amino acids, such as cyclization of an N-terminal glutamic acid to form a pyroglutamic acid residue.

Fibronectin

Fibronectin is an antigen subject to alternative splicing, and a number of alternative isoforms of fibronectin are known, including alternatively spliced isoforms A-FN and B-FN, comprising domains ED-A or ED-B respectively, which are known markers of angiogenesis.

Fibronectin Extra Domain-A (ED-A or EDA) is also known as ED, extra type III repeat A (EIIIA) or EDI. ED-A is mainly absent in the plasma form of FN but is abundant during angiogenesis, embryogenesis, tissue remodelling, fibrosis, cardiac transplantation and solid tumour growth. The sequence of human ED-A has been published by Kornblihtt et al. (1984), Nucleic Acids Res. 12, 5853-5868 and Paolella et al. (1988), Nucleic Acids Res. 16, 3545-3557. The sequence of human ED-A is also available on the SwissProt database as amino acids 1631-1720 (Fibronectin type-III 12; extra domain 2) of the amino acid sequence deposited under accession number P02751. The ED-A isoform of fibronectin (A-FN) contains the Extra Domain-A (ED-A). The sequence of the human A-FN can be deduced from the corresponding human fibronectin precursor sequence which is available on the SwissProt database under accession number P02751.

Fibronectin isoform B-FN is one of the best known markers angiogenesis (WO1997/045544, WO2001/62298). An extra domain "ED-B" of 91 amino acids is found in the B-FN isoform and is identical in mouse, rat, rabbit, dog and man. B-FN accumulates around neovascular structures in aggressive tumours and other tissues undergoing angiogenesis, such as the endometrium in the proliferative phase and some ocular structures in pathological conditions, but is otherwise undetectable in normal adult tissues.

Tenascin C

Tenascin-C is a large hexameric glycoprotein of the extracellular matrix which modulates cellular adhesion. It is involved in processes such as cell proliferation and cell migration and is associated with changes in tissue architecture as occurring during morphogenesis and embryogenesis as well as under tumourigenesis or angiogenesis. Several isoforms of tenascin-C can be generated as a result of alternative splicing which may lead to the inclusion of (multiple) domains in the central part of this protein, ranging from domain A1 to domain D (Borsi L et al Int J Cancer 1992; 52:688-692, Carnemolla B et al. Eur J Biochem 1992; 205:561-567, WO2006/050834).

Inflammatory Diseases and/or Disorders

"Inflammatory disease and/or disorder" refers to disease and/or disorders which are accompanied and/or characterised by inflammation. An inflammatory disease and/or disorder is preferably associated with and/or characterised by angiogenesis and/or lymphangiogenesis. An inflammatory disease and/or disorder may be an inflammatory disease and/or disorder characterised by angiogenesis and/or lymphangiogenesis, wherein the neovasculature expresses the ED-A isoform of fibronectin, the ED-B isoform of fibronectin and/or tenascin C.

The conjugate for use in the treatment of an inflammatory disease and/or disorder, or delivery of the vascular endothelial growth factor family member to sites of an inflammatory disease and/or disorder in a patient, may be selected based on the expression of the ED-A isoform of fibronectin, ED-B isoform of fibronectin and/or tenascin C in said inflammatory disease and/or disorder.

The inflammatory disease or disorder may be an acute or a chronic inflammatory disease or disorder.

In a preferred embodiment, the inflammatory disease and/or disorder is selected from the group consisting of: atherosclerosis, inflammatory bowel disease, such as Crohn's disease or ulcerative colitis, psoriasis, chronic airway inflammation, atopic dermatitis, rheumatoid arthritis, lymphedema, glaucoma, macular degeneration, and myocardial infarction. For example, the disease may be a disease associated with chronic skin inflammation, such as psoriasis or atopic dermatitis. In a more preferred embodiment, the disease is psoriasis or atopic dermatitis. In an alternative more preferred embodiment, the disease is atherosclerosis. In a further alternative more preferred embodiment, the disease is inflammatory bowel disease. The inflammatory bowel disease is preferably Crohn's disease or ulcerative colitis.

Treatment

It is expected that the conjugates of the invention will have anti-inflammatory activity and thus find application in the treatment (which may include prophylactic treatment) of inflammatory diseases and/or disorders. Without being limited by theory, it is expected that the conjugates of the invention will show potent anti-inflammatory activity as a result of targeting the vascular endothelial growth factor family member to sites of angiogenesis in inflammatory diseases and disorders, as demonstrated in the examples.

The conjugate may be in form of a pharmaceutical composition. The pharmaceutical composition typically comprises a therapeutically effective amount of the conjugate and optionally auxiliary substances such as pharmaceutically acceptable excipient(s). Pharmaceutical compositions are prepared in a manner well known in the pharmaceutical art. A carrier or excipient may be a liquid material which can serve as a vehicle or medium for the active ingredient. Suitable carriers or excipients are well known in the art and include, for example, stabilisers, antioxidants, pH-regulating substances, controlled-release excipients. The pharmaceutical composition may be adapted, for example, for parenteral use and may be administered to the patient in the form of solutions or the like.

Pharmaceutical compositions comprising a conjugate of the invention may be administered to a patient. Administration is preferably in a "therapeutically effective amount", this being sufficient to show benefit to the patient. Such benefit may be amelioration of at least one symptom. The actual amount administered, and rate and time-course of administration, will depend on the nature and severity of what is being treated. Prescription of treatment, e.g. decisions on dosage etc., is within the responsibility of general practitioners and other medical doctors. Treatments may be repeated at daily, twice-weekly, weekly, or monthly intervals at the discretion of the physician.

A pharmaceutical composition may be administered to a patient in need of treatment via any suitable route, usually by injection into the bloodstream and/or directly into the site to be treated. The precise dose and its frequency of administration will depend upon a number of factors, the route of treatment, the size and location of the area to be treated. Preferably, the conjugate of the present invention is administered intravenously.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the pharmaceutical composition will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A conjugate according to the present invention may be administered alone or in combination with other treatments, concurrently or sequentially or as a combined preparation with another therapeutic agent or agents, for the treatment of inflammatory disease or disorder. For example, a conjugate of the invention may be used in combination with an existing therapeutic agent for the inflammatory disease or disorder in question. In the treatment of atherosclerosis, a conjugate of the invention may be administered in combination with a statin.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1—Production of the F8-VEGF-C, F8-VEGF-C156Ser, and KSF-VEGF-C Fusion Proteins Materials and Methods
Cloning of Fusion Protein F8-VEGF-C The genes encoding F8 and ΔNΔCVEGF-C (Joukov V, Kumar V, Sorsa T, Arighi E, Weich H, Saksela O, and Alitalo K. *A recombinant mutant vascular endothelial growth factor-C that has lost vascular endothelial growth factor receptor-2 binding, activation, and vascular permeability activities. J Biol Chem.* 1998; 273(12):6599-6602) were amplified and PCR assembled. The product was digested using HindIII/NotI and cloned into an identically digested pcDNA3.1(+) plasmid backbone (Invitrogen).

Cloning of Fusion Protein F8-VEGF-C156Ser

The genes encoding F8 and ΔNΔCVEGF-C156Ser (Joukov V, Kumar V, Sorsa T, Arighi E, Weich H, Saksela 0, and Alitalo K. A recombinant mutant vascular endothelial growth factor-C that has lost vascular endothelial growth factor receptor-2 binding, activation, and vascular permeability activities. J Biol Chem. 1998; 273(12):6599-6602) were amplified and PCR assembled. The product was digested using HindIII/NotI and cloned into an identically digested pcDNA3.1(+) plasmid backbone.

Cloning of Fusion Protein KSF-VEGF-C

The genes encoding the antibody KSF (specific to hen egg lysozyme) and ΔNΔCVEGF-C were amplified and PCR assembled. The product was digested using HindIII/NotI and cloned into an identically digested pcDNA3.1(+) plasmid backbone.

Expression of Fusion Proteins

The fusion protein was expressed in CHO-S cells using transient gene expression. Briefly, CHO cells were cultured in suspension in PowerCHO-2CD medium (Lonza), supplemented with HT supplement containing 100 μM hypoxanthine and 16 μM thymidine (Lonza) and 2 mM L-Glutamine (Life Technologies). For transfection, cells were transferred into ProCHO-4 medium (Lonza), supplemented with HT supplement containing 100 μM hypoxanthine and 16 μM thymidine (Lonza) and 2 mM L-glutamine (Life Technologies) and plasmid premixed with polethylenimine (PEI) was added (DNA:PEI ratio of 1:4). Cells were incubated at 37° C. and PowerCHO-2CD was added 1:1 approx. 3-4 hours after transfection. 24 hours later, incubation temperature was lowered to 32° C. and cells were cultured for 5-7 days at an initial cell density of $1 \times 10^6$ cells per ml.

In the case of F8-VEGF-C and F8-VEGF-C156Ser, stably transfected monoclonal cell lines were established using serial dilution of transiently transfected CHO-S cells kept under Geneticin (Life Technologies) selection for >28 days.

In the case of KSF-VEGF-C, stably transfected monoclonal cell lines were established by electroporation (Nucleofector V kit, Lonza, used according to manufacturer's instructions) followed by G-418 (0.8 mg/ml, Roche) selection for >28 days and fluorescence-activated cell sorting of cells stained with rabbit anti-human IgG (A0423, Dako) and Alexa 488-conjugated goat anti-rabbit secondary antibody (Invitrogen) on a FACSAria Ilu (BD Biosciences) using FACSDiva software.

Purification of Fusion Protein

The fusion protein was purified by protein A affinity chromatography (HiTrap Protein A HP, GE Healthcare Life Sciences).

SDS-PAGE and Western Blot Analysis

The fusion protein was analysed by SDS-PAGE (Nu-PAGE system, Life Technologies). Proteins were transferred to polyvinylidene difluoride (PVDF) membranes (Invitrogen), which were then blocked with 5% milk and incubated with polyclonal rabbit anti-VEGF-C antibody (ab9546, Abcam) followed by HRP-conjugated secondary antibody (donkey ECL anti-rabbit IgG, HRP-linked F(ab')$_2$ fragment, GE Healthcare). Signals were visualized by chemiluminescence (ECL Prime, Amersham) on an Agfa Curix 60 developer.

For VEGFR3 phosphorylation analysis, PAE cells were stimulated for 20 minutes with VEGF-C (200 ng/ml), VEGF-C156Ser (200 ng/ml), F8-VEGF-C (corresponding to 200 ng/ml VEGF-C) and F8-VEGF-C156Ser (corresponding to 200 ng/ml VEGF-C156Ser) and then lysed in RIPA buffer: 50 mM Tris-HCl (pH 7.5), 150 mM NaCl, 0.5% NP-40, 5 mM EDTA, 1% Triton-X100 and 1 mM Na$_3$VO$_4$. VEGFR-3 was immunoprecipitated by using Dynabeads Protein G (Invitrogen) complexed with anti-VEGFR-3 antibody (C20, Santa Cruz Biotechnology). The immunoprecipitated samples were subjected to SDS-PAGE and analyzed for phosphorylation by using an anti-phosphotyrosine antibody (4G10, Milipore). Finally, the membrane was stripped for 30 min in stripping-buffer containing Tris, SDS and 2-mercaptoethanol and reprobed with VEGFR-3 antibody (C20, Santa Cruz Biotechnology) to analyze total VEGFR-3. To investigate VEGFR-2 phosphorylation, human LEC were stimulated and lysed as described above. Cell lysates were subjected to SDS-PAGE and phosphorylation was investigated using a rabbit anti-human (p1175) VEGFR-2 antibody (Cell Signaling). Following stripping, the membrane was reprobed with anti-human VEGFR-2 antibody (Cell Signaling).

Size Exclusion Chromatography of Fusion Protein

Purified fusion protein was analysed by size exclusion chromatography on a Superdex200 10/300GL column (GE Healthcare).

Results

The Coomassie brilliant blue stainings of F8-VEGF-C (left) and KSF-VEGF-C (right) revealed the proteins to be mainly present as dimers under non-reducing conditions (FIG. 1A).

Figure 1C:
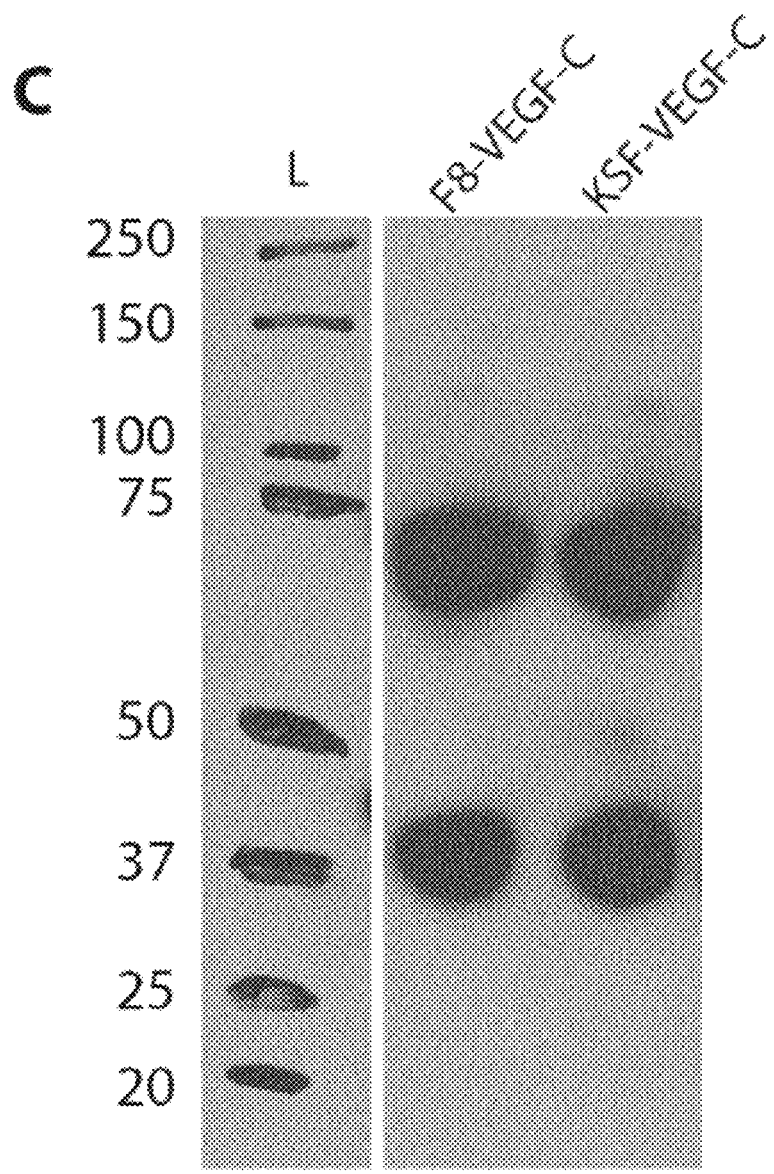

The western blotting analysis showed that F8-VEGF-C and KSF-VEGF-C were recognized by an anti-VEGF-C antibody (FIG. 1C).

The size-exclusion chromatograms of F8-VEGF-C (top) and KSF-VEGF-C (bottom) confirmed the purity and dimeric form of the fusion proteins (FIG. 1B).

Example 2—Biological Activity of F8-VEGF-C and KSF-VEGF-C In Vitro and In Vivo Materials and Methods For proliferation assays, 2500 human lymphatic endothelial cells (LECs) were seeded into collagen-coated 96-well plates in EBM medium (Lonza) containing 20% FBS (Gibco), 25 μg/ml cAMP (Sigma) and 10 μg/ml hydrocortisone (Sigma). After an overnight starvation in EBM containing 0.5% FBS, the cells were incubated with VEGF-A (20 ng/ml, Cell Sciences), VEGF-C (200 ng/ml, kind gift of Dr. Kurt Ballmer-Hofer, Villingen, Switzerland), F8-SIP (400 ng/ml), F8-VEGF-C (600 ng/ml) or F8-VEGF-C156Ser (600 ng/ml). After 72 hours, 100 µg/ml 4-methylumbelliferyl heptanoate (MUH, Sigma) were added and the fluorescence intensity, corresponding to the number of viable cells was measured on a SpectraMax reader (Molecular Devices) at 355 nm excitation and 460 nm emission (Detmar et al. "*Cytokine regulation of proliferation and ICAM-1 expression of human dermal microvascular endothelial cells in vitro*", *J Invest Dermatol.* 1992, 98:147-53). For each condition, at least quintuplicates were analyzed and the assay was performed three times.

To analyze the influence of the F8-VEGF-C constructs on migration, porcine aortic endothelial (PAE) cells (a kind gift of Dr. Lena Claesson-Welsh) which overexpress VEGFR-3 (Waltenberger J, Claesson-Welsh L et al. "*Different signal transduction properties of KDR and Flt1, two receptors for vascular endothelial growth factor*", *J Biol Chem.* 1994, 269:26988-95) were starved overnight in DMEM medium (Gibco) containing 0.5% FBS. The lower side of the transwell (8 µm pores, Costar) was coated with fibronectin (10 µg/ml) followed by blocking with 100 µg/ml BSA, each for one hour. 30,000 cells were seeded in starvation medium on the transwell and 500 µl media containing VEGF-A, VEGF-C, F8-diabody, F8-VEGF-C or F8-VEGF-C156Ser (same concentrations as used for proliferation assays) were added into the lower well. After 3 hours, non-migrated cells on the upper side of the transwell were removed using cotton swabs. To analyze the migrated cells, the inserts were stained with Hoechst 33342 (Life Technologies) and five images per transwell were taken to determine the number of migrated cells using ImageJ (http://imagej.nih.gov/ij). For each condition, quadruplicates were analyzed and the assay was performed twice.

The 3-dimensional sprouting assay was performed as described previously (Schulz et al. "*Phenotype-based high-content chemical library screening identifies statins as inhibitors of in vivo lymphangiogenesis*", *Proc Natl Acad Sci USA.* 2012, 109: E2665-74). Briefly, LEC-coated cytodextran microcarrier beads (Sigma-Aldrich) were labelled with cell tracker green (CTG, Invitrogen) and embedded in collagen type I hydrogels (1 mg/ml, Advanced Bio-Matrix), followed by the addition of LEC medium (EBM, 20% FBS and 40 ng/ml bFGF (R&D Systems)). VEGF-A (40 ng/ml), VEGF-C (200 ng/ml), VEGF-C156Ser (200 ng/ml), F8-VEGF-C (corresponding to 200 ng/ml VEGF-C), F8-VEGF-C156Ser (corresponding to 200 ng/ml VEGF-C156Ser) or F8 diabody were added to the medium. After 24 h at 37° C., imaging was conducted and sprouts were counted manually. For each condition, quintuplicates were analyzed and the assay was performed twice.

In order to study the effects of F8-VEGF-C and KSF-VEGF-C on lymphatic vessels in the diaphragm, FVB mouse pups received daily intraperitoneal injections of either F8-VEGF-C (2.27 µg/g body weight), KSF-VEGF-C (2.27 µg/g body weight) or PBS on days P1-P5. Mice were euthanized on P6, diaphragms excised and fixed in 4% PFA for 2 h, followed by blocking in 5% donkey serum, 0.1% Triton-X, 0.05% NaN3 and 1% BSA in PBS for 1 h. The samples were then incubated with primary antibodies overnight at 4° C. Primary antibodies used were polyclonal rabbit anti-mouse LYVE-1 (Angiobio) and rat anti-mouse CD31 (MEC13.3, BD Pharmingen). Alexa 488- and 594-conjugated secondary antibodies were purchased from Invitrogen. Stained samples were flat-mounted on glass slides and Z-stack images were acquired with a Zeiss LSM 710-FCS confocal microscope (Carl Zeiss) equipped with a 10×0.3NA EC Plan-Neofluar objective, using the Zeiss ZEN 2009 software.

Results

The proliferation assays using human LECs revealed that addition of F8-VEGF-C or KSF-VEGF-C significantly increased proliferation compared to starvation medium and the SIP protein control. The effect was comparable to free VEGF-C (FIG. 2A).

Figure 2:
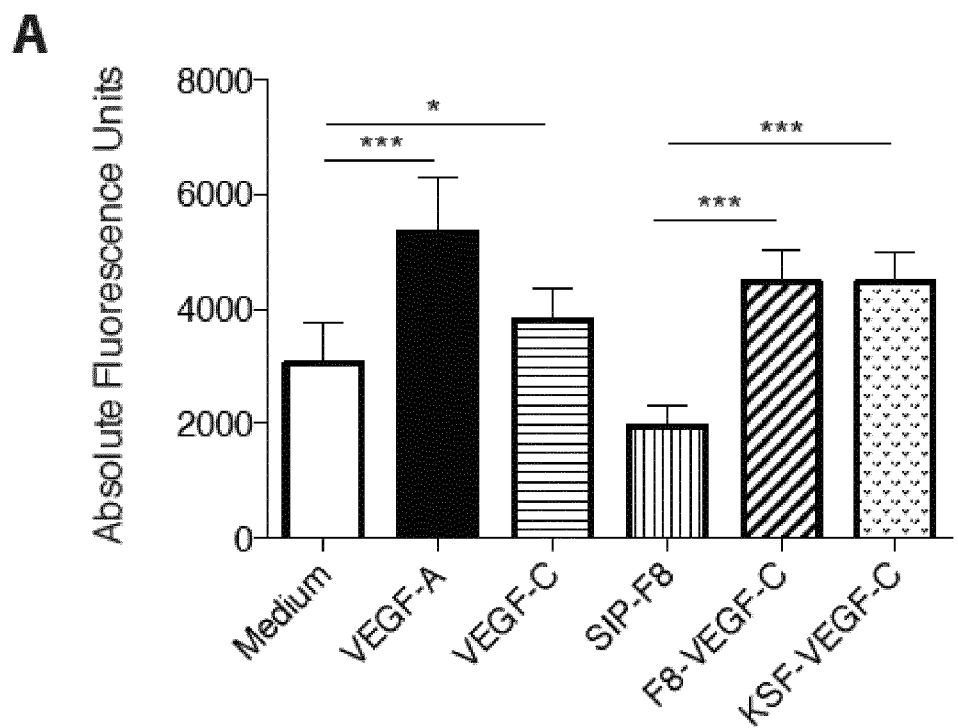
FIG. 2: Biological activity of F8-VEGF-C and KSF-VEGF-C in vitro and in vivo. (A) Proliferation assays of human lymphatic endothelial cells (LECs) revealed that addition of F8-VEGF-C or KSF-VEGF-C significantly increased proliferation compared to starvation medium and SIP protein control (SIP-F8); the effect is comparable to free VEGF-C. (B) Daily intraperitoneal injections of F8-VEGF-C and KSF-VEGF-C on days P1 to P5 significantly increased lymphangiogenesis in the diaphragm muscle of FVB mouse pups compared to PBS. (C) F8-VEGF-C and the VEGFR3-specific mutant form, F8-VEGF-C156Ser, significantly increase sprout formation of LECs coated on microcarrier beads. (D) F8-VEGF-C caused a considerable increase in the migration of porcine aortic endothelial (PAE) cells overexpressing VEGFR3 in transwell assays. Scale bar, 100 μm. Data represent mean±SD. *P<0.05, ***P<0.001.
Figure 2:
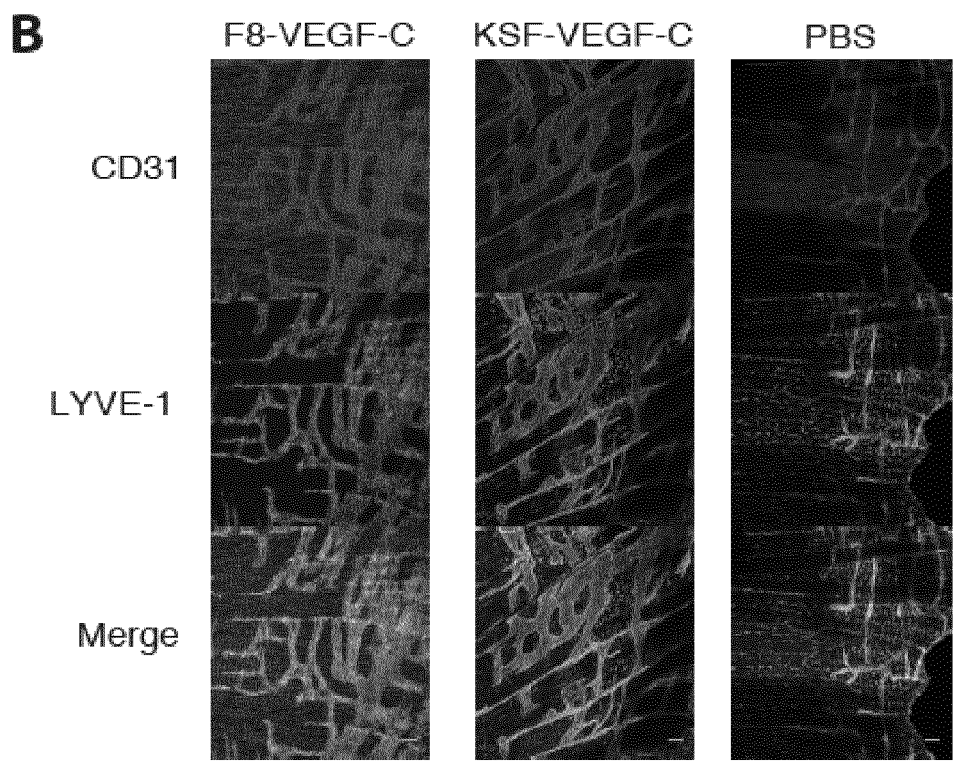
Figure 2:
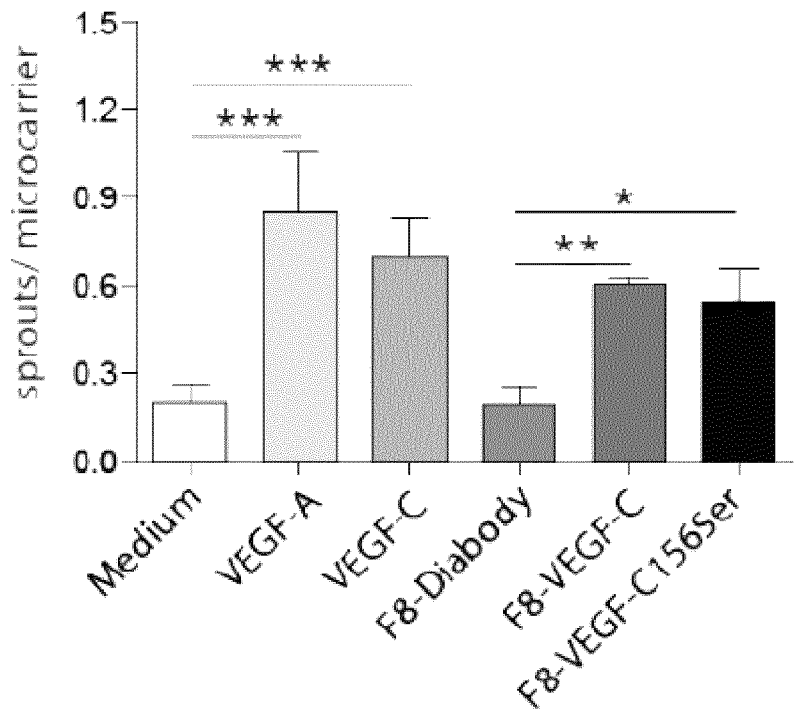
Figure 2:
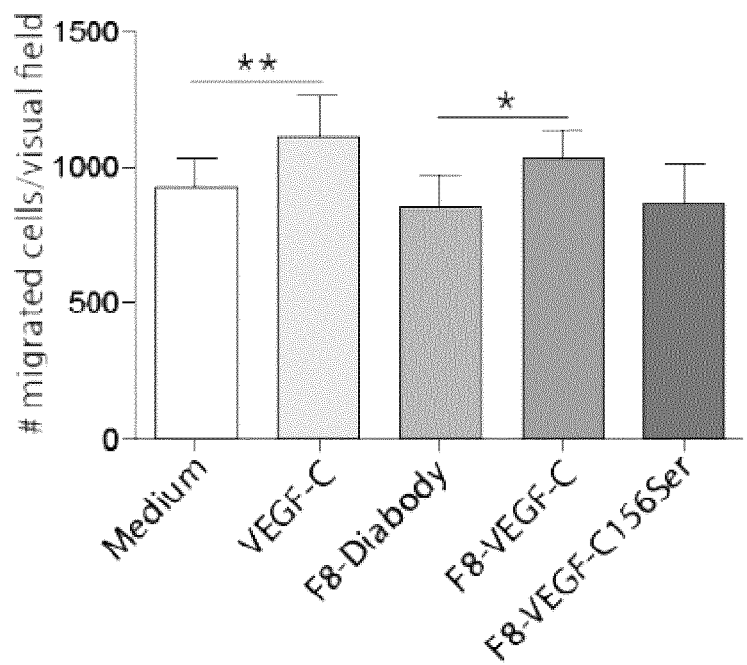

Daily intraperitoneal injections of F8-VEGF-C and KSF-VEGF-C from days P1 to P5 significantly increased lymphangiogenesis in the diaphragm muscle compared to PBS, demonstrating that the fusion proteins are biologically active (FIG. 2B).

F8-VEGF-C and the VEGFR3-specific mutant form F8-VEGF-C156Ser significantly increase sprout formation of LECs coated on microcarrier beads (FIG. 2C).

F8-VEGF-C caused a considerable increase in the migration of porcine aortic endothelial (PAE) cells overexpressing VEGFR3 in transwell assays (FIG. 2D). No significant increase in migration of the PAE cells was observed after treatment with the VEGFR3-specific mutant form F8-VEGF-C156Ser. Without wishing to be bound by theory, one possible explanation is that migration is mediated—at least in part—via signalling by VEGFR2, which is not activated by F8-VEGF-C156Ser. Indeed, it has been shown by receptor-specific blockade that activation of both VEGFR2 and VEGFR3 is required for migration of human LECs in an apparently additive manner (Goldmann et al. "Cooperative and redundant roles of VEGFR-2 and VEGFR-3 signaling in adult lymphangiogenesis", FASEB J. 2007, 21(4); 1003-12), which is in line with the results presented here.

These results clearly show that VEGF-C and VEGF-C156Ser in the constructs remained biologically active in vitro and in vivo following the fusion of VEGF-C or VEGF-C156Ser to the targeting moieties. Moreover, the biological activity of the constructs was comparable to free VEGF-C.

Example 3—Effect of F8-VEGF-C on Cell Populations

Materials and Methods

Ears were harvested from K14-VEGF-A transgenic mice on day 15 or 16 after challenge as described in Example 4 below. Following mechanical disruption of the tissue, samples were digested under rotation in DMEM (Gibco) containing 4 mg/ml of collagenase IV (Gibco) at 37° C. for 45 min. Samples were filtered through 40 µm strainers (Falcon), centrifuged and resuspended in FACS buffer containing 2% FBS (Gibco) and 2 mM EDTA (Fluka). Samples were incubated with anti-mouse CD16/32 antibody (93, Biolegend) on ice for 20 min and subsequently stained on ice for 30 min using Pacific Blue anti-mouse CD45 (30-F11, Biolegend), APC anti-mouse CD4 (GK1.5, Biolegend), FITC anti-mouse CD8 (53-6.7, Biolegend), PerCP-eFluor 710 anti-mouse gamma delta TCR (GL-3, eBioscience), or Brilliant Violet anti-mouse CD25 (PC61, Biolegend) antibodies and live/dead fixable aqua dye (Life Technologies). Staining for Foxp3 was performed using the anti-mouse/rat Foxp3 staining set PE (eBioscience) according to manufacturer's instructions. Samples were acquired on an LSR-Fortessa (BD Biosciences) using FACSDiva software. Analysis was performed using FlowJo v10.1. Quantification of absolute cell numbers was done using AccuCheck counting beads (Invitrogen).

Results

Figure 3:
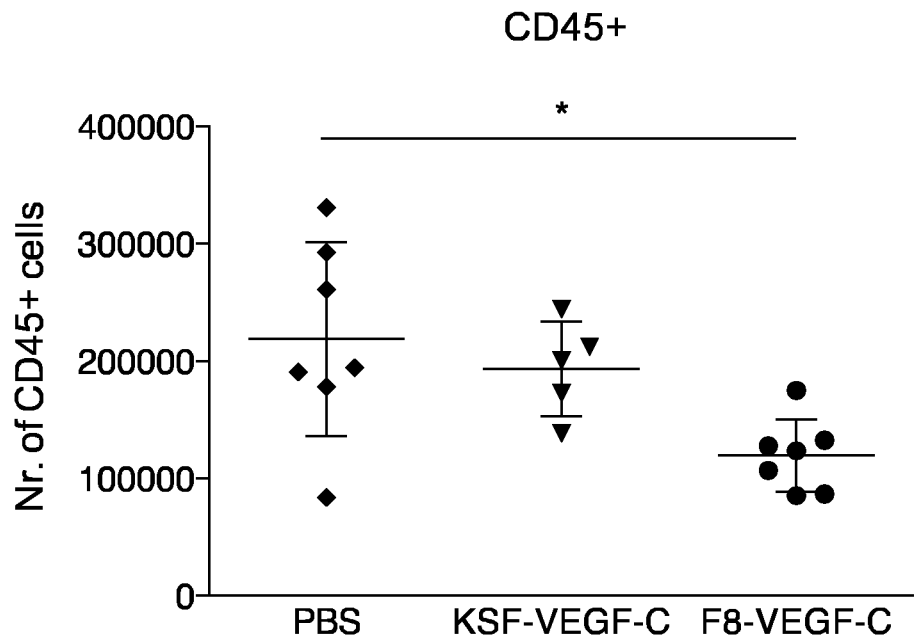
FIG. 3: F8-VEGF-C reduces numbers of leukocytes and T cell subsets. FACS analysis revealed that treatment with F8-VEGF-C reduced absolute numbers of (A) leukocytes, (B) regulatory T cells, (C) γδ T cells and (D) CD4 T cells compared with the PBS and KSF-VEGF-C controls. Data represent mean±SD. *P<0.05. These results are in-line with the results shown in FIG. 5 based on stained ear sections.
Figure 3:
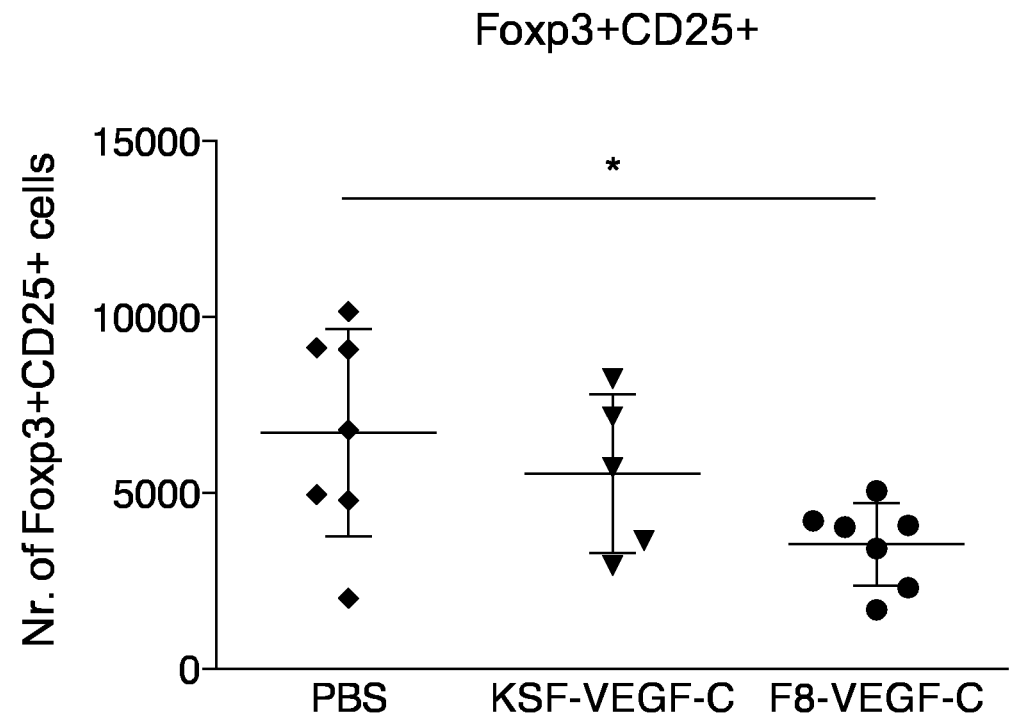
Figure 3:
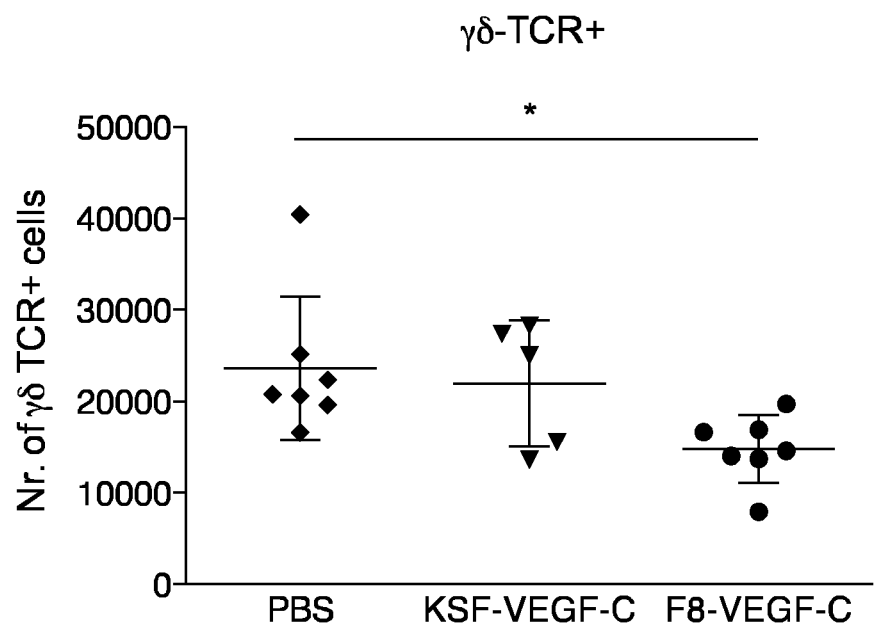
Figure 3:
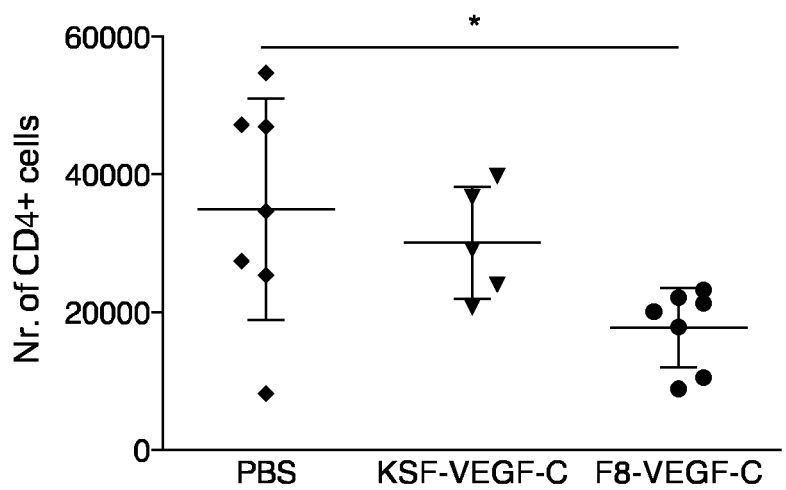

The F8-VEGF-C fusion protein reduced the number of leukocytes and T cell subsets. Specifically, FACS analysis revealed that treatment with F8-VEGF-C reduced the absolute numbers of leukocytes (FIG. 3A), regulatory T cells (FIG. 3B), γδ T cells (FIG. 3C) and (D) CD4 T cells (FIG. 3D) compared with treatment with the untargeted KSF-VEGF-C control antibody.

The fact that targeted treatment with F8-VEGF-C compared to untargeted treatment with KSF-VEGF-C or treatment with PBS notably reduced cell populations vitally important for the inflammatory response, provides strong evidence for the anti-inflammatory effectiveness of F8-VEGF-C and the importance of targeted delivery of VEGF-C.

Example 4—Effects of F8-VEGF-C and F8-VEGF-C156Ser on Chronic Skin Inflammation

Materials and Methods
Preparation of Mouse Models of Chronic Skin Inflammation

The mice used in this study were bred and housed in the animal facility of ETH Zurich. Experiments were performed in accordance with animal protocols 117/2011 and 37/2013 approved by the local veterinary authorities (Kantonales Veterinaramt Zürich). K14-VEGF-A transgenic mice have been described previously (Detmar et al. "*Increased microvascular density and enhanced leukocyte rolling and adhesion in the skin of VEGF transgenic mice*", J Invest Dermatol. 1998, 111:1-6, Xia et al. "*Transgenic delivery of VEGF to mouse skin leads to an inflammatory condition resembling human psoriasis*", Blood. 2003, 102:161-8). Briefly, sensitization by a topical application of a 2% oxazolone solution (4-ethoxymethylene-2 phenyl-2-oxazoline-5-one; Sigma-Aldrich) in acetone/olive oil (4:1 vol/vol) on the shaved abdomen (50 μl) and to each paw (5 μl), followed by a topical application of 10 μl oxazolone (1%) on each side of both ears five days later (challenge), leads to a chronic skin inflammation in these mice (Kunstfeld et al. "*Induction of cutaneous delayed-type hypersensitivity reactions in VEGF-A transgenic mice results in chronic skin inflammation associated with persistent lymphatic hyperplasia*", Blood. 2004, 104:1048-57). Ear thickness was measured before and repeatedly after challenge using calipers. Starting on day 7, the following treatments were applied i.v. every second day, until day 13 (2 days before termination): PBS, SIP-F8 (Villa et al., 2008), TNFR-Fc (Doll et al., 2013), F8-VEGF-C, F8-VEGF-C156Ser or KSF-VEGF-C (50 μg of each construct). On day 15, the mice were analyzed (FIGS. 4A-4C and FIG. 5).

In a second model of chronic skin inflammation, an imiquimod-containing cream (Aldara, 3M Pharmaceuticals) was applied daily to the ear skin of C57BL/6 wild-type mice (at least 5 per group) for 5 consecutive days, followed by one day without treatment and another imiquimod dose on day 7. Starting on day 7, each mouse received every second day an i.v. injection of either PBS, SIP-F8, TNFR-Fc, F8-VEGF-C, F8-VEGF-C156Ser or KSF-VEGF-C, with the last injection on day 11. Ear thickness was measured daily. The mice were analyzed on day 12 or 13 (FIGS. 4D-4F and FIG. 7).

TNFR-Fc was included as a comparison in these experiments as it is one of the standard therapies for chronic inflammatory diseases such as psoriasis and rheumatoid arthritis.

Immunofluorescence

OCT embedded ear samples of K14-VEGF-A transgenic and imiquimod-treated mice were frozen on liquid nitrogen and 7 μm cryostat sections were prepared. After fixation in acetone and rehydration in 80% methanol, the sections were blocked with PBS containing 5% donkey serum, 0.1% Triton-X, 0.05% NaN3 and 1% bovine serum albumin, followed by incubation with the respective primary antibodies. Standard H&E and immunofluorescence stainings were performed as described previously (Huggenberger et al., 2010; Kunstfeld et al., 2004), using the following antibodies: biotinylated F8, polyclonal rabbit anti-mouse LYVE-1 (Angiobio), rat anti-mouse CD31 (MEC13.3, BD Pharmingen, rat anti-mouse MECA-32 (BD Biosciences), rat anti-mouse CD68 (FA-11, abcam) and rat anti-mouse CD4 (GK1.5, eBioscience) antibodies. Alexa 488- and Alexa 594-conjugated secondary antibodies and Hoechst 33342 were purchased from Invitrogen. Slides were mounted with mowiol mounting medium and imaged on an Axioskop2 mot plus microscope (Zeiss).

For H&E stainings, sections were incubated with hematoxylin solution according to Gill III (Merck), washed with water and 0.1% hydrochloric acid and stained with 0.5% aqueous eosin Y (Merck) before being mounted using Eukitt mounting medium (Sigma-Aldrich).

Results
First Model of Chronic Skin Inflammation: The CHS-Induced Skin Inflammation (i) The effect of F8-VEGF-C on ear thickness and lymphatic vessels in the CHS-induced skin inflammation mouse model of chronic skin inflammation was evaluated. F8-VEGF-C but not KSF-VEGF-C was shown to alleviate chronic skin inflammation.

Figure 4:
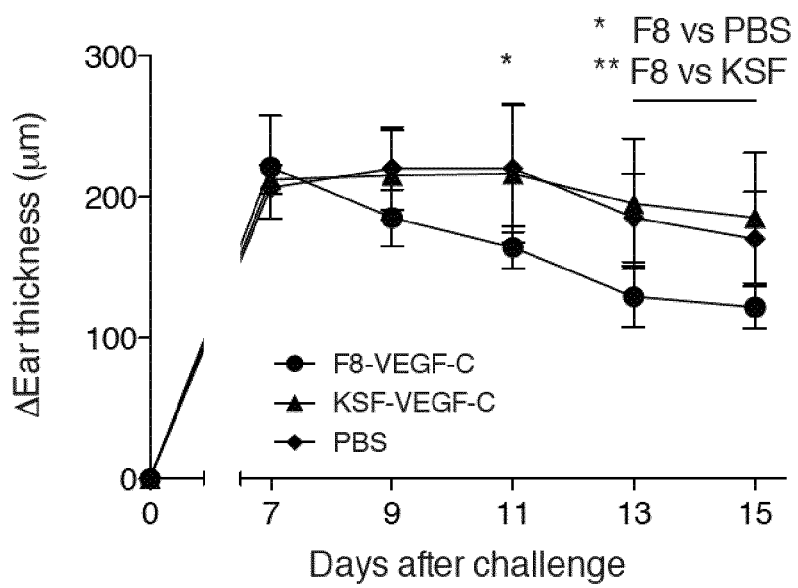
FIG. 4: F8-VEGF-C but not KSF-VEGF-C alleviates chronic skin inflammation. (A) Ear thickness of K14-VEGF-A mice subjected to CHS-induced skin inflammation. Animals received intravenous (i.v.) injections of F8-VEGF-C, KSF-VEGF-C or PBS on days 7, 9 11 and 13 after challenge. F8-VEGF-C but not controls KSF-VEGF-C or PBS reduced ear oedema. (B) Staining of frozen K14-VEGF-A ear sections for lymphatic (LYVE-1, green) vessels. (C) Quantification of stained K14-VEGF-A ear sections revealed that treatment with F8-VEGF-C increased the lymphatic vessel area compared with the KSF-VEGF-C and PBS controls. (D) Ear thickness of C57Bl/6 mice. Imiquimod-containing cream was applied daily on days 1-5 and on day 7. Mice received i.v. injections of F8-VEGF-C, KSF-VEGF-C or SIP-F8 on days 7, 9 and 11. F8-VEGF-C but not KSF-VEGF-C or SIP-F8 accelerated oedema resolution. (E) LYVE-1 staining of frozen ear sections of animals that underwent imiquimod-induced inflammation. (F) Quantification of LYVE-1 stained ear tissue showed that treatment with F8-VEGF-C increased lymphatic vessel area compared to KSF-VEGF-C or SIP-F8. Scale bar, 100 μm. Data represent mean±SD. *P<0.05, P<0.01, *P<0.001.
Figure 4:
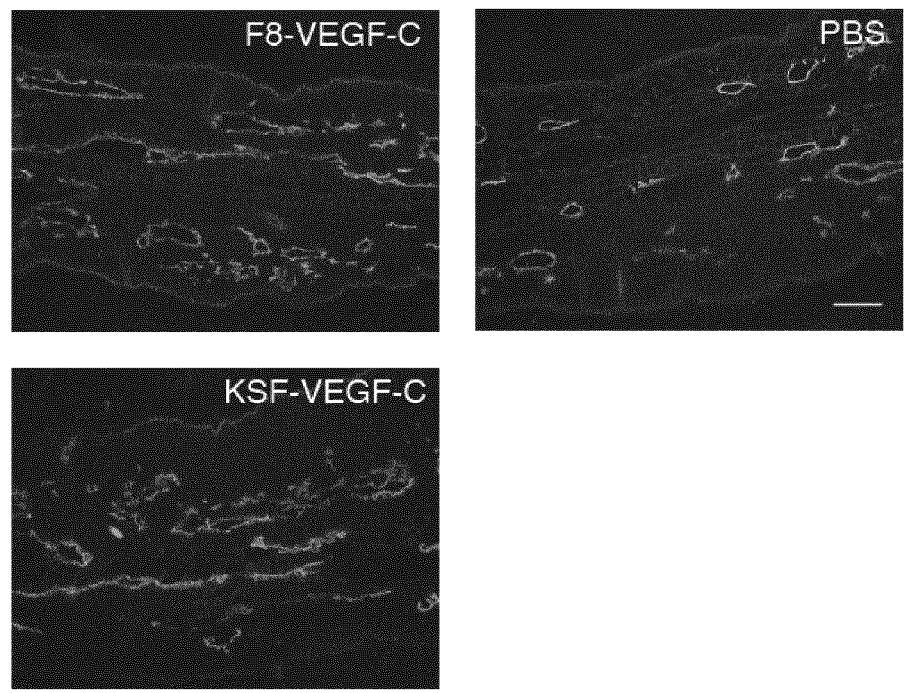
Figure 4:
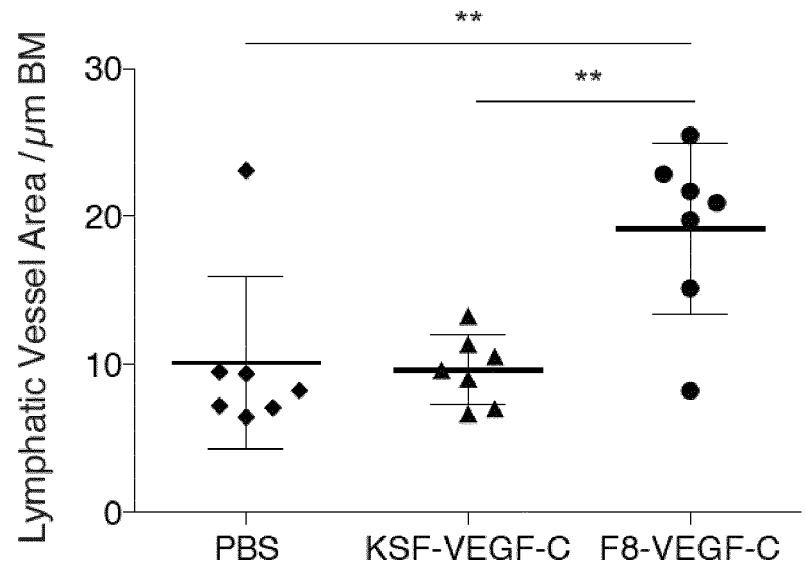
Figure 4:
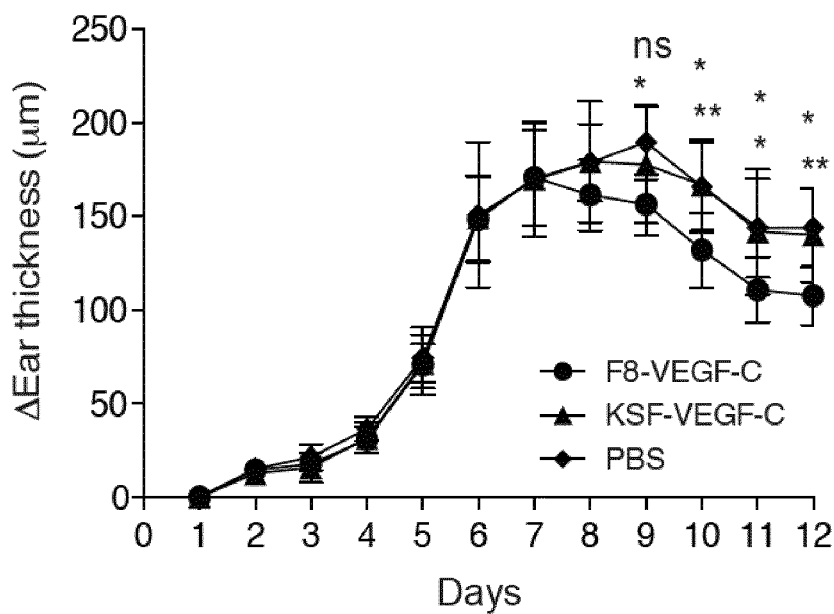
Figure 4:
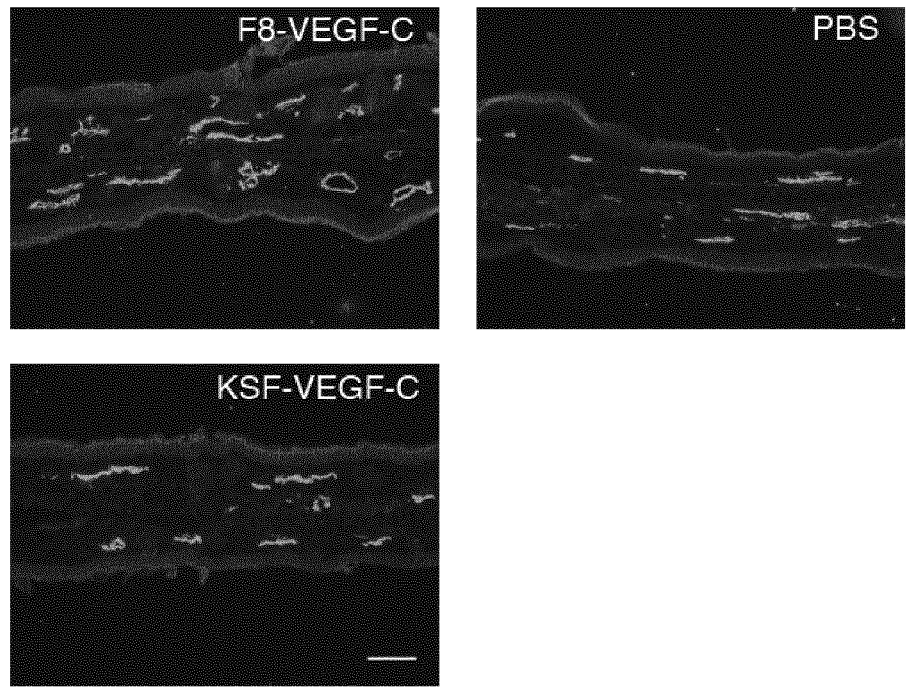
Figure 4:
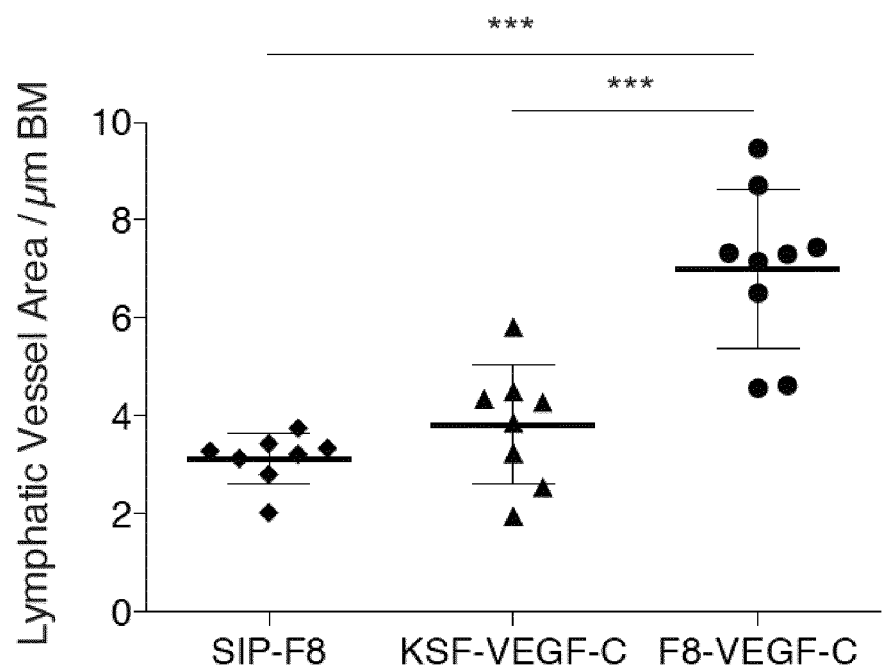
Figure 5:
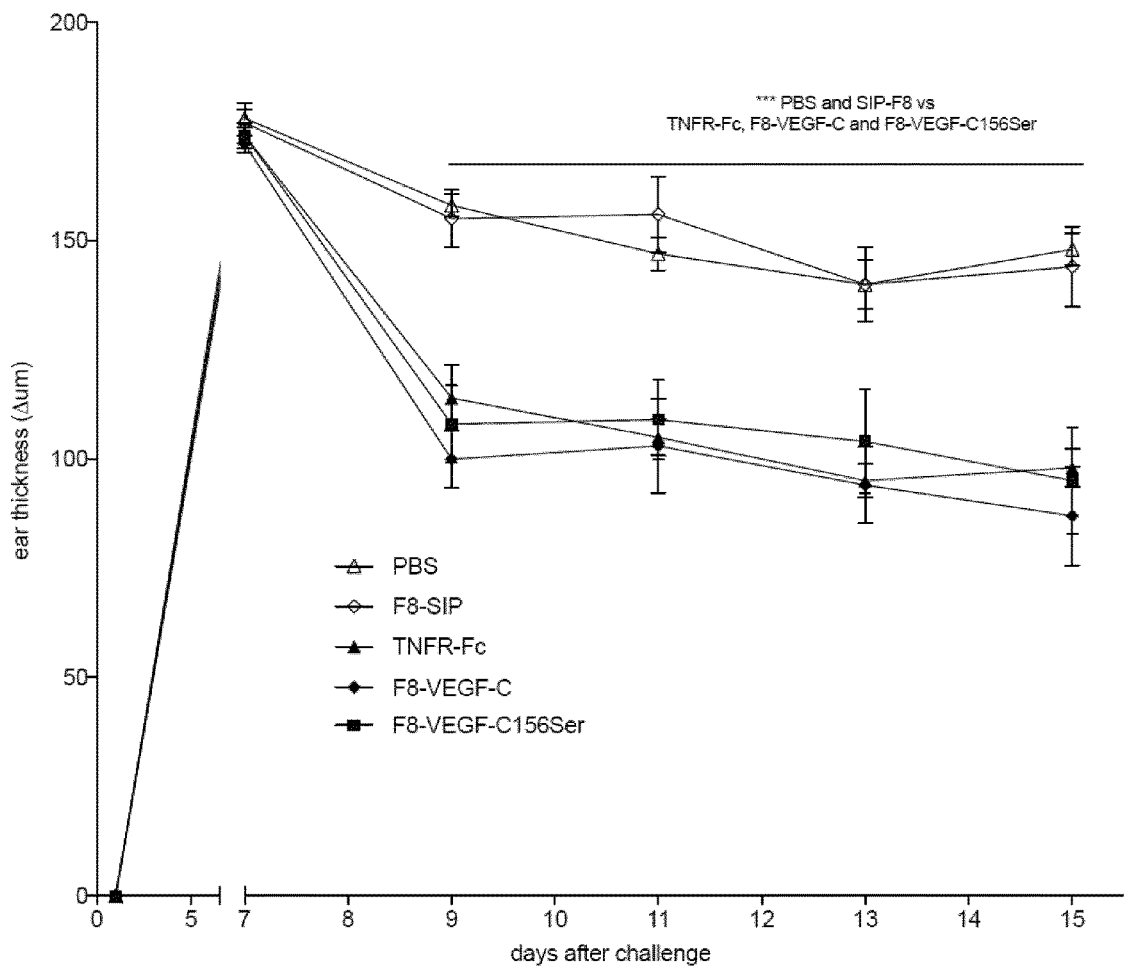
FIG. 5: F8-VEGF-C and F8-VEGF-C156Ser but not SIP-F8 inhibit skin inflammation to a degree comparable with TNFR-Fc in CHS-induced skin inflammation. (A) CHS-induced skin inflammation was induced in hemizygous K14-VEGF-A transgenic mice (n=5 per group). Treatment with F8-VEGF-C or F8-VEGF-C156Ser from day 7 onwards, every second day, significantly reduced inflammatory ear swelling as compared to SIP-F8 and had a similar effect as TNFR-Fc. Data represent mean±SEM. (B, C) Immunofluorescence stains and quantitative image analysis of inflamed K14-VEGF-A tg ear skin for LYVE-1 and MECA-32 revealed a significantly increased LYVE-1 positive lymphatic area in the F8-VEGF-C and F8-VEGF-C156Ser treatment groups. Scale bar represents 100 μm. (D, E) Immunofluorescence stains for LYVE-1 and quantitative image analysis showed an increased lymphatic vessel network in F8-VEGF-C- and F8-VEGF-C156Ser-treated mice. Scale bar represents 500 µm. (F, G) Immunofluorescence stains of inflamed ear skin for CD4 and quantitative image analysis revealed that F8-VEGF-C, F8-VEGF-C156Ser and TNFR-Fc treatment reduced the infiltration with CD4+ T cells as compared to PBS and SIP-F8. Scale bar represents 100 µm. Data represent mean±SD. *P<0.05; ***P<0.001.
Figure 5:
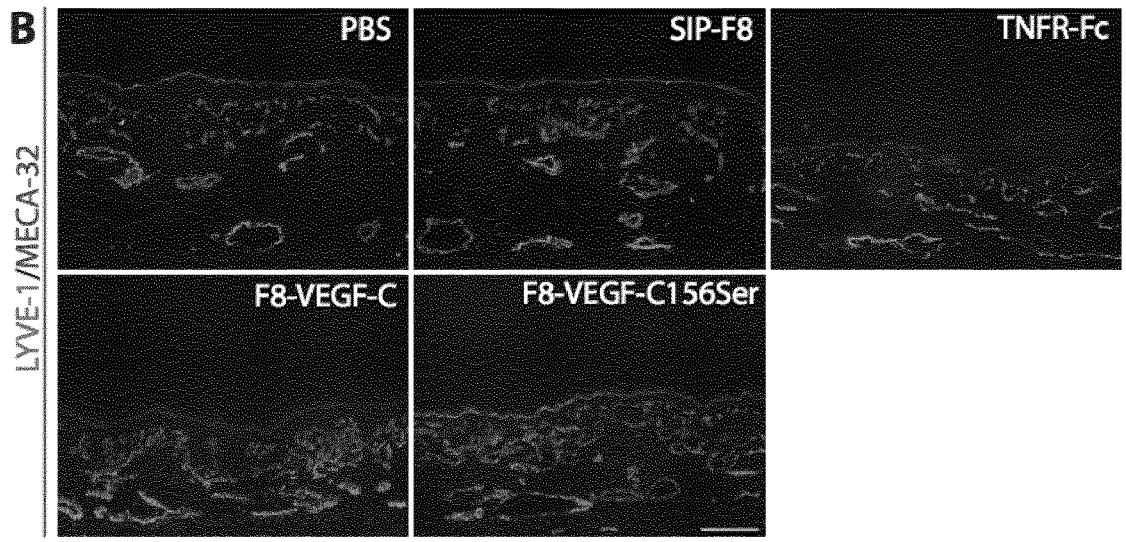
Figure 5:
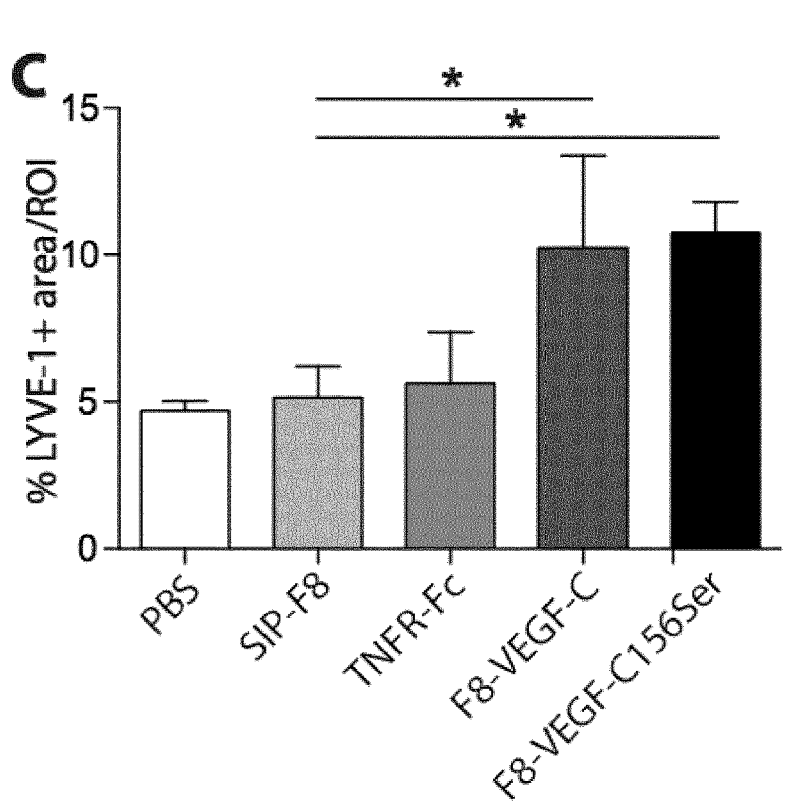
Figure 5:
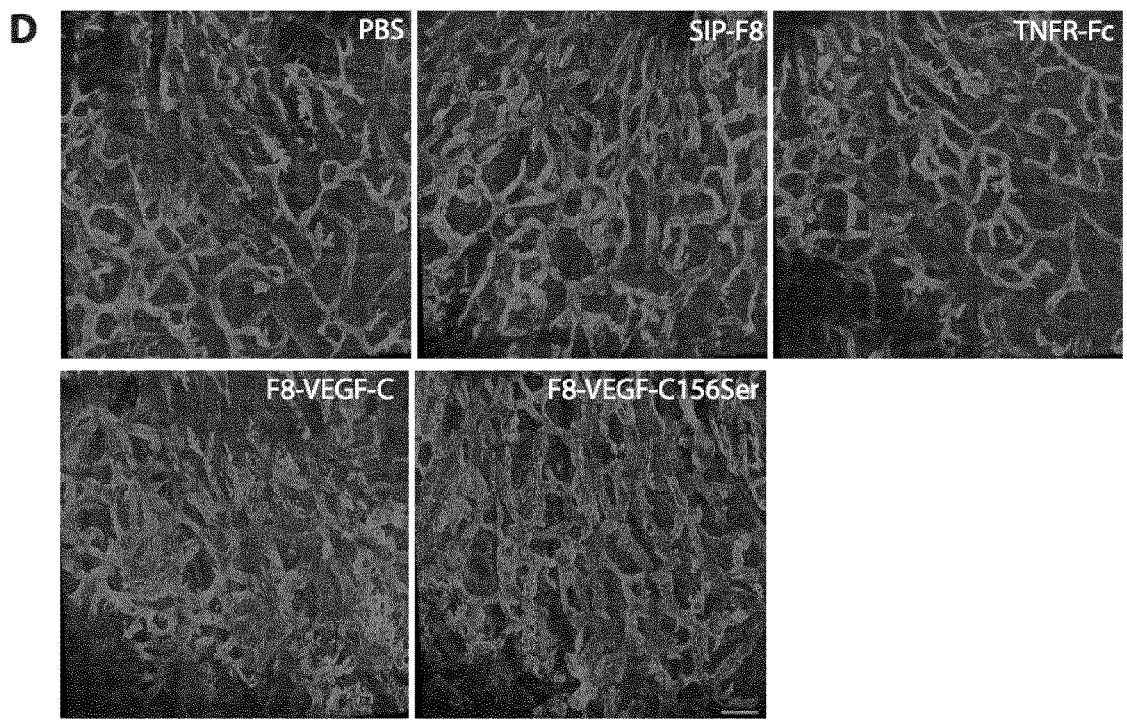
Figure 5:
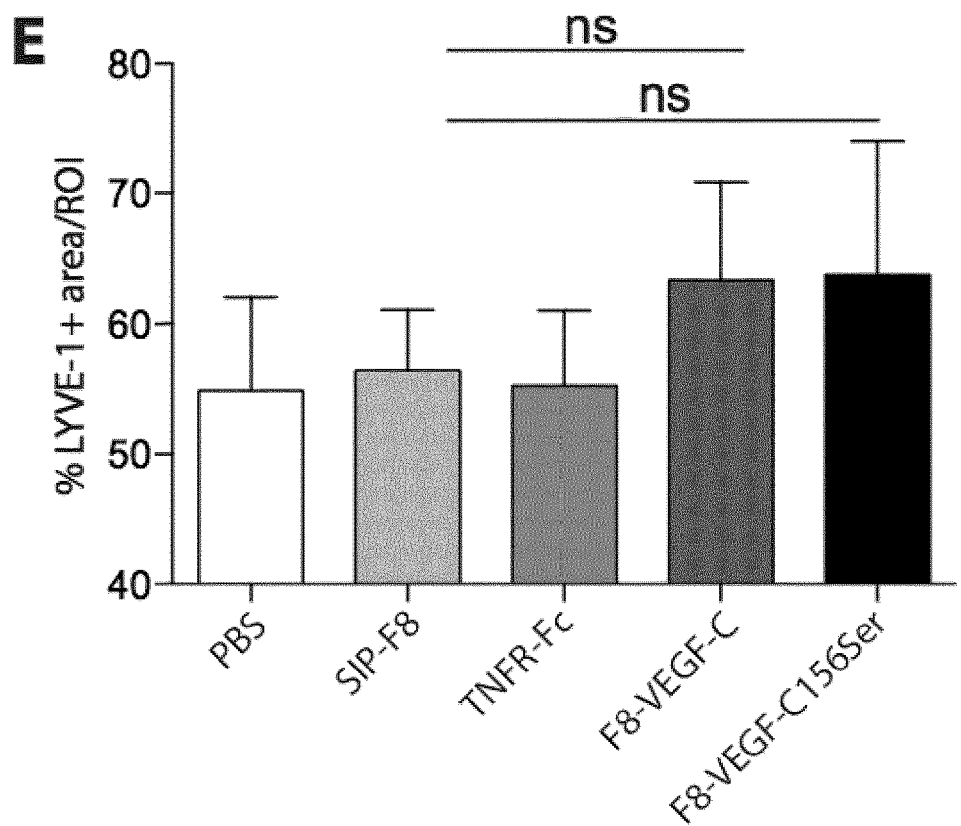
Figure 5:
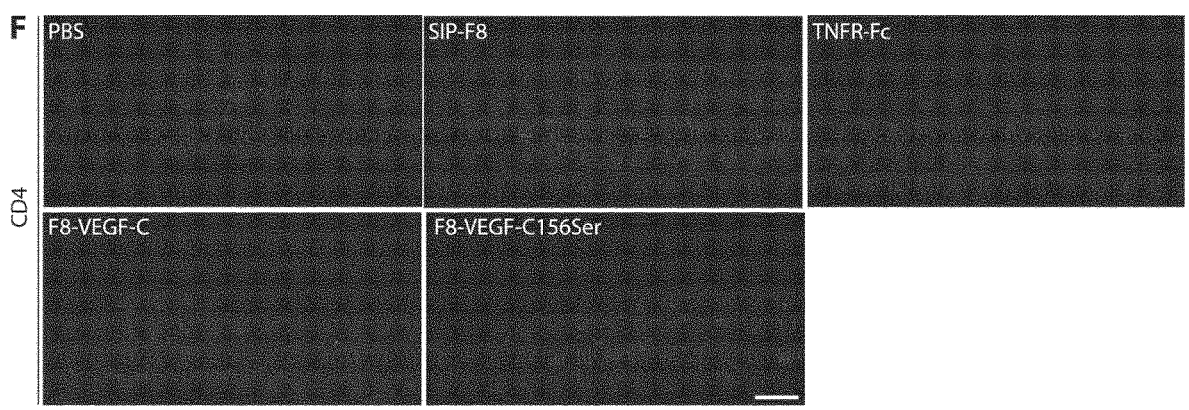
Figure 5:
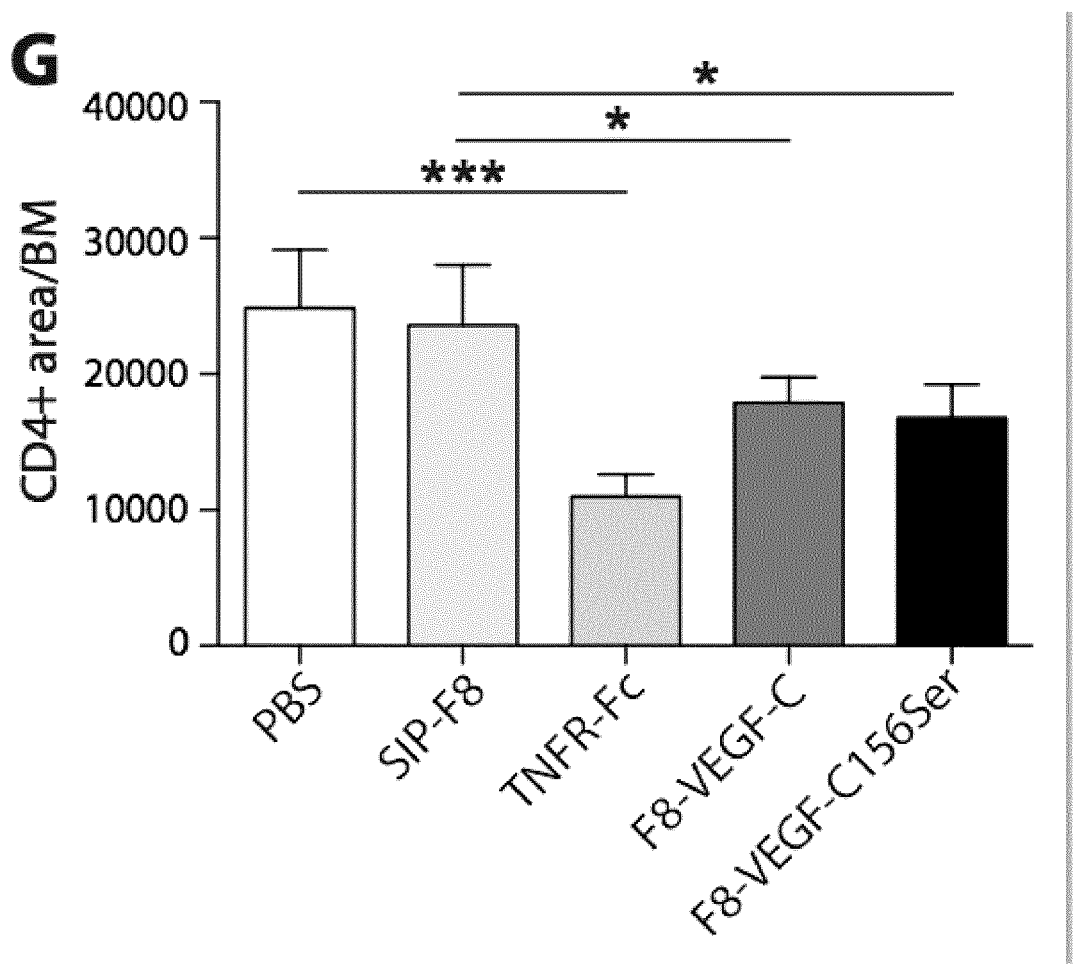

The ear thickness of K14-VEGF-A mice subjected to Contact Hypersensitivity (CHS) was evaluated. Animals received i.v. injections of F8-VEGF-C, KSF-VEGF-C or PBS on days 7, 9 11 and 13 after challenge. F8-VEGF-C but not KSF-VEGF-C or PBS reduced ear oedema (FIG. 4A). FIG. 4B shows the staining of the lymphatic (LYVE-1, green) vessels in the frozen K14-VEGF-A ear sections. The quantification of the stained K14-VEGF-A ear sections revealed that the treatment with F8-VEGF-C increased lymphatic vessel area (FIG. 4C).

(ii) F8-VEGF-C and F8-VEGF-C156Ser but not SIP-F8 inhibited skin inflammation to a degree comparable with TNFR-Fc in the CHS-induced skin inflammation. In hemizygous K14-VEGF-A transgenic mice, a CHS-induced skin inflammation was induced (n=5 per group). Treatment with F8-VEGF-C and F8-VEGF-C156Ser from day 7 onwards, every second day, significantly reduced inflammatory ear swelling as compared to SIP-F8 and had a similar effect as TNFR-Fc (FIG. 5A). The FIGS. 5B and 5C show the quantitative image analyses of immunofluorescence stains of inflamed K14-VEGF-A tg ear skin for LYVE-1 and MECA-32. It revealed a significantly increased LYVE-1 positive lymphatic area in the F8-VEGF-C and F8-VEGF-C156Ser treatment groups. Staining for LYVE-1 in FIGS. 5D and 5E showed an increased lymphatic vessel network in F8-VEGF-C and F8-VEGF-C156Ser-treated mice. FIGS. 5F and 5G show immunofluorescence stains of inflamed ear skin for CD4 which revealed that F8-VEGF-C, F8-VEGF-C156Ser and TNFR-Fc treatment reduced the infiltration with CD4+ T cells as compared to PBS and SIP-F8.

Figure 6:
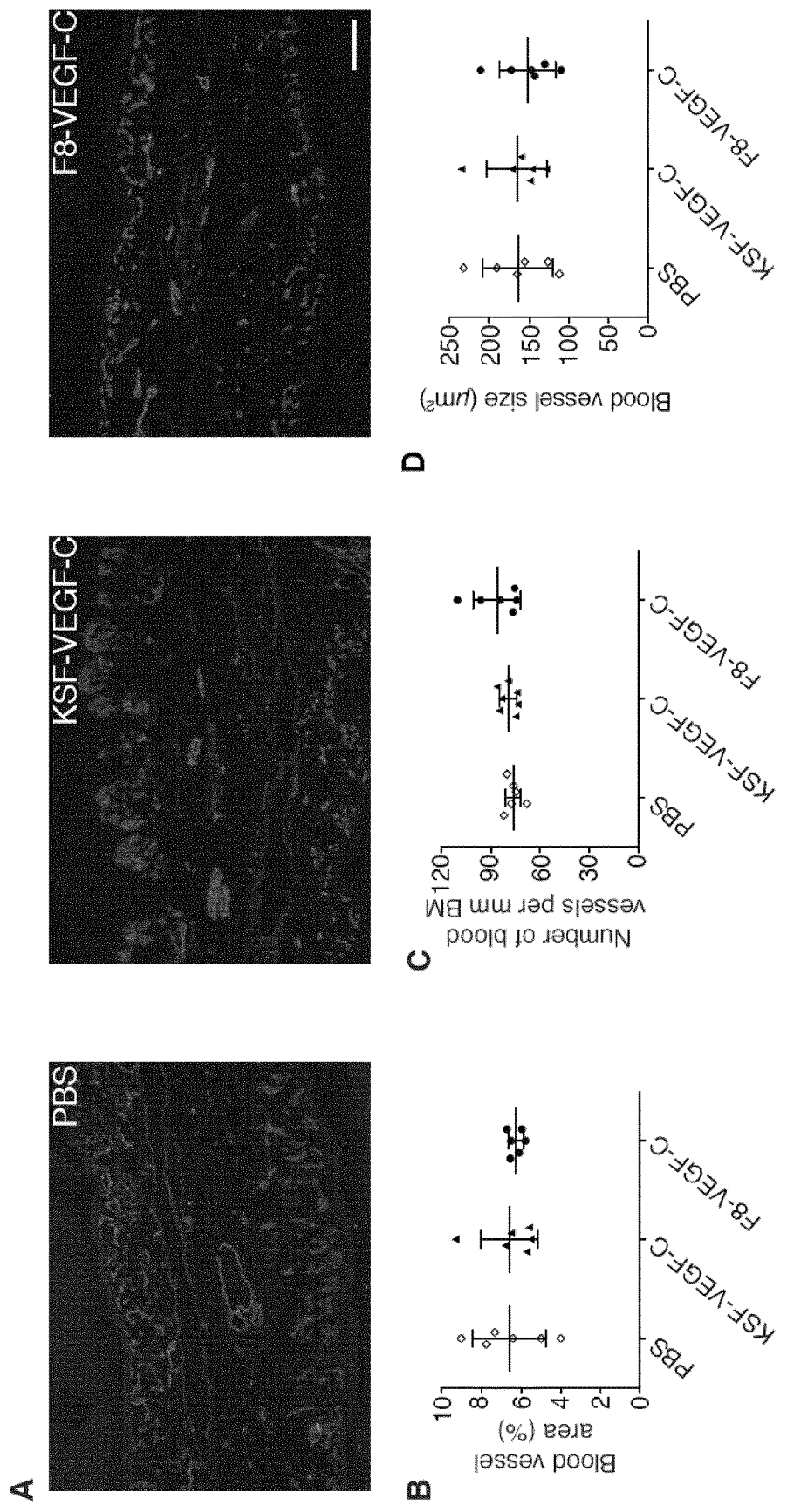
FIG. 6. Systemic application of VEGF-C does not affect blood vessel phenotype in inflamed ears of K14-VEGF-A mice. (A) Immunofluorescent images of inflamed ears from mice having received PBS (left), KSF-VEGF-C (center) or F8-VEGF-C (right) stained for MECA-32 (pale grey) scale bar=100 µm. (B) Quantification of blood vessel area in inflamed ears of mice having received the indicated treatment (expressed as percent of analyzed area, n=6 animals per group, one-way ANOVA with Bonferroni post-test). (C) Number of blood vessels in inflamed ears (normalized to basement membrane, n=6-7 animals per group). (D) Size of blood vessels in inflamed ears (n=6 animals per group, one-way ANOVA with Bonferroni post-test). BM=basement membrane. Data represent mean±SD. *P<0.05, P<0.01, *P<0.001.
Figure 7:
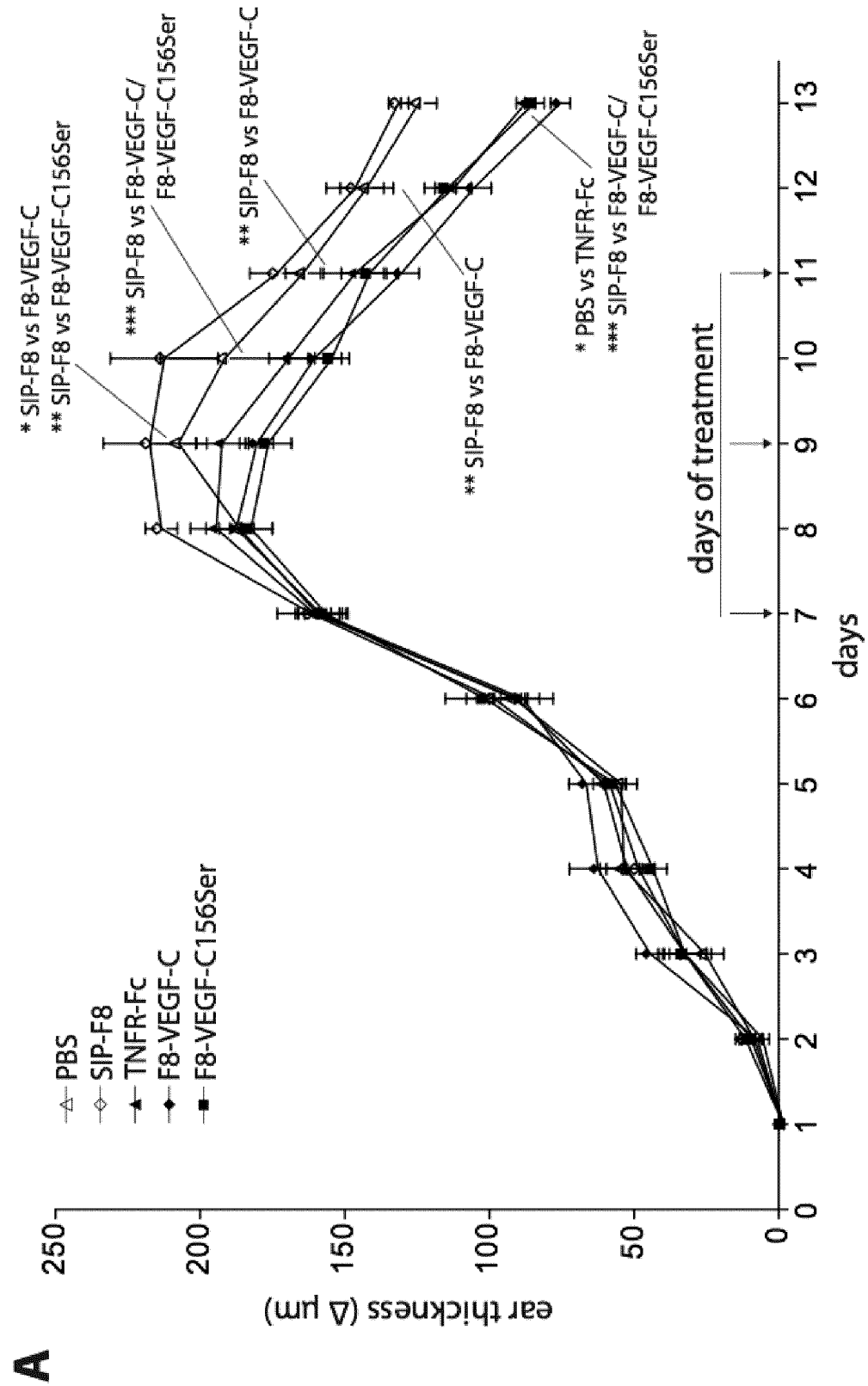
FIG. 7: F8-VEGF-C and F8-VEGF-C156Ser but not SIP-F8 inhibit skin inflammation to a degree comparable with TNFR-Fc in IMQ-induced skin inflammation. (A) In the IMQ-induced skin inflammation model (n=5 mice per group), treatment with F8-VEGF-C and F8-VEGF-C156Ser from day 7 onwards, every second day, significantly accelerated the resolution of oedema as compared to treatment with SIP-F8 or PBS. The effect was comparable to the effect of TNFR-Fc. Data represent mean±SEM. (B, C) H&E stains of ear skin sections and quantitative image analysis showed that TNFR-Fc, F8-VEGF-C and F8-VEGF-C156Ser treatment significantly reduced epidermal thickness as compared to PBS- and SIP-F8-treated mice. (D) Representative images of immunofluorescence stains of IMQ-inflamed ear skin for LYVE-1 and MECA-32. (E) Quantitative image analysis revealed a significant increase of the lymphatic vessel size in F8-VEGF-C-treated mice. Scale bars represent 100 µm. Data represent mean±SD. *P<0.05; "P<0.01; *"P<0.001.
Figure 7:
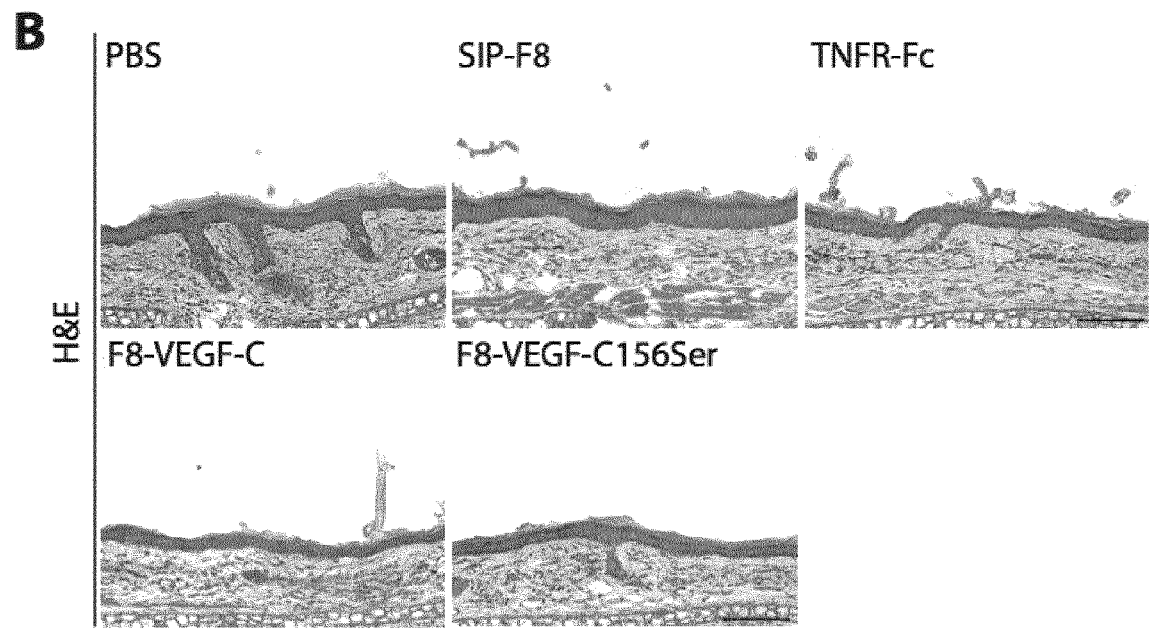
Figure 7:
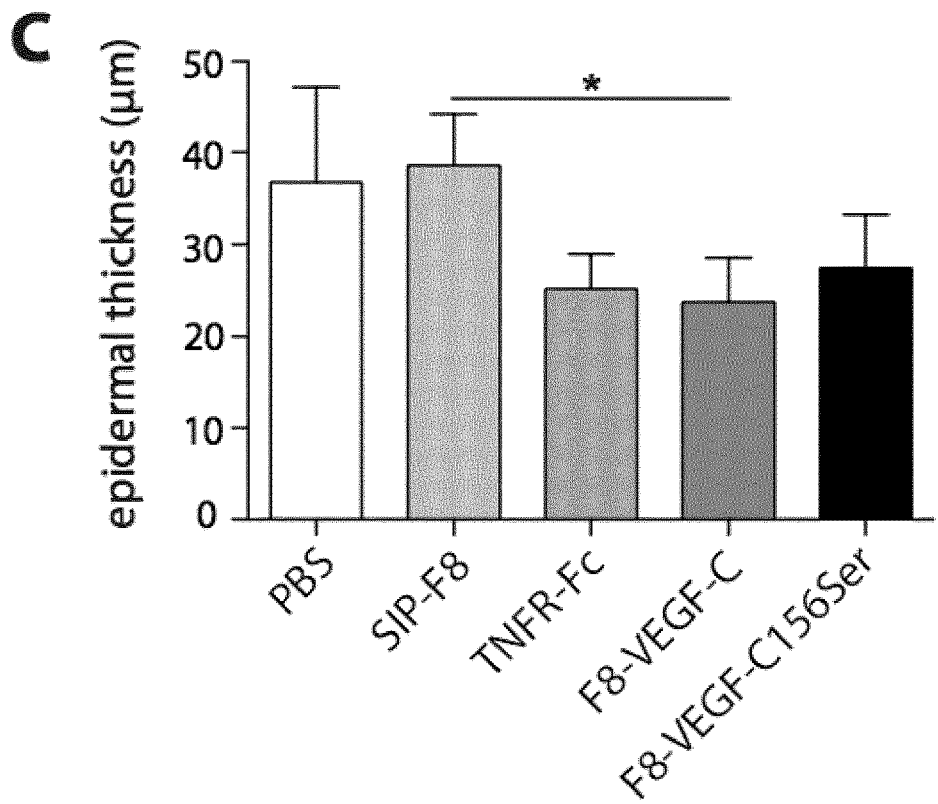
Figure 7:
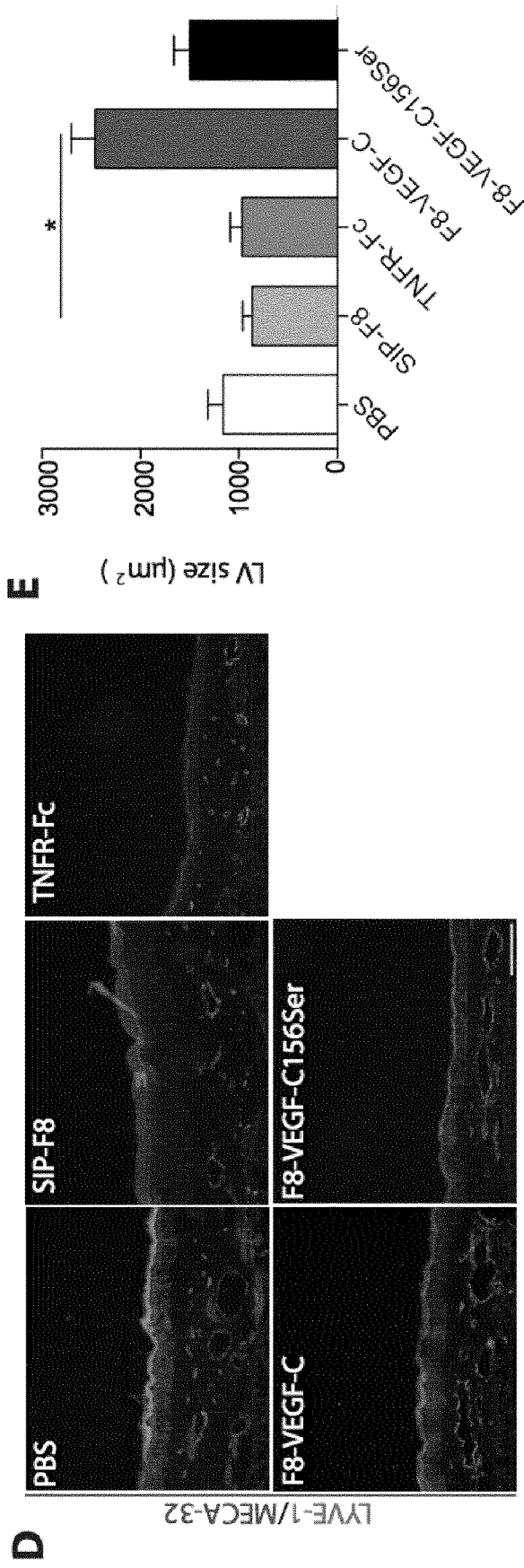

(iii) Systemic application of targeted F8-VEGF-C or untargeted KSF-VEGF-C had no effect on the blood vessel phenotype when compared to PBS-treated control animals. FIG. 6A shows representative images of immunofluorescence stains of inflamed ear skin of mice undergoing CHS-induced inflammation for MECA-32 (pale grey). The quantification of MECA-32 stained sections revealed no changes in blood vessel area (FIG. 6B), blood vessel number (FIG. 6C) or in the average size of blood vessels (FIG. 6D).

Second Model of Chronic Skin Inflammation: The IMQ-Induced Skin Inflammation Model (i) The effect of F8-VEGF-C on ear thickness and lymphatic vessels in the IMQ-induced skin inflammation model was evaluated. F8-VEGF-C but not KSF-VEGF-C alleviates chronic skin inflammation. The effect of F8-VEGF-C on the ear thickness of C57Bl/6 mice was measured. Imiquimod-containing cream was applied daily on days 1-5 and on day 7. Mice received i.v. injections of F8-VEGF-C, KSF-VEGF-C or SIP-F8 on days 7, 9 and 11. F8-VEGF-C but not KSF-VEGF-C or SIP-F8 accelerated oedema resolution (FIG. 4D). The FIG. 4E shows the lymphatic vessels through the staining of the lymphatic specific marker LYVE-1 in frozen ear sections of animals that underwent imiquimod-induced inflammation. The quantification of LYVE-1 stained ear tissue showed that treatment with F8-VEGF-C increased lymphatic vessel area compared to KSF-VEGF-C or SIP-F8 (FIG. 4F).

(ii) F8-VEGF-C and F8-VEGF-C156Ser but not SIP-F8 inhibited skin inflammation to a degree comparable with TNFR-Fc in this IMQ-induced skin inflammation model. FIG. 7A shows in the IMQ-induced skin inflammation model (n=5 mice per group), that the treatment with F8-VEGF-C and with F8-VEGF-C156Ser from day 7 on, every second day, significantly accelerated the resolution of oedema as compared to SIP-F8 and PBS. The effect was comparable to the effect of TNFR-Fc which, as explained above, is one of the standard therapies for chronic inflammatory diseases such as psoriasis. In FIGS. 7B and 7C, the H&E stains of the ear skin sections showed that TNFR-Fc, F8-VEGF-C and F8-VEGF-C156Ser treatment significantly reduced the epidermal thickness as compared to PBS and SIP-F8-treated mice. FIG. 7D shows representative images of immunofluorescence stains of IMQ-inflamed ear skin for LYVE-1 and MECA-32. In FIG. 7E, the quantitative image analysis revealed a significant increase of the lymphatic vessel size in F8-VEGF-C-treated mice.

Figure 8:
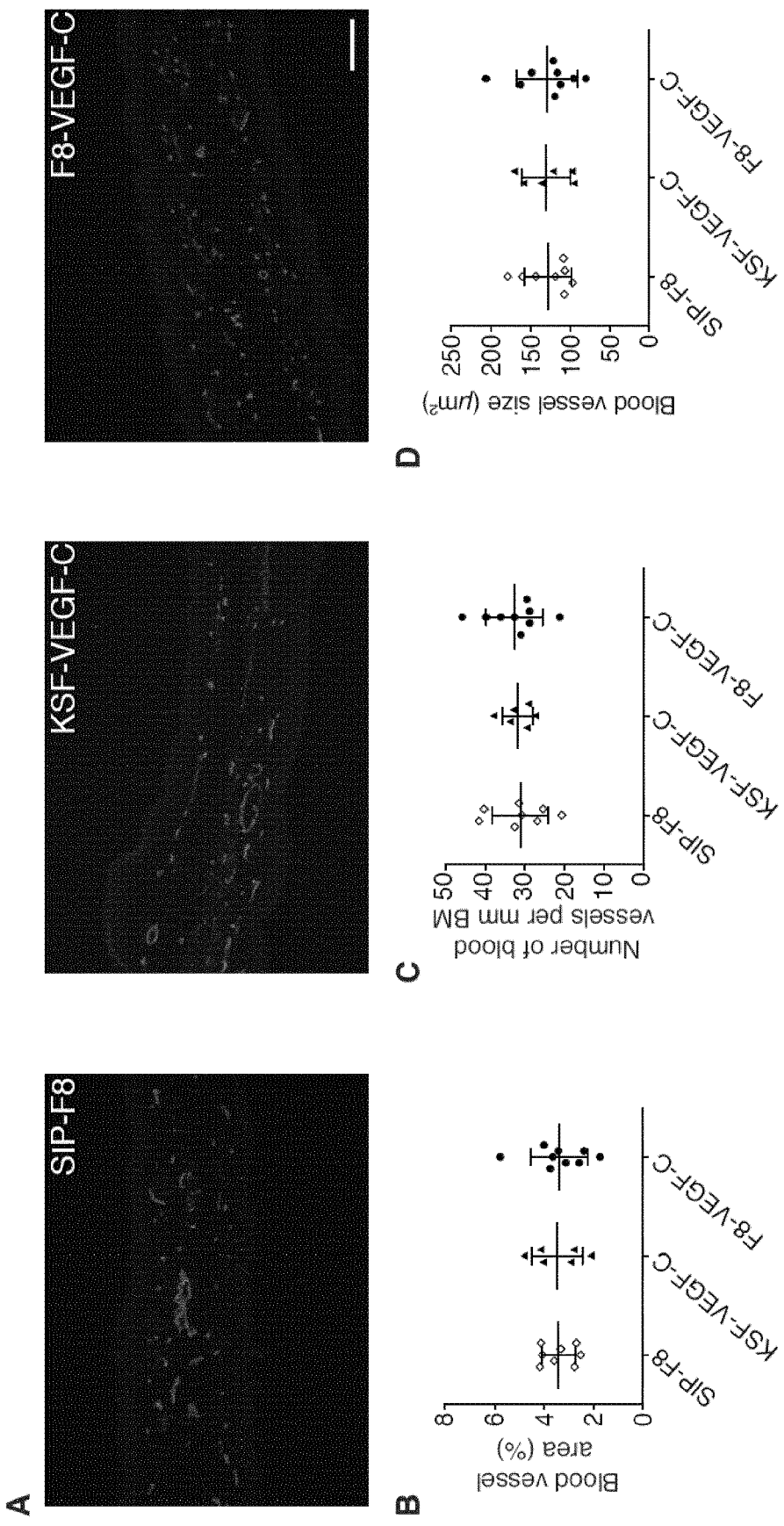
FIG. 8. Systemic application of VEGF-C does not affect blood vessel phenotype in IMQ-induced ear skin inflammation. (A) Immunofluorescent images of IMQ-inflamed ears from mice having received SIP-F8 (left), KSF-VEGF-C (center) or F8-VEGF-C (right) stained for MECA-32 (pale grey), scale bar=100 µm. (B) Quantification of blood vessel area in inflamed ears of mice having received the indicated treatment (expressed as percent of analyzed area, n=6-9 animals per group, one-way ANOVA with Bonferroni post-test). (C) Number of blood vessels in inflamed ears (normalized to basement membrane, n=6-9 animals per group). (D) Size of blood vessels in inflamed ears (n=6-9 animals per group, one-way ANOVA with Bonferroni post-test). Data represent mean±SD. BM=basement membrane. *P<0.05, P<0.01, *P<0.001.

(iii) Systemic application of F8-VEGF-C or KSF-VEGF-C had no effect on the blood vessel phenotype when compared to SIP-F8-treated control animals. Analysis of immunofluorescence stains of IMQ-inflamed ear skin for MECA-32 (representative images in FIG. 8A) showed no changes in blood vessel area (FIG. 8B), number (FIG. 8C) or average blood vessel size (FIG. 8D) upon treatment with F8-VEGF-C or KSF-VEGF-C compared to SIP-F8 treatment.

Several conclusions can be drawn from these experiments:

F8-VEGF-C and F8-VEGF-C156Ser reduce ear oedema significantly compared to SIP-F8, indicating that targeting of ED-A alone has no effect on ear inflammation.

F8-VEGF-C reduces ear oedema significantly compared to KSF-VEGF-C, indicating that the targeting of VEGF-C is essential for the fusion protein's effectiveness and that injection of untargeted VEGF-C has no notable effect on inflammation.

F8-VEGF-C and F8-VEGF-C156Ser reduce ear oedema to a similar extent as TNFR-Fc, one of the standard therapies for chronic inflammatory diseases such as psoriasis or rheumatoid arthritis, indicating that targeted VEGF-C delivery may represent a valuable alternative treatment approach for these diseases.

Surprisingly, F8-VEGF-C does not affect blood vessels in inflamed ear skin. This is unexpected, as VEGF-C was previously reported to also bind to VEGFR-2, which is expressed on blood vascular endothelial cells (Saaristo A et al. *Adenoviral VEGF-C overexpression induces blood vessel enlargement, tuortuosity, and leakiness but no sprouting angiogenesis in the skin or mucous membranes. FASEB J.* 2002; 16(9): 1041-1049). These results support the conclusion that the therapeutic effect of VEGF-C is mediated by the lymphatic vasculature. The absence of a change in the blood vessel phenotype following systemic application of F8-VEGF-C or KSF-VEGF-C is beneficial, as blood vessel expansion is known to have a detrimental effect in the context of chronic skin inflammation (e.g. Schonthaler H et al. *Systemic Anti-VEGF Treatment Strongly Reduces Skin Inflammation in a Mouse Model of Psoriasis. Proc Natl Acad Sci USA* 2009; 106 (50): 21264-69.).

It is noteworthy that the above effects could be observed in two different mouse models of chronic inflammatory skin disease.

Example 5—Effect of F8-VEGF-C on Lymphatic Clearance Function

Materials and Methods

The polyethylene glycol (PEG)-based lymphatic tracer P20D800 (PEG amine P20 conjugated to IRDye®) was prepared as described previously (Proulx S T et al. "*Use of a PEG-conjugated bright near-infrared dye for functional imaging of rerouting of tumor lymphatic drainage after sentinel lymph node metastasis*", Biomaterials. 2013; 34:5128-37). To examine lymphatic clearance over time, inflamed K14-VEGF-A tg mice (10 days after oxazolone challenge) were anesthetized with isoflurane (2%), and 3 µl of 3 µM tracer was injected intradermally into the ear skin, using a 29 g insulin syringe. The mice were positioned in an IVIS Spectrum imaging system and an image was acquired just after the tracer injection with exposure of 2 s ($\lambda$ex: 745 nm, $\lambda$em: 800 nm, binning of 4) and repeatedly 1 h, 2 h, 3 h, 4 h and 6 h after the injection. Between the different imaging time points, mice were allowed to wake up and move freely. In order to calculate tissue enhancement values, all signal intensities were adjusted to baseline ear signals before tracer injection. The tissue enhancement value obtained directly after the injection of the tracer was used to normalize all values of the subsequent measurements. A one-phase exponential decay model was used to fit the data for each mouse, with lymphatic clearance expressed as decay constant K (expressed in h−1) or as half-life (expressed in h).

Results

Figure 9:
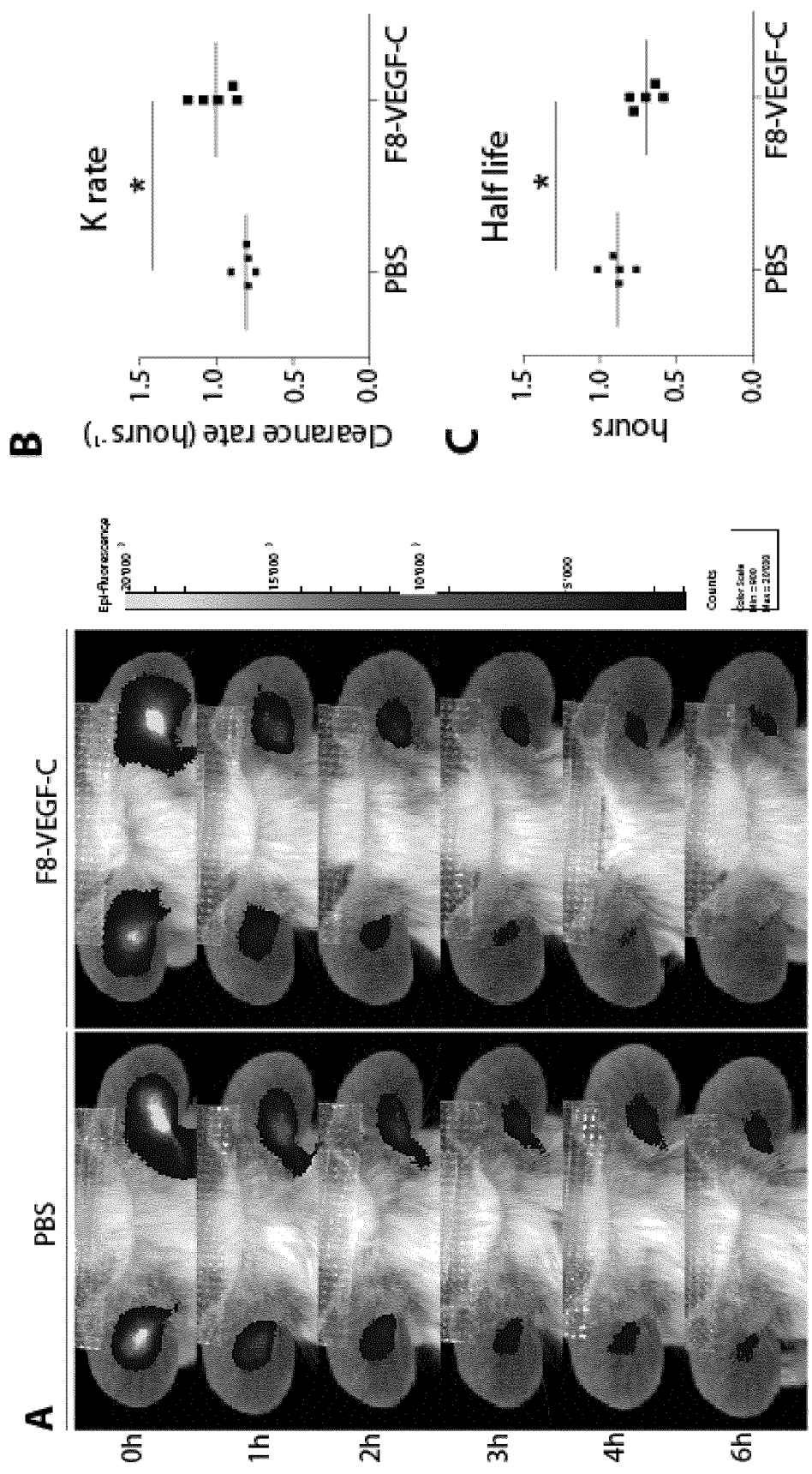
FIG. 9: F8-VEGF-C treatment promotes lymphatic clearance. (A-C) P20D800 (3 µl of 3 µM) was injected into the ears of CHS-induced inflamed mice treated with either PBS (n=5) or F8-VEGF-C (n=5) and the decay of fluorescent signal was tracked over time (A). F8-VEGF-C-treated mice had an increased clearance of the lymphatic tracer as shown by a significantly increased clearance rate (B) and a reduction in tissue half-life (C). Similarly, 4 injections of F8-VEGF-C increased the clearance rate in mice undergoing IMQ-induced skin inflammation compared to animals receiving KSF-VEGF-C (D) and reduced tissue half-life (E). Data represent mean±SD. *P<0.05.
Figure 9:
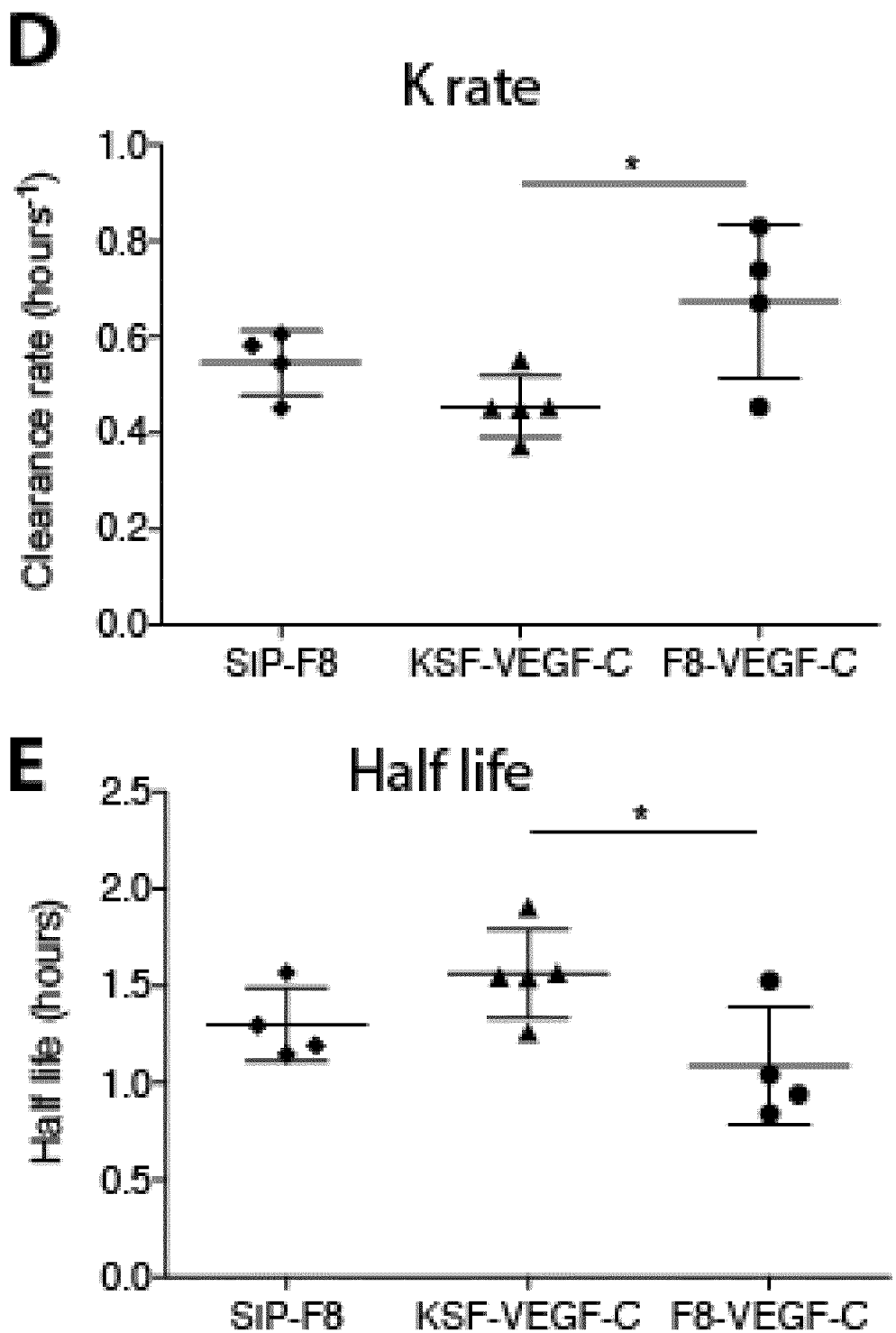

F8-VEGF-C significantly improves lymphatic clearance function in inflamed ears of K14-VEGF-A tg mice compared to PBS (FIG. 9). This result clearly shows, that the expanded lymphatic vasculature is functional. Furthermore, an increased clearance of inflammatory cells and/or inflammatory mediators could be a possible mechanism by which the F8-VEGF-C fusion protein exerts its anti-inflammatory effects.

Example 6—Treatment Effects of F8-VEGF-C on Blood Values in an Atherosclerosis Model Materials and Methods Disease Model ApoE knockout (ApoE KO) mice were put on a high-fat diet (HFD). Two weeks later, a cast was implanted around the left common carotid artery (LCCA), modulating blood flow in said vessel and causing the formation of unstable atherosclerotic plaques, while more stable plaques formed in the heart, brachiocephalic artery and the aortic arch, allowing for plaque-staging. After 8 weeks on HFD, monocytes were labelled with fluorescent latex beads to quantify the monocyte egress from atherosclerotic lesions. Untreated mice on HFD were euthanized at week 9 to establish baseline values for endpoint readouts. Mice were sacrificed after having received five injections of F8-VEGF-C or PBS over the course of 10-11 days. Due to the fact that some mice were not fully responsive and failed to develop lesions at all sites of interest, the number of animals included for analysis varied for the different anatomical sites.

Quantification of Blood Values

Mice were euthanized by ketamine/xylacine overdose, the blood was collected by heart puncture.

Plasma cholesterol and triglyceride levels were determined by CHOD-PAP kit (Roche/Hitachi) and GPO-PAP kit (Roche/Hitachi) respectively, according to the manufacturer's instructions.

The number of classical monocytes, non-classical monocytes, neutrophils, B cells and T cells was quantified by Flow cytometry. Specifically, blood was incubated with red blood cell lysis buffer (150 mM $NH_4Cl$, 10 mM $KHCO_3$, 0.1 mM $Na_2EDTA$) for 5 min at room temperature. Leukocytes were stained with antibodies to CD45 (Biolegend, clone: 30-F11), CD11b (Biolegend, clone: M1/70), Gr1 (eBioscience, clone RB6-8C5), CD115 (eBioscience, clone: AFS98), CD45R (B220, eBioscience, clone RA3-6B2), CD3 (eBioscience, clone 145-2C11) in staining buffer (20 min, 4° C.). Blood leukocytes were defined with the following surface markers: classical monocytes: $CD45^+CD11B^+CD115^+Gr1^{high}$, non-classical monocytes: $CD45^+CD11B^+CD115^+Gr1^{low}$, neutrophils: $CD45^+CD11B^+CD115^-Gr1^{high}$, B cells: $CD45^+CD11B^-B220^+$ and T-cells: $CD45^+CD11B^-CD3^+$. Absolute cell numbers were assessed by use of CountBright™ absolute counting beads (Invitrogen). Flow cytometry was performed using the LSR Fortessa (Beckton Dickinson) and data was analysed using FlowJo software (Beckton Dickinson).

Results

Figure 10:
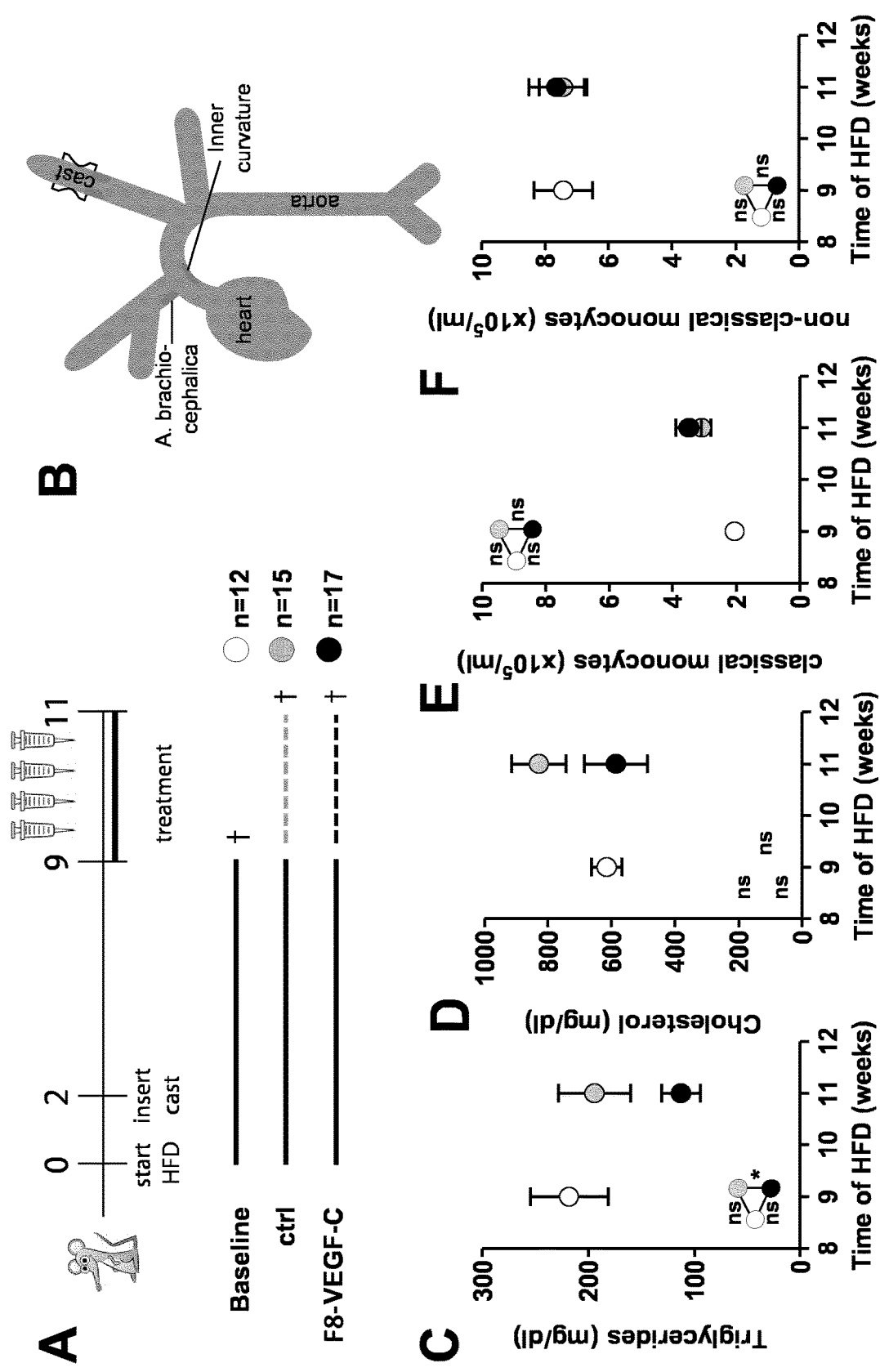
FIG. 10: Treatment effects on blood values. (A) Study overview, listing the number of animals included for analysis in the respective treatment groups. The duration of the study in number of weeks (0, 2, 9 and 11) is indicated. (B) Schematic showing the different sites of interest where plaques form; results in this figure relate to blood parameters. (C) Quantification of triglyceride levels. (D) Quantification of cholesterol levels. (E) Quantification of number of classical monocytes (CD45+ CD11b+ CD115+ Gr1 (high)). (F) Quantification of number of non-classical monocytes (CD45+ CD11b+ CD115+ Gr1(low)). (G) Quantification of neutrophil numbers. (H) Quantification of B cell numbers. (I) Quantification of T cell numbers. Data represent mean±SEM, analysed by one-way ANOVA.
Figure 10:
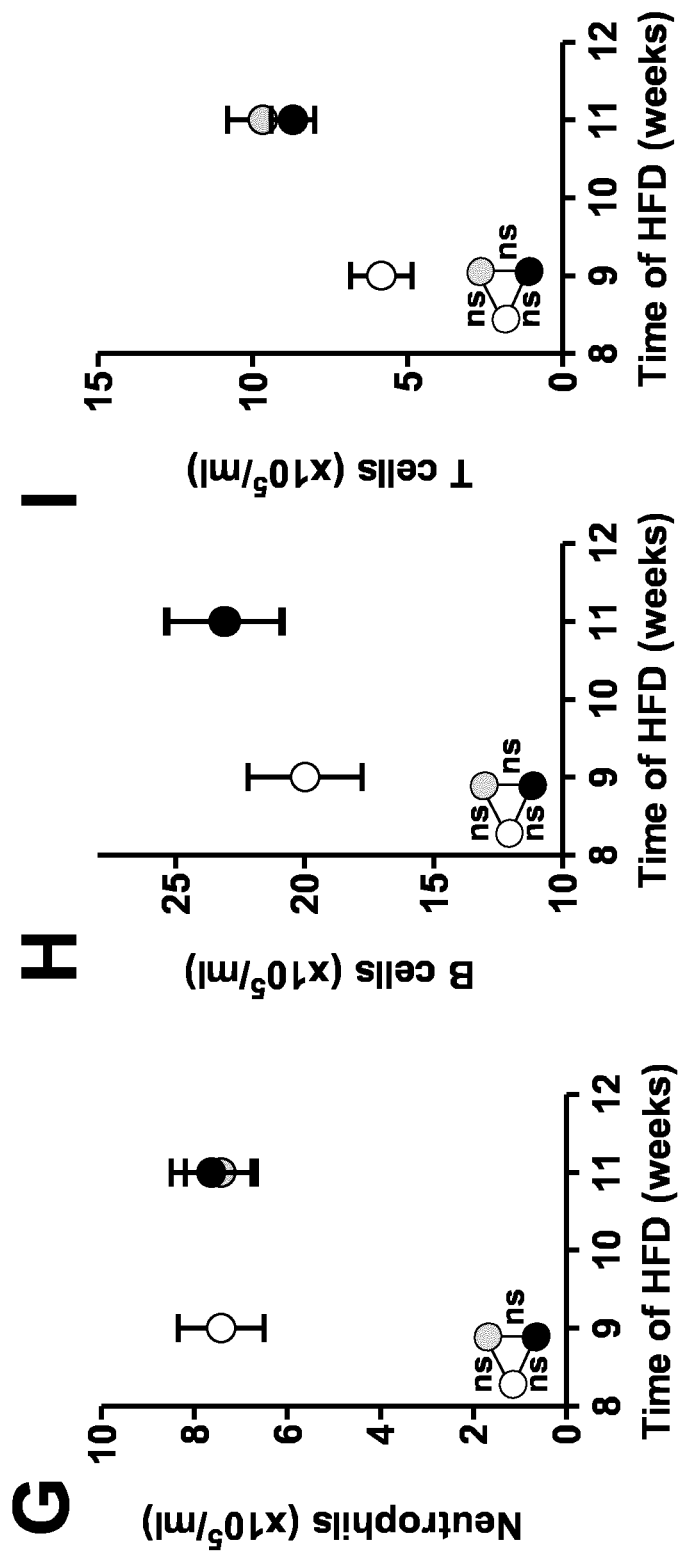

The treatment with F8-VEGF-C significantly reduced blood triglyceride levels compared to PBS-injected mice (FIG. 10C) and revealed a trend towards decreased cholesterol (FIG. 10D). Other parameters measured, such as numbers of neutrophils, monocytes, B and T cells remained unchanged when the mice were treated with F8-VEGF-C compared to PBS-injected mice (FIG. 10E-I).

Example 7—Treatment Effects of F8-VEGF-C on Unstable Plaques in the LCCA

Materials and Methods
Disease Model

The ApoE KO mouse model used in these experiments was as described in Example 6 above.

Analysis of Unstable Plaques at the Cast in the LCCA
Hematoxylin-Eosin Staining of LCCA Containing Atherosclerotic Plaques:

Mice were euthanized by ketamine/xylacine overdose, the blood was collected by heart puncture after which the mice were flushed with 20 mL of ice cold PBS-EDTA (5 mM EDTA). Subsequently, the left common carotid artery was embedded in Tissue Tek O.C.T. compound (Sakura Finetek) for analysis. For the spontaneous atheroprogression model, aortic arches were isolated, fixed with 4% PFA and embedded in paraffin. Cryosections (7 μm) or paraffin sections (4 μm) were histologically stained with hematoxylin and eosin (HE) in 70 or 40 μm intervals, respectively Histology and Immunofluorescence:

Cryosections (7 μm) or paraffin sections (4 μm) were histologically stained with hematoxylin and eosin (HE) in 70 or 40 μm intervals, respectively. Total collagen content was assessed by picrosirius red staining in consecutive sections. For immunofluorescence staining, cryosections were fixed with cold acetone followed by antigen blockade using 5% goat serum/phosphate buffered saline. Paraffin sections underwent antigen retrieval with citrate buffer (10 mM, pH 6.0) before antigen blockade using 5% goat serum/phosphate buffered saline. Next, sections were incubated overnight at 4° C. with the following primary antibodies: rabbit anti-mouse CD68 (Abcam, 1:200), mouse anti-mouse smooth muscle actin (SMA)-Fitc conjugated (Sigma, 1:500). After extensive washing, sections were incubated with secondary antibodies conjugated with DyLight 550 or DyLight 650 (Thermo Fisher, 1:500). Counterstaining to visualize nuclei was performed by incubating with DAPI (Molecular Probes). For lipid staining in smooth muscle cells and macrophages, cryosections were fixed with 4% PFA. Next, samples were stained with oil-ded O. After extensive washing antigen blockade and immunofluorescence to visualize SMA and CD68 was performed as described above. Immunofluorescence sections were imaged using a Leica TCS SP8 (Leica Microsystems) equipped with a UV laser, a freely tunable, pulsed white light laser, hybrid detectors and a 63×1.40 oil objective. Histological sections were quantified by computer-assisted morphometric analysis using ImageJ software (National Institutes of Health).

Quantification of Lesion Size Expressed as Tunica Intima/Media Ratio:

The intima and media area was analyzed in HE-stained sections. Intima/media ratio was analyzed as the quotient of intima area and media area.

Quantification of Necrotic Core Size Expressed as Percent of Intima:

The intima and necrotic core area was analyzed in HE-stained sections. Necrotic core (NC) was defined as the area devoid of nuclei underneath a formed fibrous cap. Necrotic core size was expressed as quotient of necrotic core and intima area.

Sirius Red Staining of LCCA Containing Atherosclerotic Lesions:

Sections of LCCA were incubated with picrosirius red solution. Staining reaction was stopped by washing with acidified water. Sections were subsequently dehydrated in ethanol, cleared and mounted.

Quantification of Collagen Fibres in Lesions, Expressed as Percent of Intima:

The intima area was analyzed in HE-stained sections. Total collagen content was assessed by picrosirius red staining in consecutive sections as described above and expressed as the quotient of collagen area and intima area.

Quantification of Fibrous Cap Thickness Expressed as Percent of Intima:

The intima area was analyzed in HE-stained sections. Fibrous cap (FC) thickness was measured on picrosirius red-stained sections as described above and defined as the average of length measurements in the positions overlapping with the lines of a square-shaped grid. FC thickness was corrected by lesion size by analyzing the quotient of average FC length and intima area. Animal with carotid samples showing absence of lesion formation were excluded from this analysis.

Immunofluorecent Stainings for Smooth Muscle Actin, CD68 (Macrophage Marker and DAPI in LCCA Containing Atherosclerotic Plaques:

Immunofluorescence staining and imaging of immunofluorescence sections was performed as described under "Histology and immunofluorescence" above. Histological sections were quantified by computer-assisted morphometric analysis using ImageJ software (National Institutes of Health).

Quantification of Smooth Muscle Cell Area Expressed as Percent of Intima:

The intima area was analyzed in HE-stained sections. Smooth muscle cell area was measured as smooth muscle actin-positive area and the quotient of smooth muscle cell and intima area was calculated.

Quantification of Macrophage Area Expressed as Percent of Intima:

The intima area was analyzed in HE-stained sections. The macrophage area was defined as the CD68-positive area on stained slides. The macrophage area was reported as the quotient of macrophage and intima area.

Oil Red O Staining Combined with Immunofluorescent Staining for Smooth Muscle Actin, CD68 and DAPI:

For lipid staining in smooth muscle cells and macrophages, cryosections were fixed with 4% PFA. Next, samples were stained with oil-red O. After extensive washing, antigen blockade and immunofluorescence to visualize SMA and CD68 was performed as described above.

Quantification of Lipids in Smooth Muscle Cells Expressed as Percent of Smooth Muscle Cell Area:

Lipids in smooth muscle cells were calculated as the double-positive area for SMA and lipids (as assessed in oil-red O stainings) divided by the total smooth muscle cell area defined as the total SMA-positive area.

Quantification of Lipids in Macrophages Expressed as Percent of Macrophage Area:

Lipids in macrophages were calculated as the double-positive area for CD68 and lipids (as assessed in oil-red O stainings) divided by the total macrophage area defined as the total CD68-positive area.

Results

Figure 11:
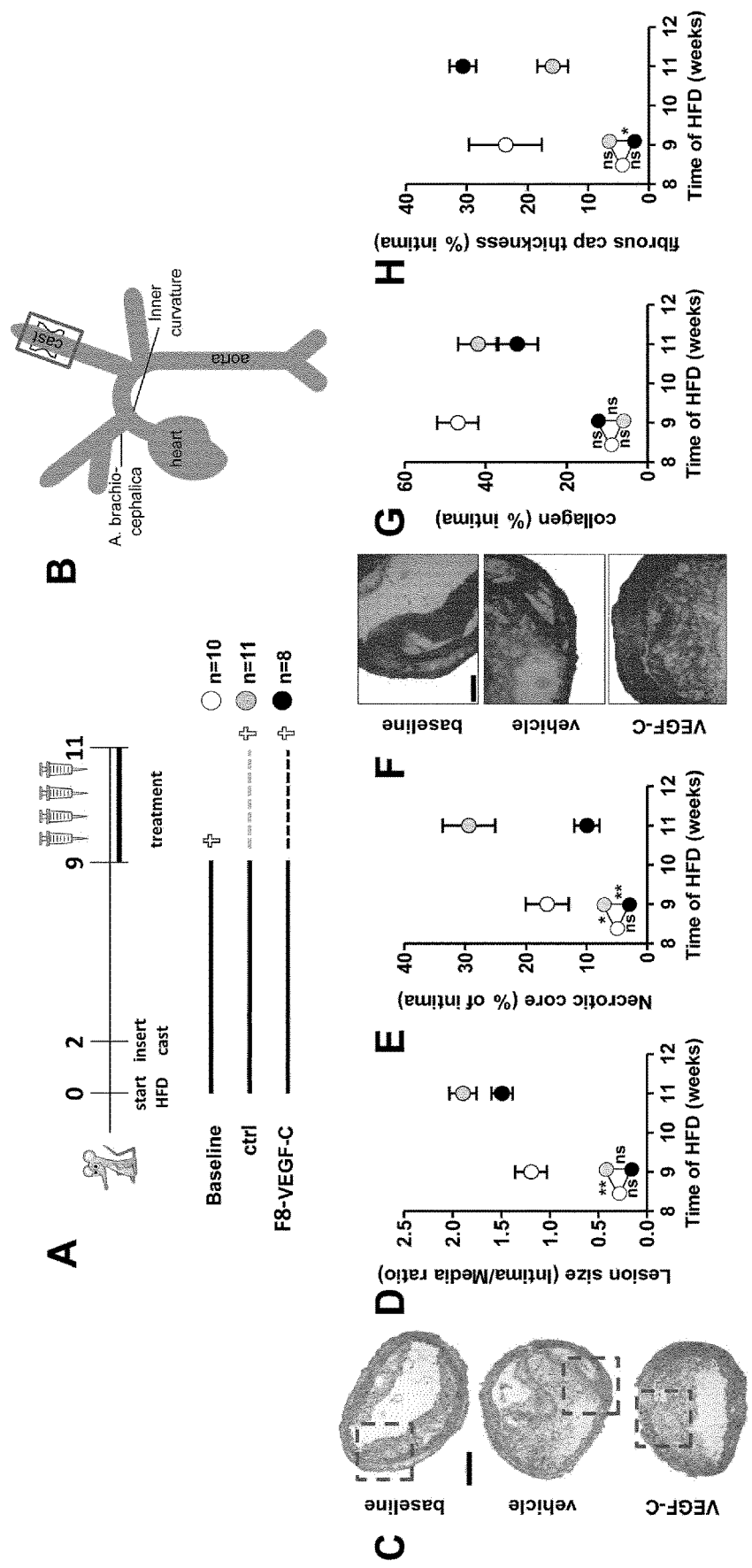
FIG. 11: Treatment effects on unstable plaques in left common carotid artery (LCCA). (A) Study overview, listing the number of animals included for analysis in the respective treatment groups. The duration of the study in number of weeks (0, 2, 9 and 11) is indicated. (B) Schematic showing the different sites of interest; results in this figure relate to the unstable plaques forming around the cast. (C) Hematoxylin-eosin staining of LCCA containing atherosclerotic plaques, rectangles highlight regions for magnification. (D) Quantification of lesion size expressed as tunica intima/media ratio. (E) Quantification of necrotic core size expressed as percent of intima. (F) Sirius red staining of LCCA containing atherosclerotic lesions. (G) Quantification of collagen fibres in lesions, expressed as percent of intima. (H) Quantification of fibrous cap thickness expressed as percent of intima. (I) Immunofluorescent stainings for smooth muscle actin, CD68 (macrophage marker) and DAPI in LCCA containing atherosclerotic plaques. (J) Quantification of smooth muscle cell area expressed as percent of intima. (K) Quantification of macrophage area expressed as percent of intima. (L) Oil Red O staining combined with immunofluorescent staining for smooth muscle actin, CD68 and DAPI. (M) Quantification of lipids in smooth muscle cells expressed as percent of smooth muscle cell area. (N) Quantification of lipids in macrophages expressed as percent of macrophage area. Data represent mean±SEM, analysed by one-way ANOVA.
Figure 11:
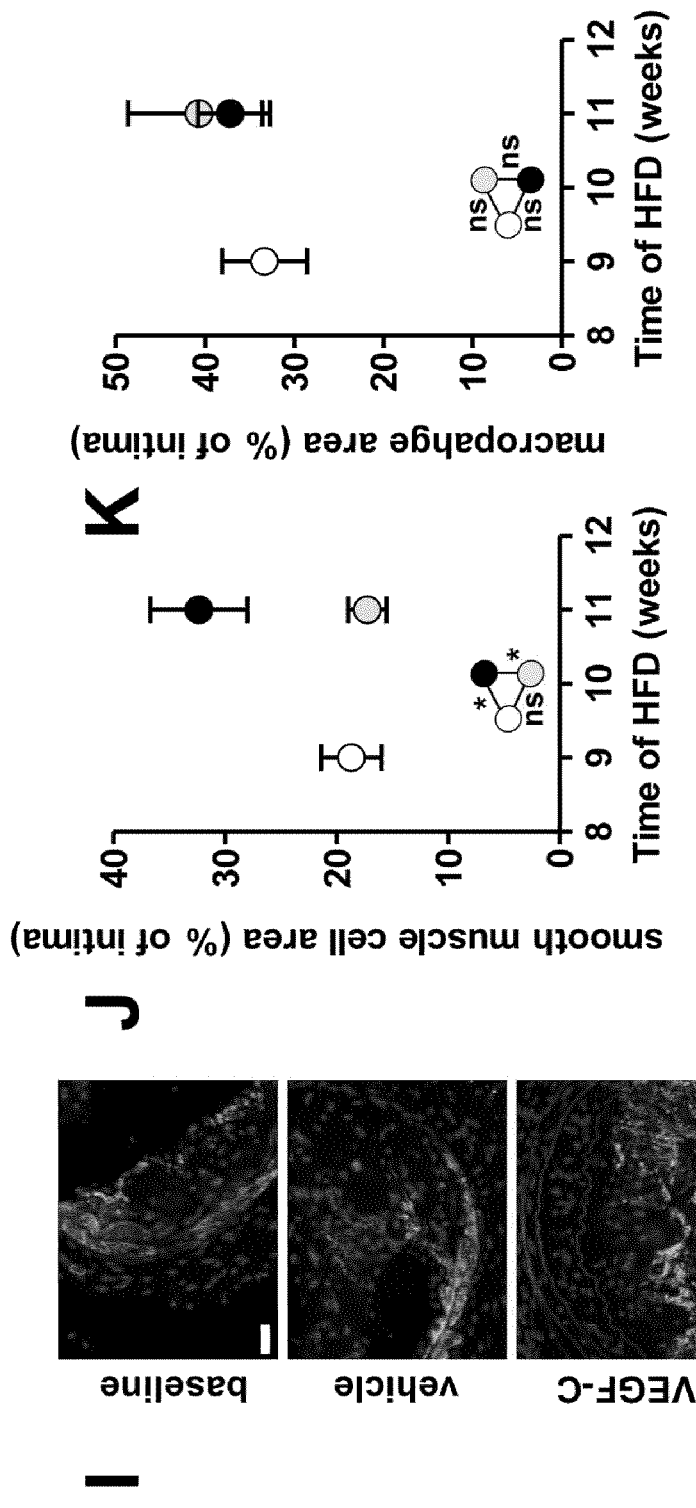
Figure 11:
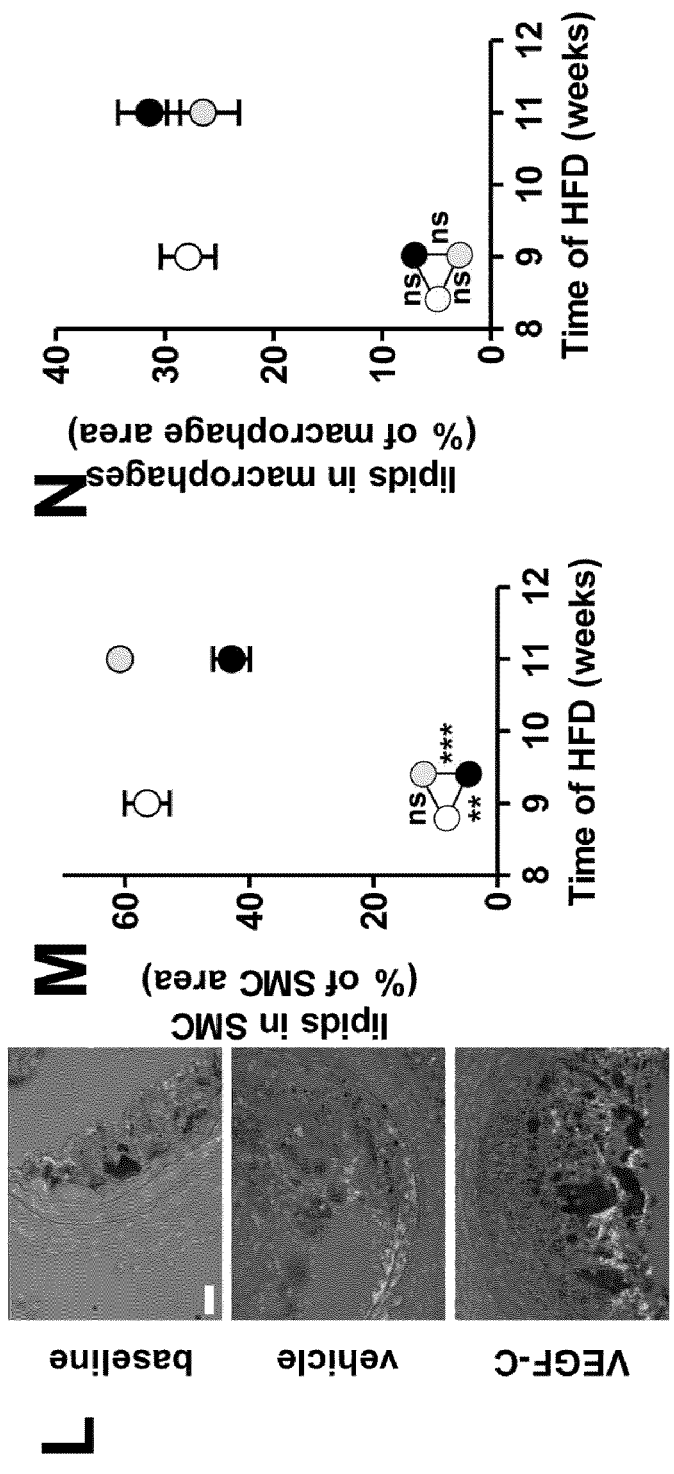

Clinically, unstable plaques represent a major health risk, therefore the findings at the cast in the LCCA are most interesting. At this site of interest, treatment with F8-VEGF-C showed a trend towards reduced atherosclerotic lesion size (FIG. 11C-D). Furthermore, animals treated with F8-VEGF-C presented with plaques containing significantly smaller necrotic cores (FIG. 11E). While there was no clear effect of F8-VEGF-C on collagen deposition in the lesions (FIG. 11F-G), the thickness of the plaques' fibrous cap was significantly increased in the F8-VEGF-C treatment group compared to mice receiving PBS (FIG. 11H). In addition, the smooth muscle cell area of lesions in mice injected with F8-VEGF-C was significantly increased (FIG. 11I-J), while macrophages were not affected (FIG. 11K). Further analysis revealed a significant reduction of lipids in smooth muscle cells as assessed by staining in mice treated with F8-VEGF-C (FIG. 11L-M) and no change in the lipid load of macrophages (FIG. 11N). Notably, parameters such as lesion size (FIG. 11D), necrotic core size (FIG. 11E) and fibrous cap thickness (FIG. 11H) tended to differ or differ significantly between baseline animals and PBS-treated animals.

Example 8—Treatment Effects of F8-VEGF-C on Plaques in Inner Curvature of Aortic Arch Materials and Methods
Disease Model The ApoE KO mouse model used in these experiments was as described for Example 6 above.

Analysis of Plaques in the Inner Curvature of the Aortic Arch

Hematoxylin-eosin staining of LCCA containing atherosclerotic plaques and quantification of lesion size:

Mice were euthanized, aortic arches isolated and embedded in paraffin as described in Example 7. Cryosections or paraffin sections were histologically stained with hematoxylin and eosin (HE) also as described in Example 7. Lesion size was measured as area of intima.

Quantification of Necrotic Core Size Expressed as Area:

Necrotic core area was analyzed in HE-stained sections. Necrotic core (NC) size was defined as the area devoid of nuclei underneath a formed fibrous cap.

Quantification of Collagen Deposition in Lesions Expressed as Area:

Cryosections or paraffin sections were histologically stained with HE in 70 or 40 µm intervals, respectively. Total collagen content was assessed on picrosirius red-stained consecutive sections and collagen area in atherosclerotic lesions was measured.

Quantification of Fibrous Cap Thickness:

Cryosections or paraffin sections were histologically stained with HE in 70 or 40 µm intervals, respectively. Fibrous cap (FC) thickness was assessed on picrosirius red-stained consecutive sections. FC thickness was defined as the average of length measurements in the positions overlapping with the lines of a square-shaped grid.

Results

Figure 12:
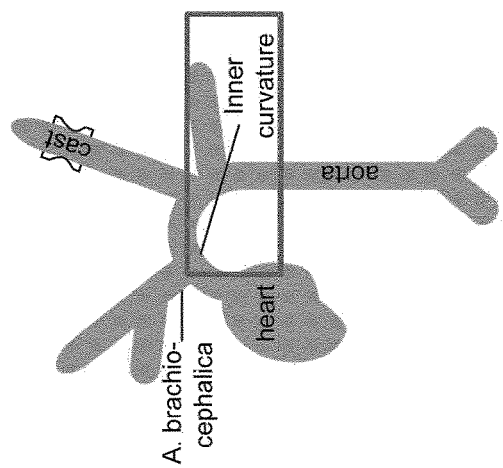
FIG. 12: Treatment effects on plaques in inner curvature of aortic arch. (A) Study overview, listing the number of animals included for analysis in the respective treatment groups. The duration of the study in number of weeks (0, 2, 9 and 11) is indicated. (B) Schematic showing the different sites of interest; results in this figure relate to the lesions forming in the inner curvature of the aortic arch. (C) Quantification of lesion size expressed as area. (D) Quantification of necrotic core size expressed as area. (E) Quantification of collagen deposition in lesions expressed as area. (F) Quantification of fibrous cap thickness. Data represent mean±SEM, analysed by one-way ANOVA.
Figure 12:
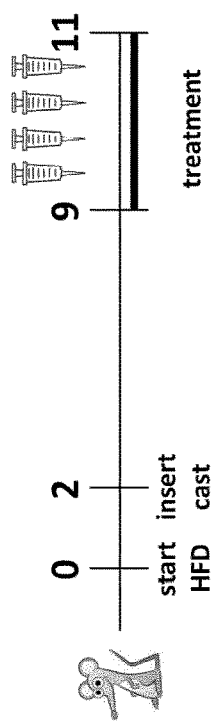
Figure 12:
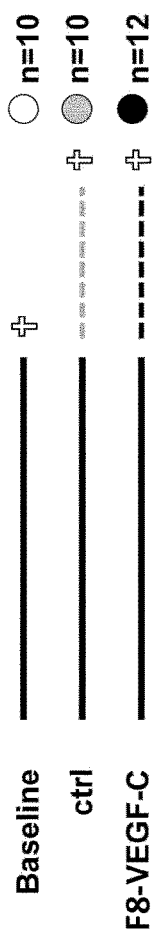

Similar to the findings in lesions forming at the cast in the LCCA, plaques in the inner curvature of the aortic arch were significantly reduced in size upon treatment with F8-VEGF-C (FIG. 12C) and had strikingly smaller necrotic cores (FIG. 12D). While the collagen deposition was not significantly changed (FIG. 12E), a strong trend towards increased fibrous cap thickness was observed in the VEGF-C treatment group (FIG. 12F). PBS-treated mice had larger lesions and necrotic cores than baseline animals (FIG. 12C-D).

Example 9—Treatment Effects of F8-VEGF-C on Plaques in Arteria Brachiocephalica

Materials and Methods
Disease Model

The ApoE KO mouse model used in these experiments was as described for Example 6 above.

Analysis of Plaques in the Arteria Brachiocephalica
Hematoxylin-Eosin Staining of LCCA Containing Atherosclerotic Plaques and Quantification of Lesion Size:

Mice were euthanized, aortic arches isolated and embedded in paraffin as described in Example 7. Cryosections or paraffin sections were histologically stained with hematoxylin and eosin (HE) also as described in Example 7. Lesion size was measured as area of intima.

Quantification of Necrotic Core Size, Collagen Deposition in Lesions and Fibrous Cap Thickness:

Necrotic core size, collagen deposition in lesions and fibrous cap thickness was quantified as set out in Example 8.

Results

Figure 13:
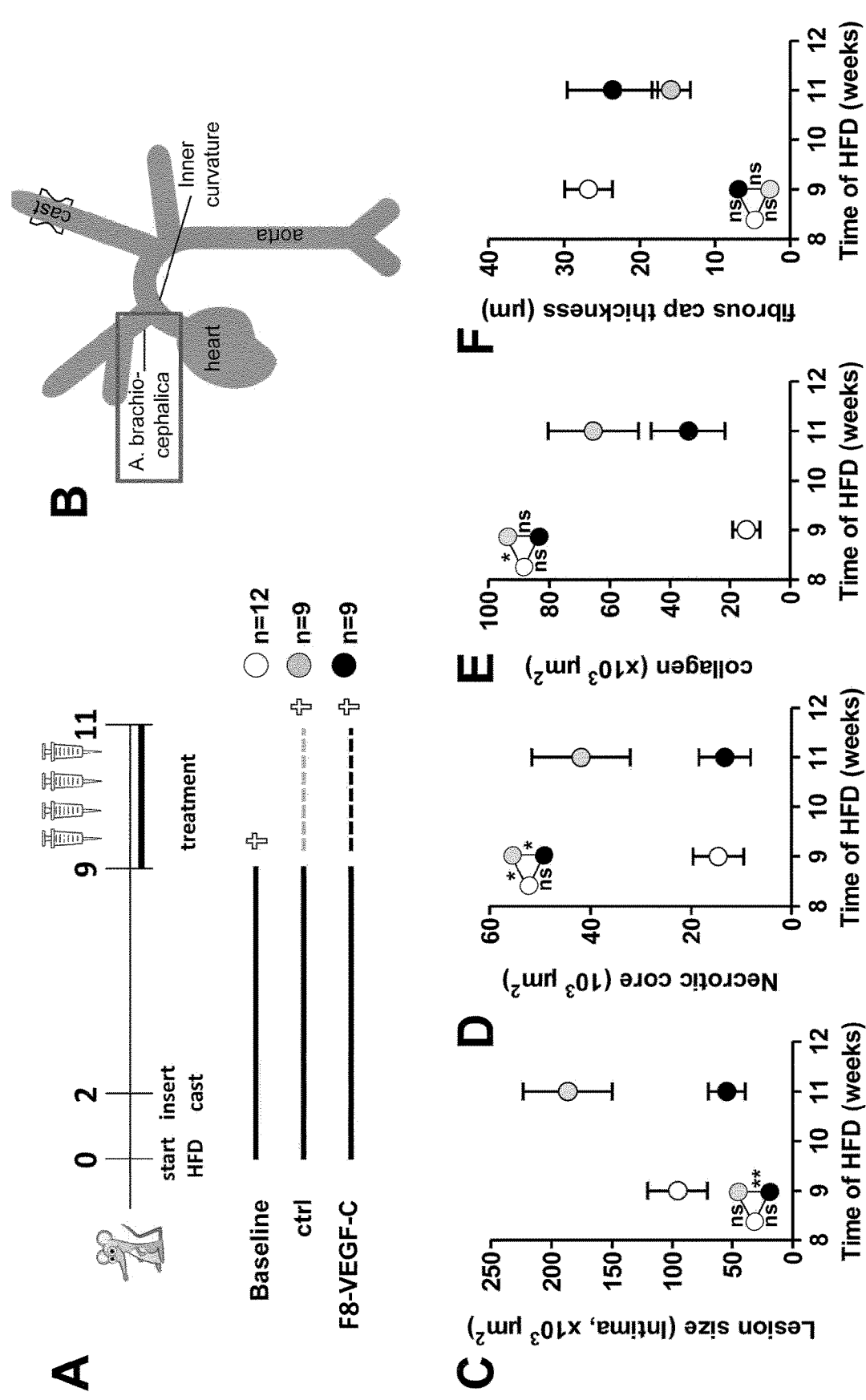
FIG. 13: Treatment effects on plaques in arteria brachiocephalica. (A) Study overview, listing the number of animals included for analysis in the respective treatment groups. The duration of the study in number of weeks (0, 2, 9 and 11) is indicated. (B) Schematic showing the different sites of interest; results in this figure relate to the lesions forming in the brachiocephalic artery. (C) Quantification of lesion size expressed as area. (D) Quantification of necrotic core size expressed as area. (E) Quantification of collagen deposition in lesions expressed as area. (F) Quantification of fibrous cap thickness. Data represent mean±SEM, analysed by one-way ANOVA.

Plaques in the brachiocephalic artery were significantly smaller in animals receiving F8-VEGF-C compared to mice injected with PBS (FIG. 13C). Furthermore, the necrotic cores of lesions found in F8-VEGF-C-treated mice were significantly reduced in size (FIG. 13D). No significant difference in the collagen content (FIG. 13E) or fibrous cap thickness (FIG. 13F) of lesions was observed in the brachiocephalic artery between PBS- and F8-VEGF-C-treated mice. Control animals (PBS-treated) presented with significantly larger lesions and necrotic cores than baseline mice (FIG. 13C-D) and tended to have thinner fibrous caps (FIG. 13F).

Examples 6 to 9—Conclusions

Several conclusions can be drawn from the experiments presented in Examples 6 to 9, as follows.

EDA is expressed in atherosclerotic plaques in mice. Therefore, F8-VEGF-C represents a suitable means for targeted delivery of VEGF-C to atherosclerotic lesions.

F8-VEGF-C treatment reduced blood levels of triglycerides and showed a trend to decrease cholesterol levels. Improving such metabolic parameters is clinically important in the setting of atherosclerosis.

Treatment of mice with F8-VEGF-C significantly reduced lesion and necrotic core size compared with control mice treated with PBS at all sites studied. Furthermore, the lesions in mice treated with F8-VEGF-C tended to have thicker fibrous caps and, in plaques forming around the cast in the LCCA, smooth muscle cell area was significantly increased. In addition, these smooth muscle cells had a reduced lipid load, indicating that they were in a healthier and fitter state.

Smaller necrotic cores, thicker fibrous caps and higher numbers of "healthy" smooth muscle cells are generally regarded as beneficial for lesion stability, reducing the risk of plaque rupture and subsequent adverse cardiovascular events. Thus, F8-VEGF-C treatment stabilized plaques and was even able to halt and reverse lesion growth. These results demonstrate the therapeutic potential of F8-VEGF-C in the setting of atherosclerosis.

It is well known in the art that atherosclerosis is a very difficult disease to treat. The standard therapy of atherosclerosis is based on the administration of statins, which are capable of slowing the progression of atherosclerosis but cannot achieve regression of the disease.

Surprisingly, F8-VEGF-C reduced the size of atherosclerotic lesions as well as improving plaque stability after only five injections.

Remarkably, these changes could be observed at all three sites of interest studied. The overall results were unexpected in view of the short therapy duration and the challenging nature of atherosclerosis itself.

```
Sequence listing

Amino acid sequence of the F8-VEGF-C fusion protein (SEQ ID NO: 1)
F8(diabody)-VEGF-C (CDRs are underlined, the linker linking the VH and VL domains of F8
is shown in italics and underlined, the linker linking F8 to VEGF-C is shown in bold and
underlined and VEGF-C is shown in bold)
EVQLLESGGGLVQPGGSLRLSCAASGFTFSLFTMSWVRQAPGKGLEWVSAISGSGGSTYY
ADSVKGRFTISRDNSKNTLYLQMNSLRAEDTAVYYCAKSTHLYLFDYWGQGTLVTVSSGG
SGGEIVLTQSPGTLSLSPGERATLSCRASQSVSMPFLAWYQQKPGQAPRLLIYGASSRATG
IPDRFSGSGSGTDFTLTISRLEPEDFAVYYCQQMRGRPPTFGQGTKVEIKSSSSGSSSSGS
SSSGAHYNTEILKSIDNEWRKTQCMPREVCIDVGKEFGVATNTFFKPPCVSVYRCGGCCN
SEGLQCMNTSTSYLSKTLFEITVPLSQGPKPVTISFANHTSCRCMSKLDVYRQVHSIIRR Amino acid sequence of the F8-VEGF-C156Ser fusion protein (SEQ ID NO: 2)
F8(diabody)-VEGF-C156Ser (CDRs are underlined, the linker linking the VH and VL
domains of F8 is shown in italics and underlined, the linker linking F8 to VEGF-C is shown in
bold and underlined and VEGF-C in shown in bold with 156Ser shown in bold, underlined
and italics)
EVQLLESGGGLVQPGGSLRLSCAASGFTFSLFTMSWVRQAPGKGLEWVSAISGSGGSTYY
ADSVKGRFTISRDNSKNTLYLQMNSLRAEDTAVYYCAKSTHLYLFDYWGQGTLVTVSSGG
SGGEIVLTQSPGTLSLSPGERATLSCRASQSVSMPFLAWYQQKPGQAPRLLIYGASSRATG
IPDRFSGSGSGTDFTLTISRLEPEDFAVYYCQQMRGRPPTFGQGTKVEIKSSSSGSSSSGS
SSSGAHYNTEILKSIDNEWRKTQCMPREVCIDVGKEFGVATNTFFKPPSVSVYRCGGCCN
SEGLQCMNTSTSYLSKTLFEITVPLSQGPKPVTISFANHTSCRCMSKLDVYRQVHSIIRR Amino acid sequence of the F8 VH domain (SEQ ID NO: 3)
EVQLLESGGGLVQPGGSLRLSCAASGFTFSLFTMSWVRQAPGKGLEWVSAISGSGGSTYY
ADSVKGRFTISRDNSKNTLYLQMNSLRAEDTAVYYCAKSTHLYLFDYWGQGTLVTVSS Amino acid sequence of the diabody linker linking the F8 VH domain to the F8 VL domain
(SEQ ID NO: 4)
GGSGG Amino acid sequence of the F8 VL domain (SEQ ID NO: 5)
EIVLTQSPGTLSLSPGERATLSCRASQSVSMPFLAWYQQKPGQAPRLLIYGASSRATGIPD
RFSGSGSGTDFTLTISRLEPEDFAVYYCQQMRGRPPTFGQGTKVEIK Amino acid sequence of the F8 diabody (SEQ ID NO: 6)
The VH and VL domain CDRs of the F8 antibody are underlined. The linker sequence is
shown in bold and underlined.
EVQLLESGGGLVQPGGSLRLSCAASGFTFSLFTMSWVRQAPGKGLEWVSAISGSGGSTYY
ADSVKGRFTISRDNSKNTLYLQMNSLRAEDTAVYYCAKSTHLYLFDYWGQGTLVTVSSGG
SGGEIVLTQSPGTLSLSPGERATLSCRASQSVSMPFLAWYQQKPGQAPRLLIYGASSRATG
IPDRFSGSGSGTDFTLTISRLEPEDFAVYYCQQMRGRPPTFGQGTKVEIK Amino acid sequences of the F8 CDR's
F8 CDR1 VH - LFT (SEQ ID NO: 7)

F8 CDR2 VH - SGSGGS (SEQ ID NO: 8)

F8 CDR3 VH - STHLYL (SEQ ID NO: 9)
```

-continued

Sequence listing

F8 CDR1 VL - MPF (SEQ ID NO: 10)

F8 CDR2 VL - GASSRAT (SEQ ID NO: 11)

F8 CDR3 VL - MRGRPP (SEQ ID NO: 12)

Amino acid sequence of human ΔNΔCVEGF-C in the F8-VEGF-C fusion proteins (SEQ ID NO: 13)
AHYNTEILKSIDNEWRKTQCMPREVCIDVGKEFGVATNTFFKPPCVSVYRCGGCCNSEGL
QCMNTSTSYLSKTLFEITVPLSQGPKPVTISFANHTSCRCMSKLDVYRQVHSIIRR Amino acid sequence of the linker linking: (i) the F8 VL domain to ΔNΔCVEGF-C in the F8-VEGF-C fusion protein or (ii) the F8 VL domain to ΔNΔCVEGF-C156Ser in the F8-VEGF-C156Ser fusion protein (SEQ ID NO: 14)
SSSSGSSSSGSSSSG Amino acid sequence of human ΔNΔCVEGF-C156Ser in the F8-VEGF-C156Ser fusion proteins (SEQ ID NO: 15)
AHYNTEILKSIDNEWRKTQCMPREVCIDVGKEFGVATNTFFKPPSVSVYRCGGCCNSEGLQ
CMNTSTSYLSKTLFEITVPLSQGPKPVTISFANHTSCRCMSKLDVYRQVHSIIRR Amino acid sequence of the KSF-VEGF-C fusion protein (SEQ ID NO: 16)
The linker sequences are underlined.
EVQLLESGGGLVQPGGSLRLSCAASGFTFSSYAMSWVRQAPGKGLEWVSAISGSGGSTY
YADSVKGRFTISRDNSKNTLYLQMNSLRAEDTAVYYCAKSPKVSLFDYWGQGTLVTVSS<u>G
GSGG</u>SELTQDPAVSVALGQTVRITCQGDSLRSYYASWYQQKPGQAPVLVIYGKNNRPSGI
PDRFSGSSSGNTASLTITGAQAEDEADYYCNSSPLNRLAVVFGGGTKLTVLG<u>SSSSGSSSS
GSSSSG</u>AHYNTEILKSIDNEWRKTQCMPREVCIDVGKEFGVATNTFFKPPCVSVYRCGG
CNSEGLQCMNTSTSYLSKTLFEITVPLSQGPKPVTISFANHTSCRCMSKLDVYRQVHSIIRR Amino acid sequence of human VEGF-D (SEQ ID NO: 17)
Phe Ala Ala Thr Phe Tyr Asp Ile Glu Thr Leu Lys Val Ile Asp Glu Glu Trp Gln Arg Thr Gln Cys Ser Pro
Arg Glu Thr Cys Val Glu Val Ala Ser Glu Leu Gly Lys Ser Thr Asn Thr Phe Phe Lys Pro Pro Cys Val
Asn Val Phe Arg Cys Gly Gly Cys Cys Asn Glu Glu Ser Leu Ile Cys Met Asn Thr Ser Thr Ser Tyr Ile
Ser Lys Gln Leu Phe Glu Ile Ser Val Pro Leu Thr Ser Val Pro Glu Leu Val Pro Val Lys Val Ala Asn His
Thr Gly Cys Lys Cys Leu Pro Thr Ala Pro Arg His Pro Tyr Ser Ile Ile Arg Arg Amino acid sequence of L19 CDR's
L19 CDR1 VH - Ser Phe Ser Met Ser (SEQ ID NO: 18)

L19 CDR2 VH - Ser Ile Ser Gly Ser Ser Gly Thr Thr Tyr Tyr Ala Asp Ser Val Lys Gly (SEQ ID NO: 19)

Alternative L19 CDR2 VH - Ser Ile Ser Gly Ser Ser Gly Thr Thr Tyr Tyr Ala Asp Ser Val Lys (SEQ ID NO: 38)

L19 CDR3 VH - Pro Phe Pro Tyr Phe Asp Tyr (SEQ ID NO: 20)

L19 CDR1 VL - Arg Ala Ser Gln Ser Val Ser Ser Ser Phe Leu Ala (SEQ ID NO: 21)

L19 CDR2 VL - Tyr Ala Ser Ser Arg Ala Thr (SEQ ID NO: 22)

L19 CDR3 VL - Gln Gln Thr Gly Arg Ile Pro Pro Thr (SEQ ID NO: 23)

Amino acid sequence of L19 VH domain (SEQ ID NO: 24)
Glu Val Gln Leu Leu Glu Ser Gly Gly Gly Leu Val Gln Pro Gly Gly Ser Leu Arg Leu Ser Cys Ala Ala
Ser Gly Phe Thr Phe Ser Ser Phe Ser Met Ser Trp Val Arg Gln Ala Pro Gly Lys Gly Leu Glu Trp Val
Ser Ser Ile Ser Gly Ser Ser Gly Thr Thr Tyr Tyr Ala Asp Ser Val Lys Gly Arg Phe Thr Ile Ser Arg Asp
Asn Ser Lys Asn Thr Leu Tyr Leu Gln Met Asn Ser Leu Arg Ala Glu Asp Thr Ala Val Tyr Tyr Cys Ala
Lys Pro Phe Pro Tyr Phe Asp Tyr Trp Gly Gln Gly Thr Leu Val Thr Val Ser Ser Amino acid sequence of L19 VL domain (SEQ ID NO: 25)
Glu Ile Val Leu Thr Gln Ser Pro Gly Thr Leu Ser Leu Ser Pro Gly Glu Arg Ala Thr Leu Ser Cys Arg Ala
Ser Gln Ser Val Ser Ser Ser Phe Leu Ala Trp Tyr Gln Gln Lys Pro Gly Gln Ala Pro Arg Leu Leu Ile Tyr
Tyr Ala Ser Ser Arg Ala Thr Gly Ile Pro Asp Arg Phe Ser Gly Ser Gly Ser Gly Thr Asp Phe Thr Leu
Thr Ile Ser Arg Leu Glu Pro Glu Asp Phe Ala Val Tyr Tyr Cys Gln Gln Thr Gly Arg Ile Pro Pro Thr Phe
Gly Gln Gly Thr Lys Val Glu Ile Lys Amino acid sequence of L19 diabody (SEQ ID NO: 26)
The VH and VL domain linker sequence is shown underlined
Glu Val Gln Leu Leu Glu Ser Gly Gly Gly Leu Val Gln Pro Gly Gly Ser Leu Arg Leu Ser Cys Ala Ala
Ser Gly Phe Thr Phe Ser Ser Phe Ser Met Ser Trp Val Arg Gln Ala Pro Gly Lys Gly Leu Glu Trp Val
Ser Ser Ile Ser Gly Ser Ser Gly Thr Thr Tyr Tyr Ala Asp Ser Val Lys Gly Arg Phe Thr Ile Ser Arg Asp
Asn Ser Lys Asn Thr Leu Tyr Leu Gln Met Asn Ser Leu Arg Ala Glu Asp Thr Ala Val Tyr Tyr Cys Ala
Lys Pro Phe Pro Tyr Phe Asp Tyr Trp Gly Gln Gly Thr Leu Val Thr Val Ser Ser <u>Gly Gly Ser Gly Gly</u>
Glu Ile Val Leu Thr Gln Ser Pro Gly Thr Leu Ser Leu Ser Pro Gly Glu Arg Ala Thr Leu Ser Cys Arg Ala
Ser Gln Ser Val Ser Ser Ser Phe Leu Ala Trp Tyr Gln Gln Lys Pro Gly Gln Ala Pro Arg Leu Leu Ile Tyr -continued Sequence listing Tyr Ala Ser Ser Arg Ala Thr Gly Ile Pro Asp Arg Phe Ser Gly Ser Gly Ser Gly Thr Asp Phe Thr Leu
Thr Ile Ser Arg Leu Glu Pro Glu Asp Phe Ala Val Tyr Tyr Cys Gln Gln Thr Gly Arg Ile Pro Pro Thr Phe
Gly Gln Gly Thr Lys Val Glu Ile Lys Amino acid sequence of F16 CDR's
F16 CDR1 VH - RYGMS (SEQ ID NO: 27)

F16 CDR2 VH - AISGSGGSTYYADSVKG (SEQ ID NO: 28)

F16 CDR3 VH - AHNAFDY (SEQ ID NO: 29)

F16 CDR1 VL - QGDSLRSYYAS (SEQ ID NO: 30)

F16 CDR2 VL - GKNNRPS (SEQ ID NO: 31)

F16 CDR3 VL - NSSVYTMPPVV (SEQ ID NO: 32)

Amino acid sequence F16 VH domain (SEQ ID NO: 33)
EVQLLESGGGLVQPGGSLRLSCAASGFTFSRYGMSWVRQAPGKGLEWVSAISGSGGSTYYADSVK
GRFTISRDNSKNTLYLQMNSLRAEDTAVYYCAKAHNAFDYWGQGTLVTVSR Amino acid sequence F16 VL domain (SEQ ID NO: 34)
SSELTQDPAVSVALGQTVRITCQGDSLRSYYASWYQQKPGQAPVLVIYGKNNRPSGIPDRFSGSSS
GNTASLTITGAQAEDEADYYCNSSVYTMPPVVFGGGTKLTVLG Alternative amino acid sequence F16 VL domain (SEQ ID NO: 39)
SSELTQDPAVSVALGQTVRITCQGDSLRSYYASWYQQKPGQAPVLVIYGKNNRPSGIPDRFSGSSS
GNTASLTITGAQAEDEADYYCNSSVYTMPPVVFGGGTKLTVL Amino acid sequence of the F16 diabody (SEQ ID NO: 35)
The VH and VL domain linker sequence is shown underlined
EVQLLESGGGLVQPGGSLRLSCAASGFTFSRYGMSWVRQAPGKGLEWVSAISGSGGSTYYADSVK
GRFTISRDNSKNTLYLQMNSLRAEDTAVYYCAKAHNAFDYWGQGTLVTVSR<u>GGSGGS</u>SELTQDPAV
SVALGQTVRITCQGDSLRSYYASWYQQKPGQAPVLVIYGKNNRPSGIPDRFSGSSSGNTASLTITGA
QAEDEADYYCNSSVYTMPPVVFGGGTKLTVLG Alternative amino acid sequence of the F16 diabody (SEQ ID NO: 40)
The VH and VL domain linker sequence is shown underlined
EVQLLESGGGLVQPGGSLRLSCAASGFTFSRYGMSWVRQAPGKGLEWVSAISGSGGSTYYADSVK
GRFTISRDNSKNTLYLQMNSLRAEDTAVYYCAKAHNAFDYWGQGTLVTVSR<u>GGSGGS</u>SELTQDPAV
SVALGQTVRITCQGDSLRSYYASWYQQKPGQAPVLVIYGKNNRPSGIPDRFSGSSSGNTASLTITGA
QAEDEADYYCNSSVYTMPPVVFGGGTKLTVL VH and VL domain linker sequence in an scFv molecule (SEQ ID NO: 36)
GGGSGGGSGG VH and VL domain linker sequence in an scFv molecule (SEQ ID NO: 37)
GGGGSGGGGSGGGG

The invention claimed is:

1. A conjugate comprising:
   (i) a diabody, which binds the Extra Domain-A (ED-A) of fibronectin, and
   (ii) vascular endothelial growth factor C (VEGF-C) wherein said conjugate comprises the sequence set forth in SEQ ID NO: 1.

2. The conjugate of claim 1 in a pharmaceutically acceptable carrier.

3. A conjugate comprising:
   (i) a diabody, which binds the Extra Domain-A (ED-A) of fibronectin, and
   (ii) vascular endothelial growth factor C (VEGF-C) wherein said conjugate comprises the sequence set forth in SEQ ID NO: 2.

4. The conjugate of claim 3 in a pharmaceutically acceptable carrier.

* * * * *

SEQUENCE LISTING

<160> NUMBER OF SEQ ID NOS: 40

<210> SEQ ID NO 1
<211> LENGTH: 362
<212> TYPE: PRT
<213> ORGANISM: Artificial Sequence
<220> FEATURE:
<223> OTHER INFORMATION: F8-VEGF-C fusion protein

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
                20                  25                  30

Thr Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Thr His Leu Tyr Leu Phe Asp Tyr Trp Gly Gln Gly Thr
            100                 105                 110

Leu Val Thr Val Ser Ser Gly Gly Gly Gly Glu Ile Val Leu Thr
        115                 120                 125

Gln Ser Pro Gly Thr Leu Ser Leu Ser Pro Gly Glu Arg Ala Thr Leu
    130                 135                 140

Ser Cys Arg Ala Ser Gln Ser Val Ser Met Pro Phe Leu Ala Trp Tyr
145                 150                 155                 160

Gln Gln Lys Pro Gly Gln Ala Pro Arg Leu Leu Ile Tyr Gly Ala Ser
                165                 170                 175

Ser Arg Ala Thr Gly Ile Pro Asp Arg Phe Ser Gly Ser Gly Ser Gly
            180                 185                 190

Thr Asp Phe Thr Leu Thr Ile Ser Arg Leu Glu Pro Glu Asp Phe Ala
        195                 200                 205

Val Tyr Tyr Cys Gln Gln Met Arg Gly Arg Pro Thr Phe Gly Gln
    210                 215                 220

Gly Thr Lys Val Glu Ile Lys Ser Ser Ser Gly Ser Ser Ser Ser
225                 230                 235                 240

Gly Ser Ser Ser Gly Ala His Tyr Asn Thr Glu Ile Leu Lys Ser
            245                 250                 255

Ile Asp Asn Glu Trp Arg Lys Thr Gln Cys Met Pro Arg Glu Val Cys
            260                 265                 270

Ile Asp Val Gly Lys Glu Phe Gly Val Ala Thr Asn Thr Phe Phe Lys
            275                 280                 285

Pro Pro Cys Val Ser Val Tyr Arg Cys Gly Gly Cys Cys Asn Ser Glu
        290                 295                 300

Gly Leu Gln Cys Met Asn Thr Ser Thr Ser Tyr Leu Ser Lys Thr Leu
305                 310                 315                 320

Phe Glu Ile Thr Val Pro Leu Ser Gln Gly Pro Lys Pro Val Thr Ile
            325                 330                 335

Ser Phe Ala Asn His Thr Ser Cys Arg Cys Met Ser Lys Leu Asp Val
            340                 345                 350

Tyr Arg Gln Val His Ser Ile Ile Arg Arg
        355                 360

<210> SEQ ID NO 2
<211> LENGTH: 362
<212> TYPE: PRT
<213> ORGANISM: Artificial Sequence
<220> FEATURE:
<223> OTHER INFORMATION: F8-VEGF-C156Ser fusion protein

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser Gly Gly Ser Gly Gly Glu Ile Val Leu Thr
        115                 120                 125

Gln Ser Pro Gly Thr Leu Ser Leu Ser Pro Gly Glu Arg Ala Thr Leu
130                 135                 140

Ser Cys Arg Ala Ser Gln Ser Val Ser Met Pro Phe Leu Ala Trp Tyr
145                 150                 155                 160

Gln Gln Lys Pro Gly Gln Ala Pro Arg Leu Leu Ile Tyr Gly Ala Ser
                165                 170                 175

Ser Arg Ala Thr Gly Ile Pro Asp Arg Phe Ser Gly Ser Gly Ser Gly
            180                 185                 190

Thr Asp Phe Thr Leu Thr Ile Ser Arg Leu Glu Pro Glu Asp Phe Ala
        195                 200                 205

Val Tyr Tyr Cys Gln Gln Met Arg Gly Arg Pro Pro Thr Phe Gly Gln
    210                 215                 220

Gly Thr Lys Val Glu Ile Lys Ser Ser Ser Gly Ser Ser Ser Ser
225                 230                 235                 240

Gly Ser Ser Ser Gly Ala His Tyr Asn Thr Glu Ile Leu Lys Ser
            245                 250                 255

Ile Asp Asn Glu Trp Arg Lys Thr Gln Cys Met Pro Arg Glu Val Cys
        260                 265                 270

Ile Asp Val Gly Lys Glu Phe Gly Val Ala Thr Asn Thr Phe Phe Lys
        275                 280                 285

Pro Pro Ser Val Ser Val Tyr Arg Cys Gly Gly Cys Cys Asn Ser Glu
290                 295                 300

Gly Leu Gln Cys Met Asn Thr Ser Thr Ser Tyr Leu Ser Lys Thr Leu
305                 310                 315                 320

Phe Glu Ile Thr Val Pro Leu Ser Gln Gly Pro Lys Pro Val Thr Ile
                325                 330                 335

Ser Phe Ala Asn His Thr Ser Cys Arg Cys Met Ser Lys Leu Asp Val
            340                 345                 350

Tyr Arg Gln Val His Ser Ile Ile Arg Arg
        355                 360

<210> SEQ ID NO 3
<211> LENGTH: 118
<212> TYPE: PRT
<213> ORGANISM: Artificial Sequence
<220> FEATURE:
<223> OTHER INFORMATION: F8 VH domain

<400> SEQUENCE: 3

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Leu Phe
                 20                  25                  30

Thr Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 4
<211> LENGTH: 5
<212> TYPE: PRT
<213> ORGANISM: Artificial Sequence
<220> FEATURE:
<223> OTHER INFORMATION: diabody linker linking the F8 VH domain to the
      F8 VL domain

<400> SEQUENCE: 4

Gly Gly Ser Gly Gly
1               5

<210> SEQ ID NO 5
<211> LENGTH: 108
<212> TYPE: PRT
<213> ORGANISM: Artificial Sequence
<220> FEATURE:
<223> OTHER INFORMATION: F8 VL domain

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105

<210> SEQ ID NO 6
<211> LENGTH: 231
<212> TYPE: PRT
<213> ORGANISM: Artificial Sequence
<220> FEATURE:
<223> OTHER INFORMATION: F8 diabody

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser Gly Gly Ser Gly Gly Glu Ile Val Leu Thr
            115                 120                 125

Gln Ser Pro Gly Thr Leu Ser Leu Ser Pro Gly Glu Arg Ala Thr Leu
        130                 135                 140

Ser Cys Arg Ala Ser Gln Ser Val Ser Met Pro Phe Leu Ala Trp Tyr
145                 150                 155                 160

Gln Gln Lys Pro Gly Gln Ala Pro Arg Leu Leu Ile Tyr Gly Ala Ser
                165                 170                 175

Ser Arg Ala Thr Gly Ile Pro Asp Arg Phe Ser Gly Ser Gly Ser Gly
            180                 185                 190

Thr Asp Phe Thr Leu Thr Ile Ser Arg Leu Glu Pro Glu Asp Phe Ala
        195                 200                 205

Val Tyr Tyr Cys Gln Gln Met Arg Gly Arg Pro Pro Thr Phe Gly Gln
    210                 215                 220

Gly Thr Lys Val Glu Ile Lys
225                 230

<210> SEQ ID NO 7
<211> LENGTH: 3
<212> TYPE: PRT
<213> ORGANISM: Artificial Sequence
<220> FEATURE:
<223> OTHER INFORMATION: F8 CDR1 VH

<400> SEQUENCE: 7

Leu Phe Thr
1

<210> SEQ ID NO 8
<211> LENGTH: 6
<212> TYPE: PRT
<213> ORGANISM: Artificial Sequence
<220> FEATURE:
<223> OTHER INFORMATION: F8 CDR2 VH

<400> SEQUENCE: 8

Ser Gly Ser Gly Gly Ser
1               5

<210> SEQ ID NO 9
<211> LENGTH: 6
<212> TYPE: PRT
<213> ORGANISM: Artificial Sequence
<220> FEATURE:
<223> OTHER INFORMATION: F8 CDR3 VH

<400> SEQUENCE: 9

Ser Thr His Leu Tyr Leu
1               5

<210> SEQ ID NO 10
<211> LENGTH: 3
<212> TYPE: PRT
<213> ORGANISM: Artificial Sequence
<220> FEATURE:
```

<223> OTHER INFORMATION: F8 CDR1 VL

<400> SEQUENCE: 10

Met Pro Phe
1

<210> SEQ ID NO 11
<211> LENGTH: 7
<212> TYPE: PRT
<213> ORGANISM: Artificial Sequence
<220> FEATURE:
<223> OTHER INFORMATION: F8 CDR2 VL

<400> SEQUENCE: 11

Gly Ala Ser Ser Arg Ala Thr
1               5

<210> SEQ ID NO 12
<211> LENGTH: 6
<212> TYPE: PRT
<213> ORGANISM: Artificial Sequence
<220> FEATURE:
<223> OTHER INFORMATION: F8 CDR3 VL

<400> SEQUENCE: 12

Met Arg Gly Arg Pro Pro
1               5

<210> SEQ ID NO 13
<211> LENGTH: 116
<212> TYPE: PRT
<213> ORGANISM: Homo sapiens
<220> FEATURE:
<221> NAME/KEY: misc_feature
<223> OTHER INFORMATION: deltaNdeltaCVEGF-C in the F8-VEGF-C fusion
      proteins

<400> SEQUENCE: 13

Ala His Tyr Asn Thr Glu Ile Leu Lys Ser Ile Asp Asn Glu Trp Arg
1               5                   10                  15

Lys Thr Gln Cys Met Pro Arg Glu Val Cys Ile Asp Val Gly Lys Glu
            20                  25                  30

Phe Gly Val Ala Thr Asn Thr Phe Phe Lys Pro Pro Cys Val Ser Val
        35                  40                  45

Tyr Arg Cys Gly Gly Cys Cys Asn Ser Glu Gly Leu Gln Cys Met Asn
    50                  55                  60

Thr Ser Thr Ser Tyr Leu Ser Lys Thr Leu Phe Glu Ile Thr Val Pro
65                  70                  75                  80

Leu Ser Gln Gly Pro Lys Pro Val Thr Ile Ser Phe Ala Asn His Thr
                85                  90                  95

Ser Cys Arg Cys Met Ser Lys Leu Asp Val Tyr Arg Gln Val His Ser
            100                 105                 110

Ile Ile Arg Arg
        115

<210> SEQ ID NO 14
<211> LENGTH: 15
<212> TYPE: PRT
<213> ORGANISM: Artificial Sequence
<220> FEATURE:
<223> OTHER INFORMATION: linker linking: (i) the F8 VL domain to
      deltaNdeltaCVEGF-C in the F8-VEGF-C fusion protein or (ii) the F8
      VL domain to deltaNdeltaCVEGF-C156Ser in the F8-VEGF-C156Ser
      fusion protein

```
<400> SEQUENCE: 14

Ser Ser Ser Ser Gly Ser Ser Ser Gly Ser Ser Ser Gly
1               5                   10                  15

<210> SEQ ID NO 15
<211> LENGTH: 116
<212> TYPE: PRT
<213> ORGANISM: Homo sapiens
<220> FEATURE:
<221> NAME/KEY: misc_feature
<223> OTHER INFORMATION: deltaNdeltaCVEGF-C156Ser in the F8-VEGF-C156Ser
      fusion proteins

<400> SEQUENCE: 15

Ala His Tyr Asn Thr Glu Ile Leu Lys Ser Ile Asp Asn Glu Trp Arg
1               5                   10                  15

Lys Thr Gln Cys Met Pro Arg Glu Val Cys Ile Asp Val Gly Lys Glu
                20                  25                  30

Phe Gly Val Ala Thr Asn Thr Phe Phe Lys Pro Pro Ser Val Ser Val
            35                  40                  45

Tyr Arg Cys Gly Gly Cys Cys Asn Ser Glu Gly Leu Gln Cys Met Asn
        50                  55                  60

Thr Ser Thr Ser Tyr Leu Ser Lys Thr Leu Phe Glu Ile Thr Val Pro
65                  70                  75                  80

Leu Ser Gln Gly Pro Lys Pro Val Thr Ile Ser Phe Ala Asn His Thr
                85                  90                  95

Ser Cys Arg Cys Met Ser Lys Leu Asp Val Tyr Arg Gln Val His Ser
                100                 105                 110

Ile Ile Arg Arg
        115

<210> SEQ ID NO 16
<211> LENGTH: 362
<212> TYPE: PRT
<213> ORGANISM: Artificial Sequence
<220> FEATURE:
<223> OTHER INFORMATION: KSF-VEGF-C fusion protein

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Lys Val Ser Leu Phe Asp Tyr Trp Gly Gln Gly Thr
                100                 105                 110

Leu Val Thr Val Ser Ser Gly Gly Gly Gly Ser Glu Leu Thr Gln
            115                 120                 125

Asp Pro Ala Val Ser Val Ala Leu Gly Gln Thr Val Arg Ile Thr Cys
        130                 135                 140
```

```
Gln Gly Asp Ser Leu Arg Ser Tyr Tyr Ala Ser Trp Tyr Gln Gln Lys
145                 150                 155                 160

Pro Gly Gln Ala Pro Val Leu Val Ile Tyr Gly Lys Asn Asn Arg Pro
                165                 170                 175

Ser Gly Ile Pro Asp Arg Phe Ser Gly Ser Ser Ser Gly Asn Thr Ala
            180                 185                 190

Ser Leu Thr Ile Thr Gly Ala Gln Ala Glu Asp Glu Ala Asp Tyr Tyr
        195                 200                 205

Cys Asn Ser Ser Pro Leu Asn Arg Leu Ala Val Val Phe Gly Gly Gly
    210                 215                 220

Thr Lys Leu Thr Val Leu Gly Ser Ser Ser Gly Ser Ser Ser
225                 230                 235                 240

Gly Ser Ser Ser Gly Ala His Tyr Asn Thr Glu Ile Leu Lys Ser
            245                 250                 255

Ile Asp Asn Glu Trp Arg Lys Thr Gln Cys Met Pro Arg Glu Val Cys
        260                 265                 270

Ile Asp Val Gly Lys Glu Phe Gly Val Ala Thr Asn Thr Phe Phe Lys
        275                 280                 285

Pro Pro Cys Val Ser Val Tyr Arg Cys Gly Gly Cys Cys Asn Ser Glu
        290                 295                 300

Gly Leu Gln Cys Met Asn Thr Ser Thr Ser Tyr Leu Ser Lys Thr Leu
305                 310                 315                 320

Phe Glu Ile Thr Val Pro Leu Ser Gln Gly Pro Lys Pro Val Thr Ile
                325                 330                 335

Ser Phe Ala Asn His Thr Ser Cys Arg Cys Met Ser Lys Leu Asp Val
            340                 345                 350

Tyr Arg Gln Val His Ser Ile Ile Arg Arg
            355                 360

<210> SEQ ID NO 17
<211> LENGTH: 117
<212> TYPE: PRT
<213> ORGANISM: Homo sapiens
<220> FEATURE:
<221> NAME/KEY: MISC_FEATURE
<223> OTHER INFORMATION: VEGF-D

<400> SEQUENCE: 17

Phe Ala Ala Thr Phe Tyr Asp Ile Glu Thr Leu Lys Val Ile Asp Glu
1               5                   10                  15

Glu Trp Gln Arg Thr Gln Cys Ser Pro Arg Glu Thr Cys Val Glu Val
                20                  25                  30

Ala Ser Glu Leu Gly Lys Ser Thr Asn Thr Phe Phe Lys Pro Pro Cys
            35                  40                  45

Val Asn Val Phe Arg Cys Gly Gly Cys Cys Asn Glu Glu Ser Leu Ile
        50                  55                  60

Cys Met Asn Thr Ser Thr Ser Tyr Ile Ser Lys Gln Leu Phe Glu Ile
65                  70                  75                  80

Ser Val Pro Leu Thr Ser Val Pro Glu Leu Val Pro Val Lys Val Ala
                85                  90                  95

Asn His Thr Gly Cys Lys Cys Leu Pro Thr Ala Pro Arg His Pro Tyr
            100                 105                 110

Ser Ile Ile Arg Arg
        115

<210> SEQ ID NO 18
```

```
<211> LENGTH: 5
<212> TYPE: PRT
<213> ORGANISM: Artificial Sequence
<220> FEATURE:
<223> OTHER INFORMATION: L19 CDR1 VH

<400> SEQUENCE: 18

Ser Phe Ser Met Ser
1               5

<210> SEQ ID NO 19
<211> LENGTH: 17
<212> TYPE: PRT
<213> ORGANISM: Artificial Sequence
<220> FEATURE:
<223> OTHER INFORMATION: L19 CDR2 VH

<400> SEQUENCE: 19

Ser Ile Ser Gly Ser Ser Gly Thr Thr Tyr Tyr Ala Asp Ser Val Lys
1               5                   10                  15

Gly

<210> SEQ ID NO 20
<211> LENGTH: 7
<212> TYPE: PRT
<213> ORGANISM: Artificial Sequence
<220> FEATURE:
<223> OTHER INFORMATION: L19 CDR3 VH

<400> SEQUENCE: 20

Pro Phe Pro Tyr Phe Asp Tyr
1               5

<210> SEQ ID NO 21
<211> LENGTH: 12
<212> TYPE: PRT
<213> ORGANISM: Artificial Sequence
<220> FEATURE:
<223> OTHER INFORMATION: L19 CDR1 VL

<400> SEQUENCE: 21

Arg Ala Ser Gln Ser Val Ser Ser Ser Phe Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: L19 CDR2 VL

<400> SEQUENCE: 22

Tyr Ala Ser Ser Arg Ala Thr
1               5

<210> SEQ ID NO 23
<211> LENGTH: 9
<212> TYPE: PRT
<213> ORGANISM: Artificial Sequence
<220> FEATURE:
<223> OTHER INFORMATION: L19 CDR3 VL

<400> SEQUENCE: 23

Gln Gln Thr Gly Arg Ile Pro Pro Thr
1               5
```

<210> SEQ ID NO 24
<211> LENGTH: 116
<212> TYPE: PRT
<213> ORGANISM: Artificial Sequence
<220> FEATURE:
<223> OTHER INFORMATION: L19 VH domain

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
            115
```

<210> SEQ ID NO 25
<211> LENGTH: 108
<212> TYPE: PRT
<213> ORGANISM: Artificial Sequence
<220> FEATURE:
<223> OTHER INFORMATION: L19 VL domain

<400> SEQUENCE: 25

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105
```

<210> SEQ ID NO 26
<211> LENGTH: 229
<212> TYPE: PRT
<213> ORGANISM: Artificial Sequence
<220> FEATURE:
<223> OTHER INFORMATION: L19 diabody

<400> SEQUENCE: 26

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30
```

-continued

Ser Met Ser Trp Val Arg Gln Ala Pro Gly Lys Gly Leu Glu Trp Val
          35                  40                  45

Ser Ser Ile Ser Gly Ser Ser Gly Thr Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
            100                 105                 110

Thr Val Ser Ser Gly Gly Ser Gly Gly Glu Ile Val Leu Thr Gln Ser
            115                 120                 125

Pro Gly Thr Leu Ser Leu Ser Pro Gly Glu Arg Ala Thr Leu Ser Cys
            130                 135                 140

Arg Ala Ser Gln Ser Val Ser Ser Ser Phe Leu Ala Trp Tyr Gln Gln
145                 150                 155                 160

Lys Pro Gly Gln Ala Pro Arg Leu Leu Ile Tyr Tyr Ala Ser Ser Arg
                165                 170                 175

Ala Thr Gly Ile Pro Asp Arg Phe Ser Gly Ser Gly Ser Gly Thr Asp
            180                 185                 190

Phe Thr Leu Thr Ile Ser Arg Leu Glu Pro Glu Asp Phe Ala Val Tyr
            195                 200                 205

Tyr Cys Gln Gln Thr Gly Arg Ile Pro Pro Thr Phe Gly Gln Gly Thr
            210                 215                 220

Lys Val Glu Ile Lys
225

<210> SEQ ID NO 27
<211> LENGTH: 5
<212> TYPE: PRT
<213> ORGANISM: Artificial Sequence
<220> FEATURE:
<223> OTHER INFORMATION: F16 CDR1 VH

<400> SEQUENCE: 27

Arg Tyr Gly Met Ser
1               5

<210> SEQ ID NO 28
<211> LENGTH: 17
<212> TYPE: PRT
<213> ORGANISM: Artificial Sequence
<220> FEATURE:
<223> OTHER INFORMATION: F16 CDR2 VH

<400> SEQUENCE: 28

Ala Ile Ser Gly Ser Gly Gly Ser Thr Tyr Tyr Ala Asp Ser Val Lys
1               5                   10                  15

Gly

<210> SEQ ID NO 29
<211> LENGTH: 7
<212> TYPE: PRT
<213> ORGANISM: Artificial Sequence
<220> FEATURE:
<223> OTHER INFORMATION: F16 CDR3 VH

<400> SEQUENCE: 29

Ala His Asn Ala Phe Asp Tyr

<210> SEQ ID NO 30
<211> LENGTH: 11
<212> TYPE: PRT
<213> ORGANISM: Artificial Sequence
<220> FEATURE:
<223> OTHER INFORMATION: F16 CDR1 VL

<400> SEQUENCE: 30

Gln Gly Asp Ser Leu Arg Ser Tyr Tyr Ala Ser
1               5                   10

<210> SEQ ID NO 31
<211> LENGTH: 7
<212> TYPE: PRT
<213> ORGANISM: Artificial Sequence
<220> FEATURE:
<223> OTHER INFORMATION: F16 CDR2 VL

<400> SEQUENCE: 31

Gly Lys Asn Asn Arg Pro Ser
1               5

<210> SEQ ID NO 32
<211> LENGTH: 11
<212> TYPE: PRT
<213> ORGANISM: Artificial Sequence
<220> FEATURE:
<223> OTHER INFORMATION: F16 CDR3 VL

<400> SEQUENCE: 32

Asn Ser Ser Val Tyr Thr Met Pro Pro Val Val
1               5                   10

<210> SEQ ID NO 33
<211> LENGTH: 116
<212> TYPE: PRT
<213> ORGANISM: Artificial Sequence
<220> FEATURE:
<223> OTHER INFORMATION: F16 VH domain

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 34
<211> LENGTH: 109
<212> TYPE: PRT

<213> ORGANISM: Artificial Sequence
<220> FEATURE:
<223> OTHER INFORMATION: F16 VL domain

<400> SEQUENCE: 34

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu Gly
            100                 105
```

<210> SEQ ID NO 35
<211> LENGTH: 230
<212> TYPE: PRT
<213> ORGANISM: Artificial Sequence
<220> FEATURE:
<223> OTHER INFORMATION: F16 diabody

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg Gly Gly Ser Gly Gly Ser Ser Glu Leu Thr Gln Asp
            115                 120                 125

Pro Ala Val Ser Val Ala Leu Gly Gln Thr Val Arg Ile Thr Cys Gln
        130                 135                 140

Gly Asp Ser Leu Arg Ser Tyr Tyr Ala Ser Trp Tyr Gln Gln Lys Pro
145                 150                 155                 160

Gly Gln Ala Pro Val Leu Val Ile Tyr Gly Lys Asn Asn Arg Pro Ser
                165                 170                 175

Gly Ile Pro Asp Arg Phe Ser Gly Ser Ser Ser Gly Asn Thr Ala Ser
            180                 185                 190

Leu Thr Ile Thr Gly Ala Gln Ala Glu Asp Glu Ala Asp Tyr Tyr Cys
        195                 200                 205

Asn Ser Ser Val Tyr Thr Met Pro Pro Val Val Phe Gly Gly Gly Thr
    210                 215                 220
```

```
Lys Leu Thr Val Leu Gly
225                 230

<210> SEQ ID NO 36
<211> LENGTH: 10
<212> TYPE: PRT
<213> ORGANISM: Artificial Sequence
<220> FEATURE:
<223> OTHER INFORMATION: VH and VL domain linker sequence in an scFv
      molecule

<400> SEQUENCE: 36

Gly Gly Gly Ser Gly Gly Gly Ser Gly Gly
1               5                   10

<210> SEQ ID NO 37
<211> LENGTH: 14
<212> TYPE: PRT
<213> ORGANISM: Artificial Sequence
<220> FEATURE:
<223> OTHER INFORMATION: VH and VL domain linker sequence in an scFv
      molecule

<400> SEQUENCE: 37

Gly Gly Gly Gly Ser Gly Gly Gly Gly Ser Gly Gly Gly Gly
1               5                   10

<210> SEQ ID NO 38
<211> LENGTH: 16
<212> TYPE: PRT
<213> ORGANISM: Artificial Sequence
<220> FEATURE:
<223> OTHER INFORMATION: Alternative L19 CDR2 VH

<400> SEQUENCE: 38

Ser Ile Ser Gly Ser Ser Gly Thr Thr Tyr Tyr Ala Asp Ser Val Lys
1               5                   10                  15

<210> SEQ ID NO 39
<211> LENGTH: 108
<212> TYPE: PRT
<213> ORGANISM: Artificial Sequence
<220> FEATURE:
<223> OTHER INFORMATION: Alternative F16 VL domain

<400> SEQUENCE: 39

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu
            100                 105

<210> SEQ ID NO 40
<211> LENGTH: 229
<212> TYPE: PRT
```

<213> ORGANISM: Artificial Sequence
<220> FEATURE:
<223> OTHER INFORMATION: Alternative F16 diabody

<400> SEQUENCE: 40

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg Gly Gly Ser Gly Gly Ser Ser Glu Leu Thr Gln Asp
        115                 120                 125

Pro Ala Val Ser Val Ala Leu Gly Gln Thr Val Arg Ile Thr Cys Gln
    130                 135                 140

Gly Asp Ser Leu Arg Ser Tyr Tyr Ala Ser Trp Tyr Gln Gln Lys Pro
145                 150                 155                 160

Gly Gln Ala Pro Val Leu Val Ile Tyr Gly Lys Asn Asn Arg Pro Ser
                165                 170                 175

Gly Ile Pro Asp Arg Phe Ser Gly Ser Ser Ser Gly Asn Thr Ala Ser
            180                 185                 190

Leu Thr Ile Thr Gly Ala Gln Ala Glu Asp Glu Ala Asp Tyr Tyr Cys
        195                 200                 205

Asn Ser Ser Val Tyr Thr Met Pro Pro Val Val Phe Gly Gly Gly Thr
    210                 215                 220

Lys Leu Thr Val Leu
225
```